United States Patent
DeSalvo et al.

(10) Patent No.: US 9,675,754 B2
(45) Date of Patent: Jun. 13, 2017

(54) AUTOINJECTOR

(71) Applicant: Nuance Designs of CT, LLC, Woodbridge, CT (US)

(72) Inventors: David DeSalvo, Lake Hiawatha, NJ (US); Carlos Guillermo, Atascadero, CA (US)

(73) Assignee: Nuance Designs, LLC, Pine Brooke, NJ (US)

( * ) Notice: Subject to any disclaimer, the term of this patent is extended or adjusted under 35 U.S.C. 154(b) by 608 days.

(21) Appl. No.: 14/060,236

(22) Filed: Oct. 22, 2013

(65) Prior Publication Data
US 2014/0114250 A1 Apr. 24, 2014

Related U.S. Application Data

(60) Provisional application No. 61/717,704, filed on Oct. 24, 2012.

(51) Int. Cl.
*A61M 5/20* (2006.01)
*A61M 5/155* (2006.01)
(Continued)

(52) U.S. Cl.
CPC ........ *A61M 5/155* (2013.01); *A61M 5/16877* (2013.01); *A61M 5/2033* (2013.01);
(Continued)

(58) Field of Classification Search
CPC .... A61M 2005/2013; A61M 2005/206; A61M 5/155; A61M 5/16877; A61M 5/2033;
(Continued)

(56) References Cited

U.S. PATENT DOCUMENTS

| 1,800,156 A | 4/1931 | Rotheim |
| 4,396,016 A | 8/1983 | Becker |

(Continued)

FOREIGN PATENT DOCUMENTS

| CA | 2899558 A1 | 10/2014 |
| CN | 1585655 A | 2/2005 |

(Continued)

OTHER PUBLICATIONS

International Search Report, International Application No. PCT/US13/66298 (date of mailing Mar. 19, 2014).
(Continued)

*Primary Examiner* — Quynh-Nhu H Vu
(74) *Attorney, Agent, or Firm* — Kim Winston, LLP

(57) ABSTRACT

An autoinjector includes a main body having a container, the container having a drug therein, a hollow needle coupled to the container through which the drug can be delivered. The autoinjector also has a power source having a liquefied gas therein as a driver, a flow regulator, and at least one outlet through which some of the driver can exit the power pack in a gaseous state. The power source and container are coupled together for operation such that, when an injection is initiated, the flow regulator will control an exit rate of the driver such that the liquefied gas in the power source is maintained at substantially its vapor pressure and the power source will adjustably apply a force to deliver the drug via the hollow needle at a delivery rate that is a constant delivery rate.

21 Claims, 38 Drawing Sheets

(51) Int. Cl.
*A61M 5/168* (2006.01)
*A61M 5/32* (2006.01)

(52) U.S. Cl.
CPC ......... *A61M 5/2053* (2013.01); *A61M 5/2066* (2013.01); *A61M 5/3204* (2013.01); *A61M 2005/206* (2013.01); *A61M 2005/2013* (2013.01)

(58) Field of Classification Search
CPC .............. A61M 5/2053; A61M 5/2066; A61M 5/3204; A61M 2205/8225; A61M 2205/8231; A61M 11/065
See application file for complete search history.

(56) References Cited

U.S. PATENT DOCUMENTS

| | | | |
|---|---|---|---|
| 4,698,062 A | 10/1987 | Gale et al. | |
| 5,554,148 A | 9/1996 | Aebischer et al. | |
| 6,726,673 B1 | 4/2004 | Zhang et al. | |
| 7,654,983 B2 * | 2/2010 | De La Sema | A61M 5/2053 604/141 |
| 7,824,373 B2 | 11/2010 | Kim et al. | |
| 8,187,226 B2 | 5/2012 | Stamp et al. | |
| 2003/0168480 A1 | 9/2003 | Kim | |
| 2005/0070848 A1 | 3/2005 | Kim et al. | |
| 2008/0299173 A1 | 12/2008 | Story et al. | |
| 2009/0254047 A1 * | 10/2009 | Thogersen | A61M 5/31585 604/211 |
| 2010/0069846 A1 | 3/2010 | Stamp | |
| 2010/0178581 A1 | 7/2010 | An et al. | |
| 2010/0185178 A1 | 7/2010 | Sharp et al. | |
| 2010/0228122 A1 | 9/2010 | Keenan et al. | |
| 2011/0034879 A1 * | 2/2011 | Crow | A61M 5/2033 604/197 |
| 2011/0152680 A1 | 6/2011 | Kim et al. | |
| 2013/0237916 A1 | 9/2013 | Hanson et al. | |
| 2014/0114248 A1 | 4/2014 | DeSalvo et al. | |

FOREIGN PATENT DOCUMENTS

| | | |
|---|---|---|
| GB | 2447339 A | 9/2008 |
| JP | 2014104113 A | 6/2014 |
| WO | 9402188 A1 | 2/1994 |
| WO | 0189607 A2 | 11/2001 |
| WO | 0226102 A2 | 4/2002 |
| WO | 03039634 A1 | 5/2003 |
| WO | 03049671 A2 | 6/2003 |
| WO | 2005056077 A2 | 6/2005 |
| WO | 2006084876 A1 | 8/2006 |
| WO | 2011101379 A1 | 8/2011 |
| WO | 2011117592 A1 | 9/2011 |
| WO | 2015063506 A1 | 5/2015 |

OTHER PUBLICATIONS

International Written Opinion, International Application No. PCT/US13/66298 (date of mailing Mar. 19, 2014).
US Office Action dated Nov. 28, 2016 in U.S. Appl. No. 14/060,176.
English translation of SIPO Office Action dated Jan. 17, 2017.
SIPO Office Action dated Dec. 27, 2016.
International Search Report dated Dec. 2, 2016 in Application No. PCT/US2016/037677.
Written Opinion dated Dec. 2, 2016 in Application No. PCT/US2016/037677.
US Office Action dated Jun. 9, 2016 in U.S. Appl. No. 14/060,176.
European Office Action dated Jun. 15, 2016.

* cited by examiner

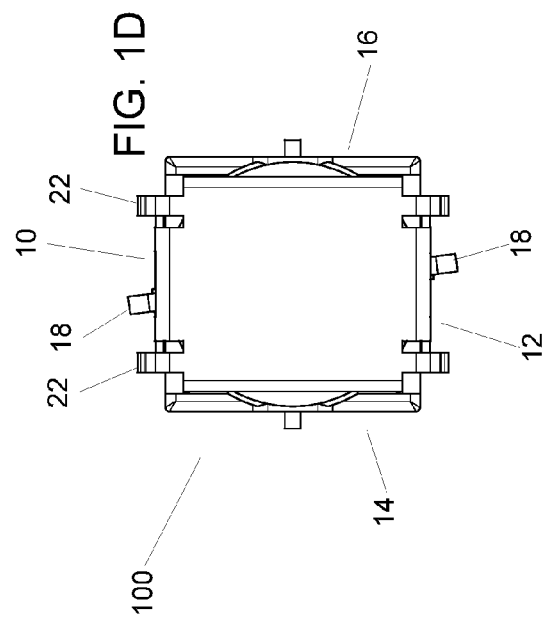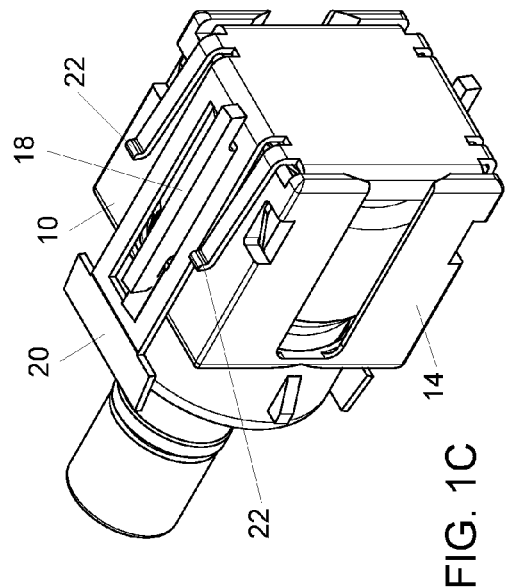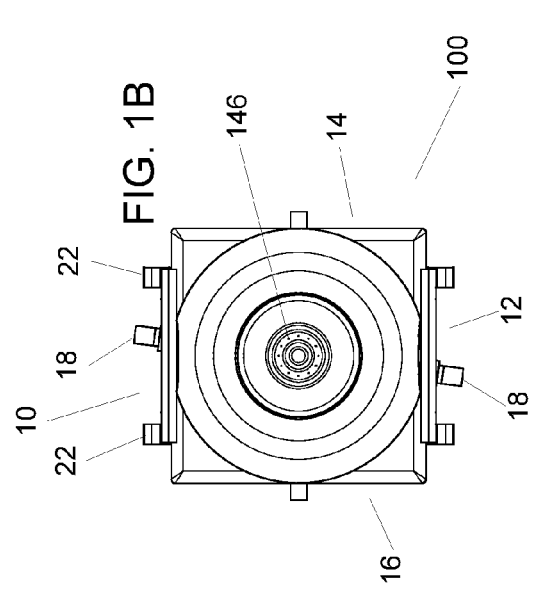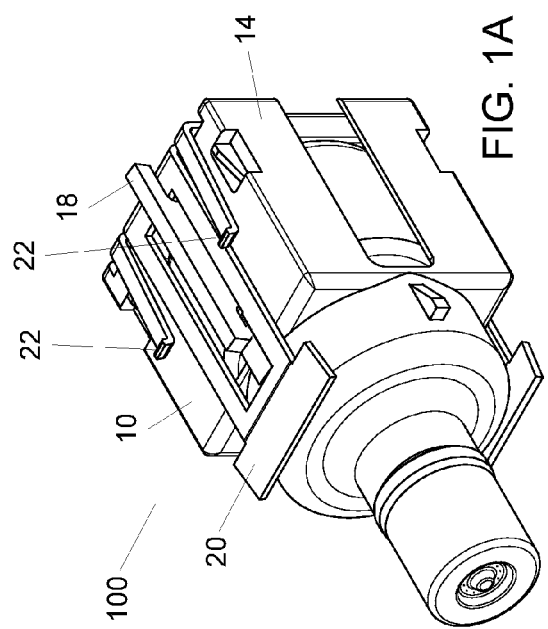

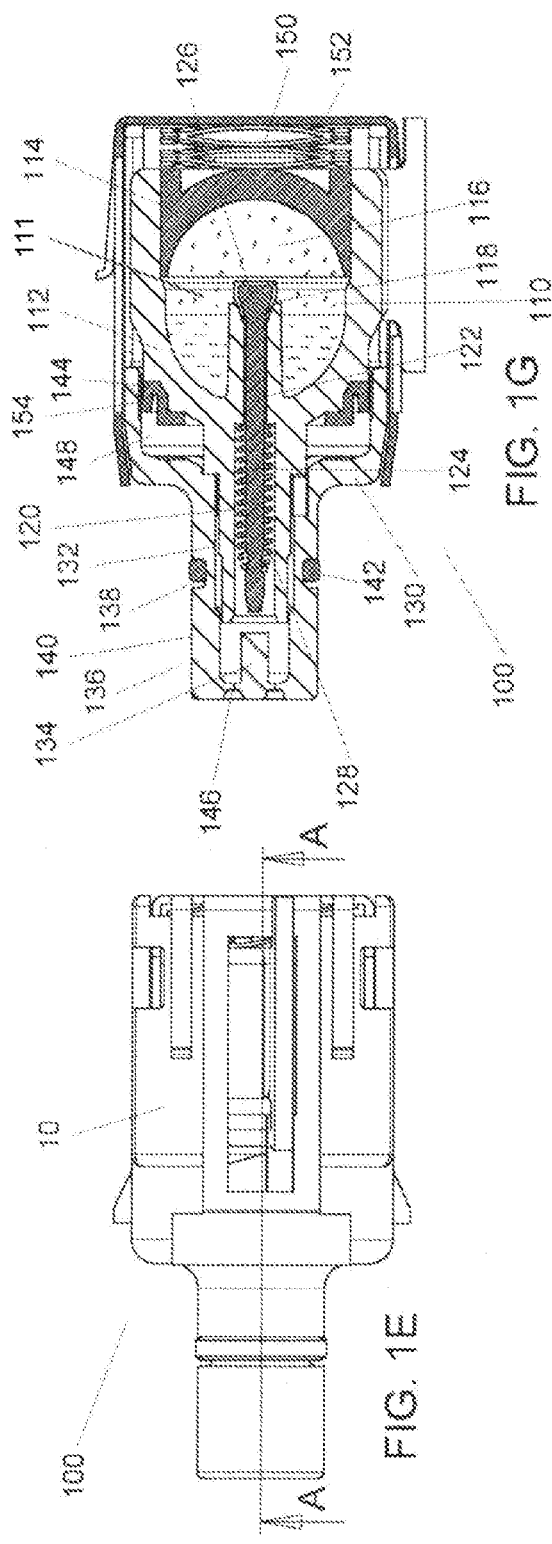
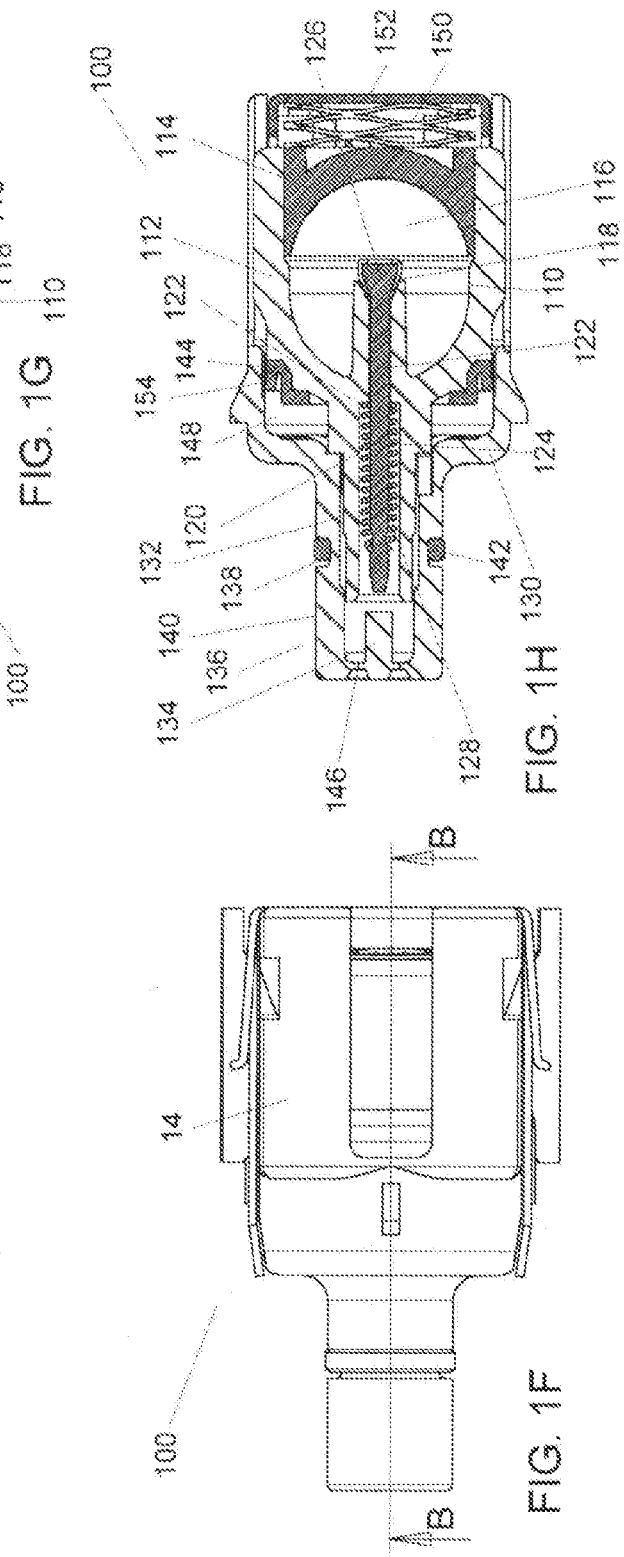

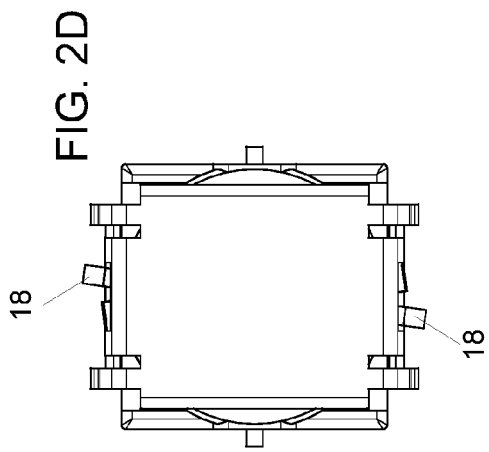
FIG. 2D
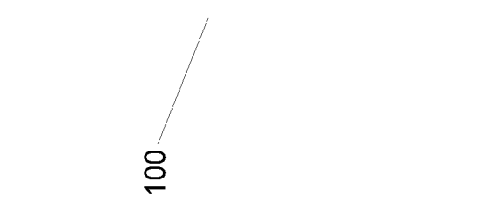
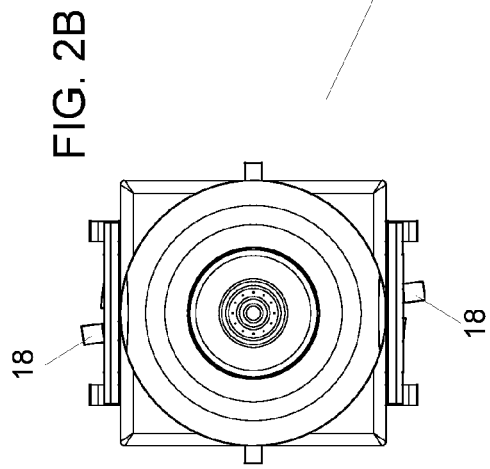
FIG. 2B
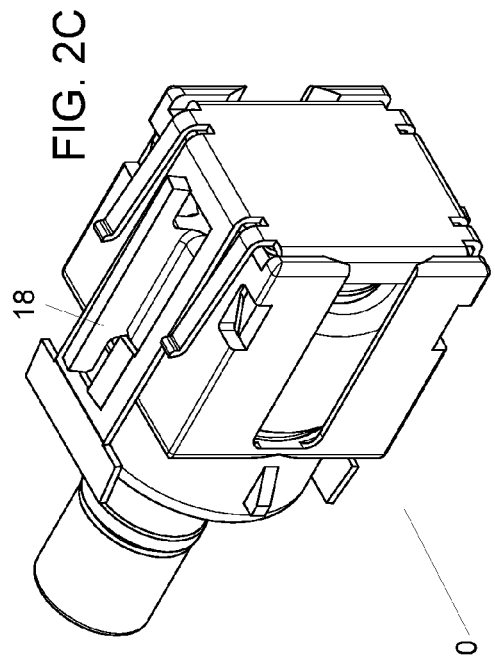
FIG. 2C
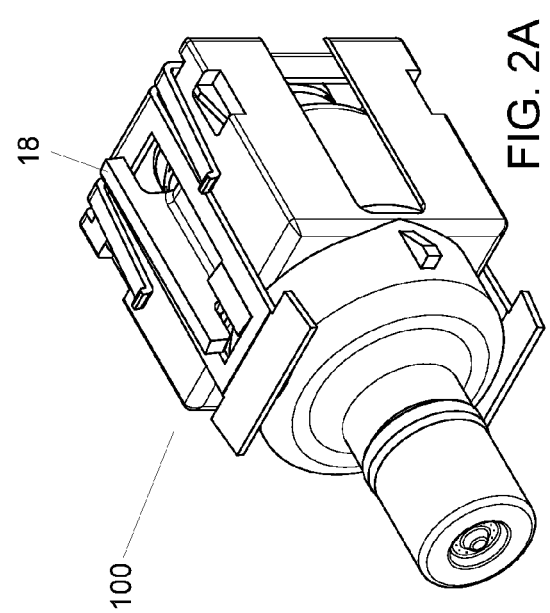
FIG. 2A

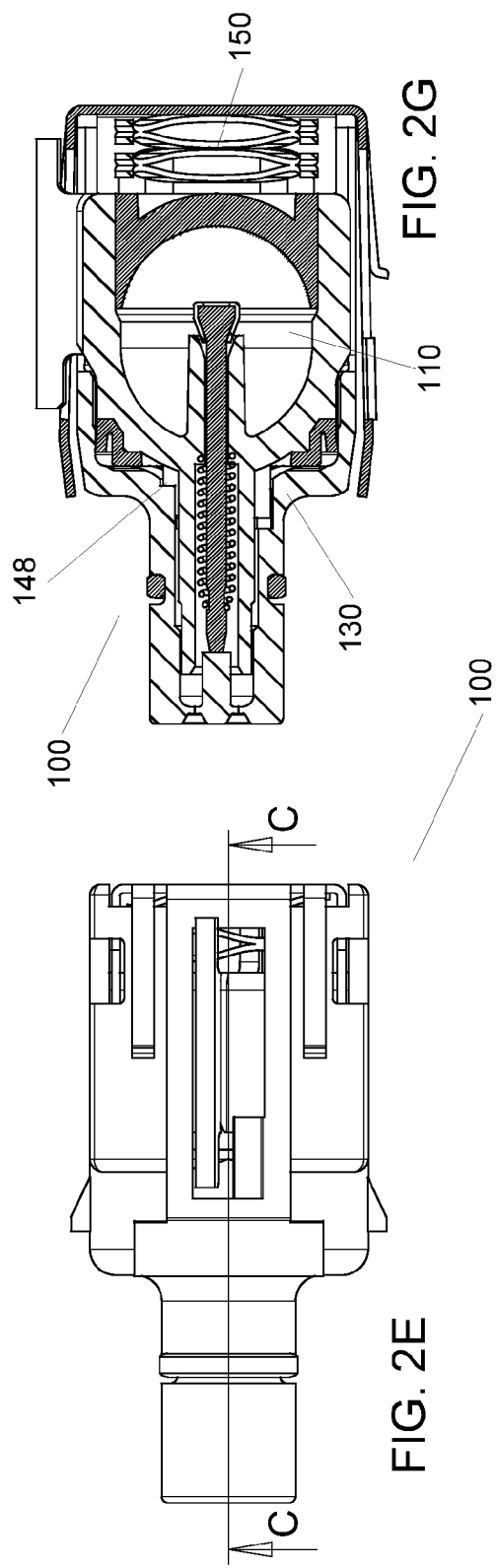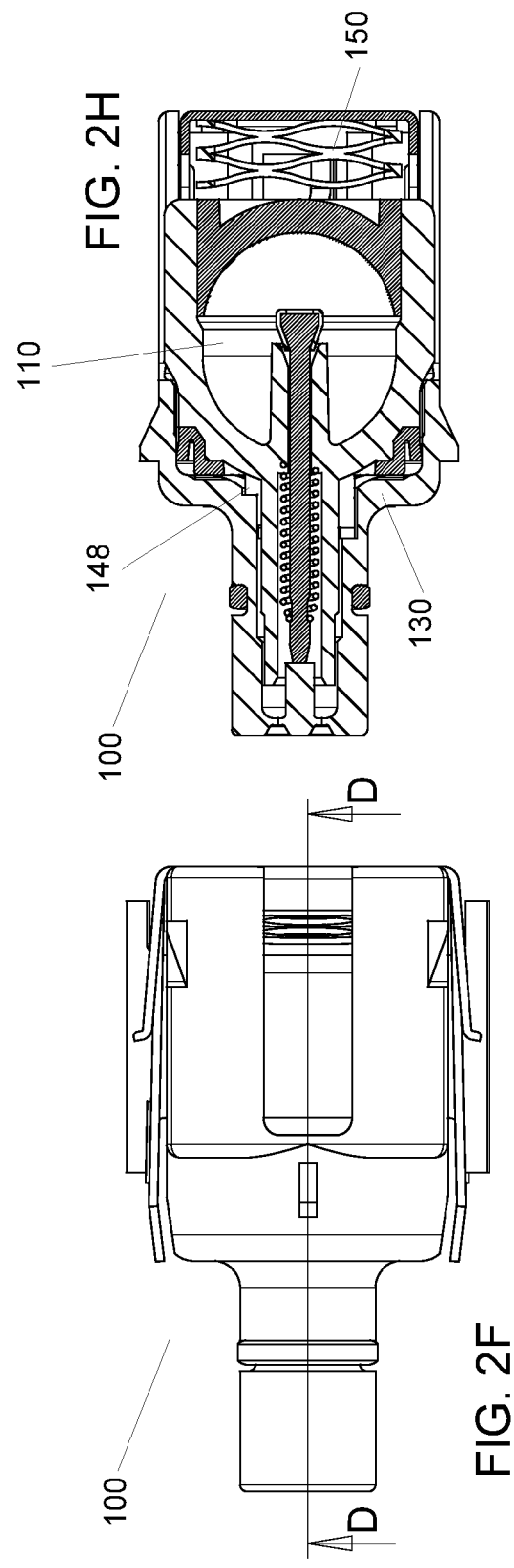

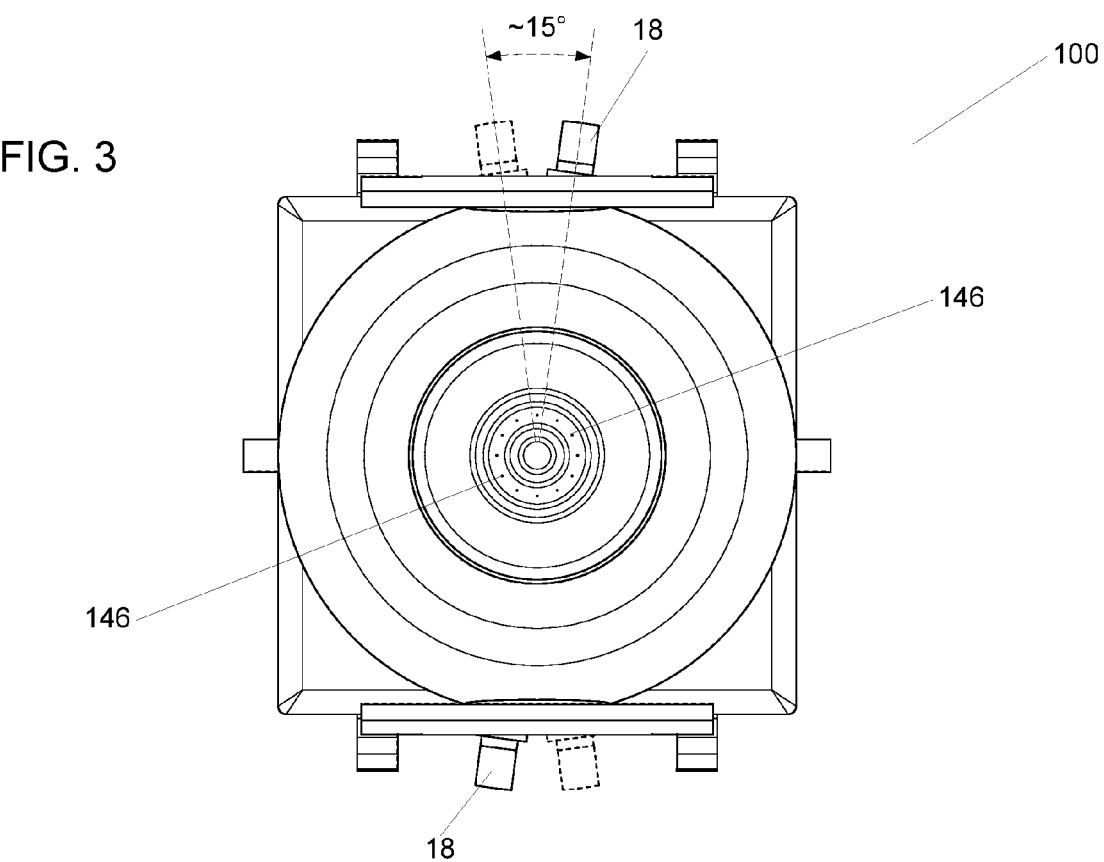

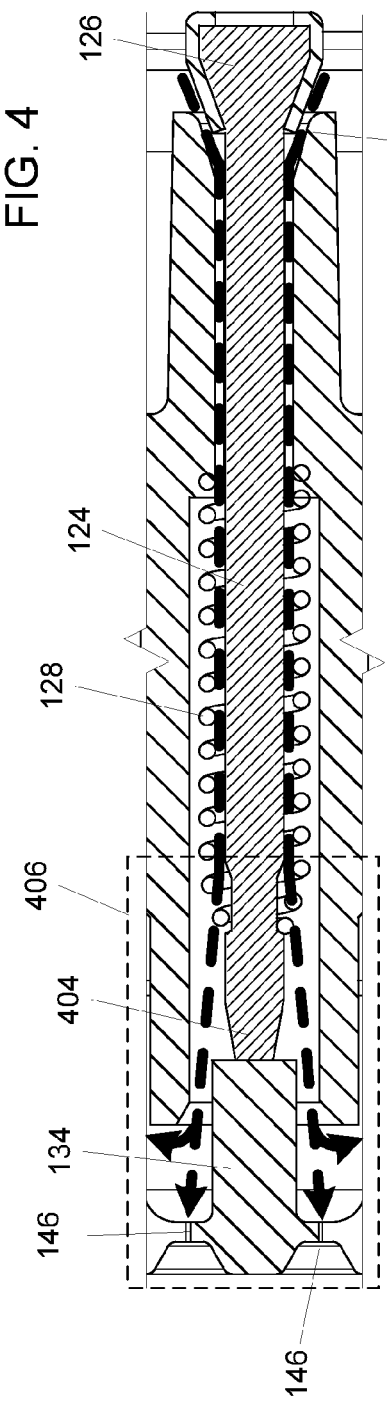
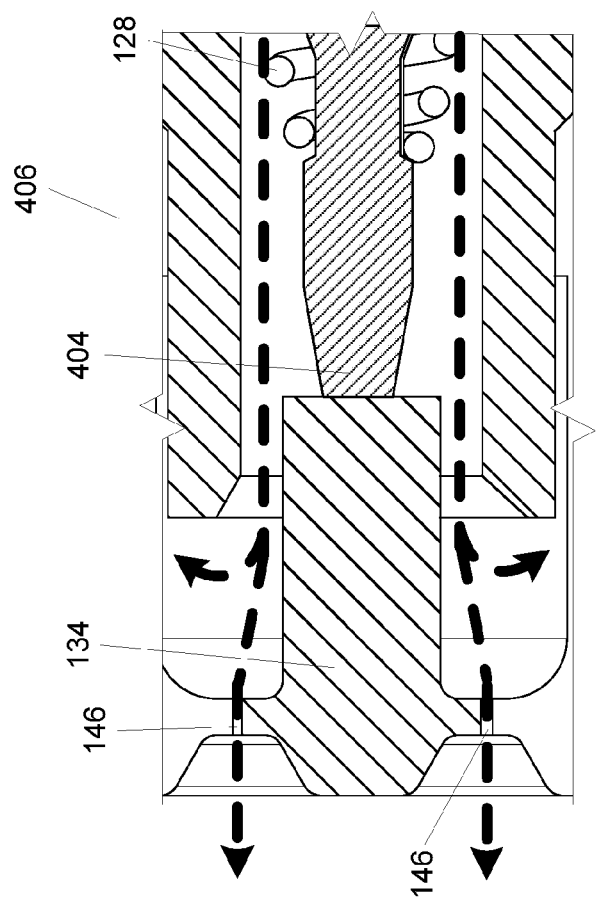
FIG. 4
FIG. 5

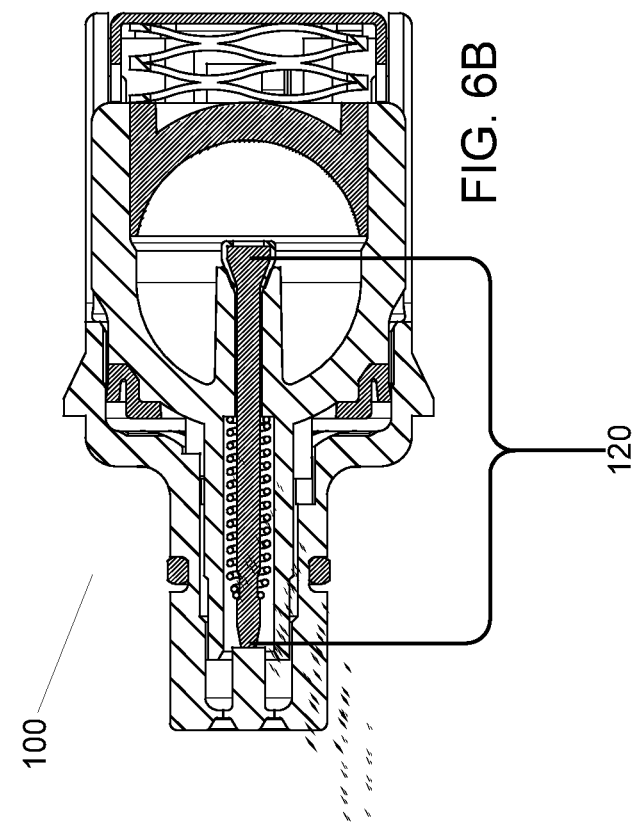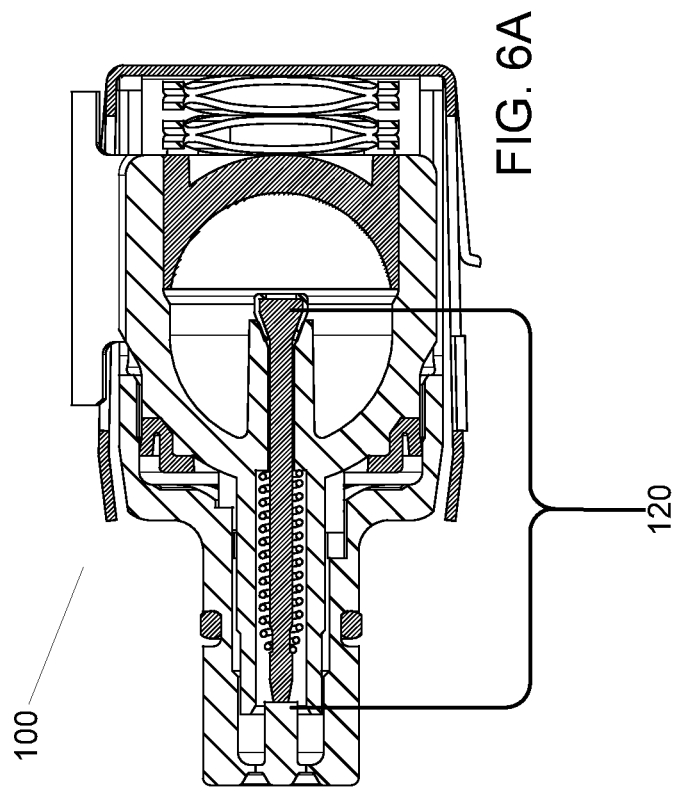

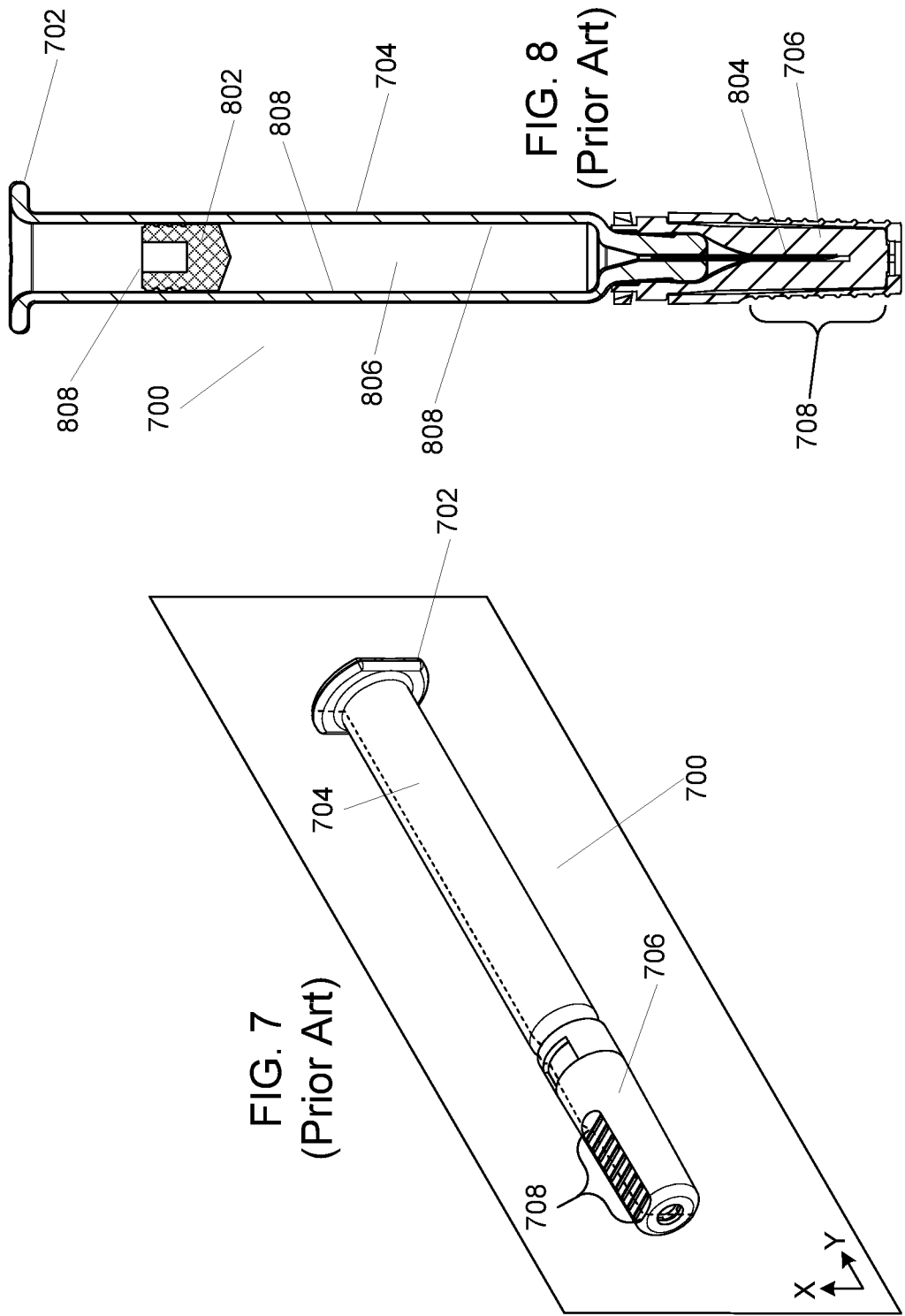

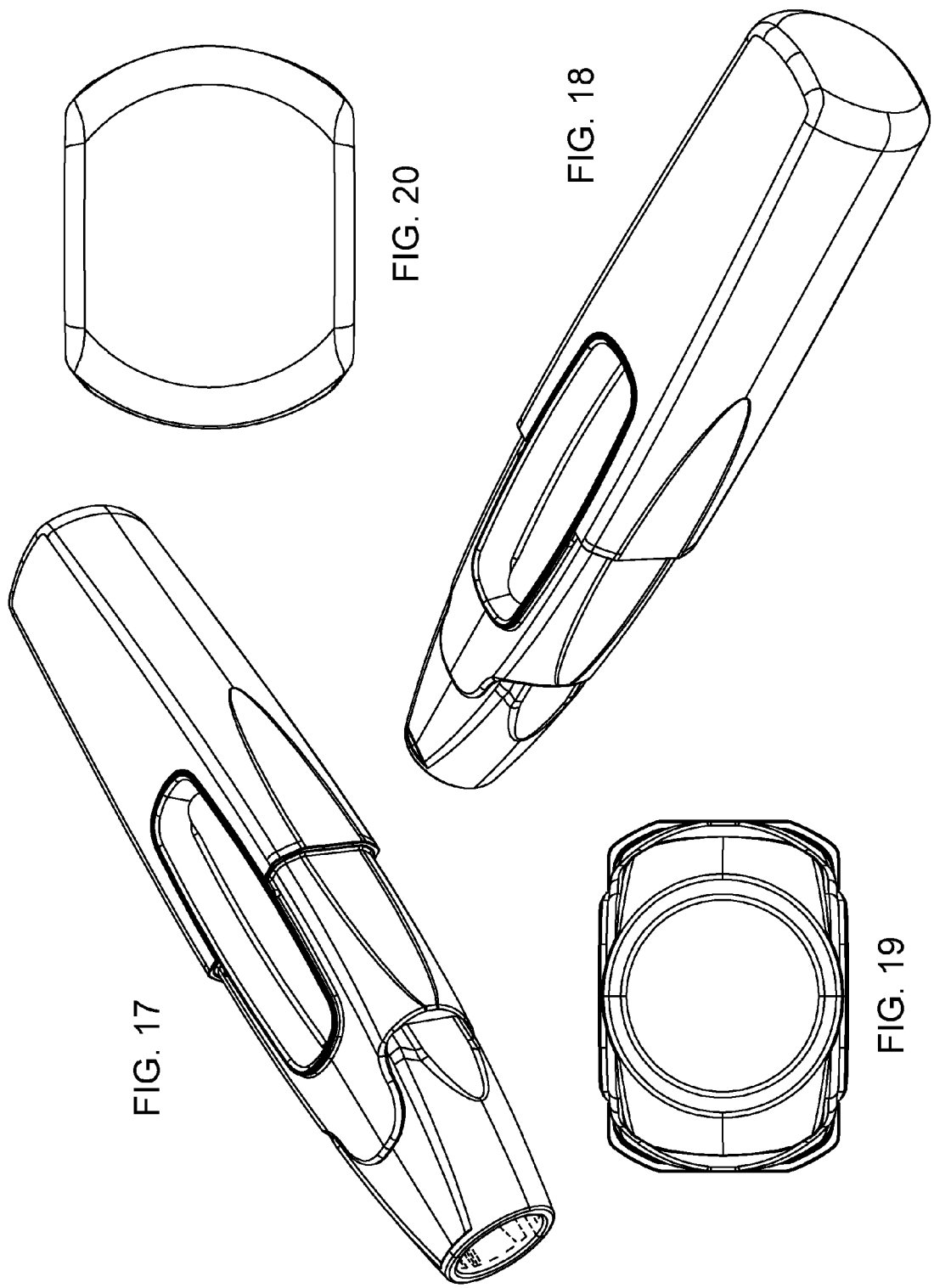

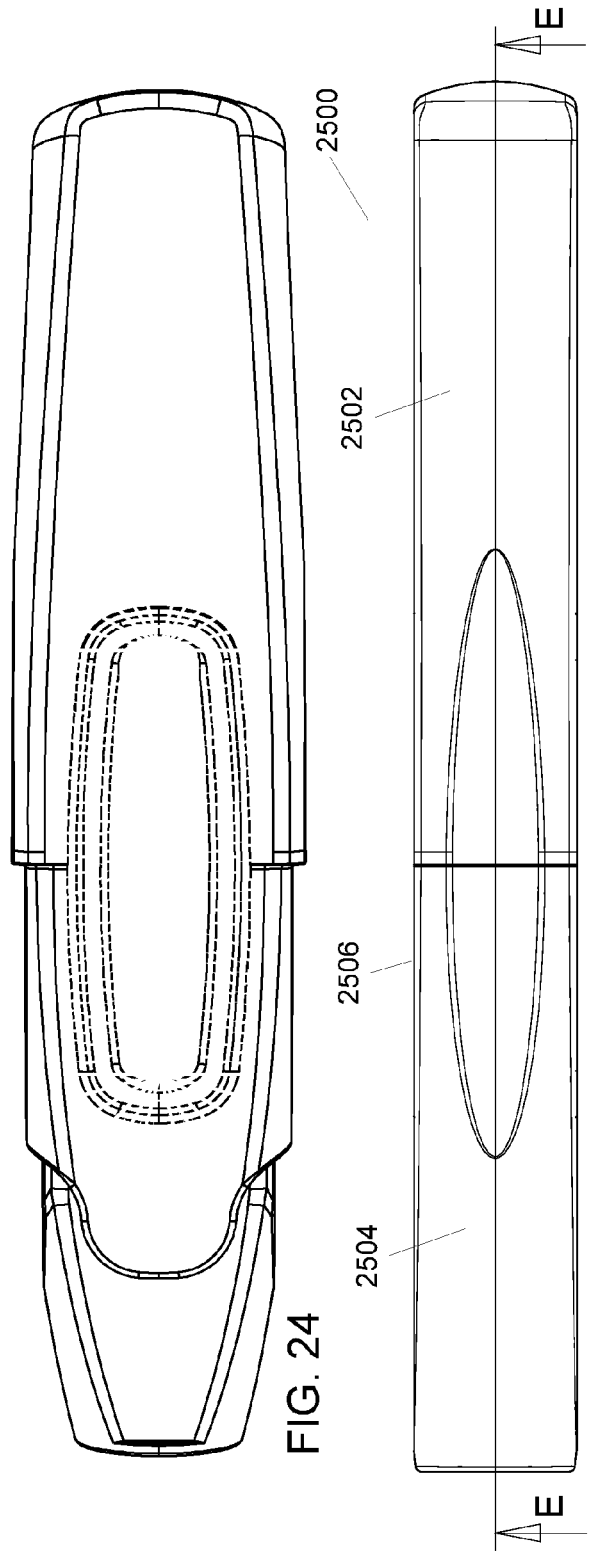
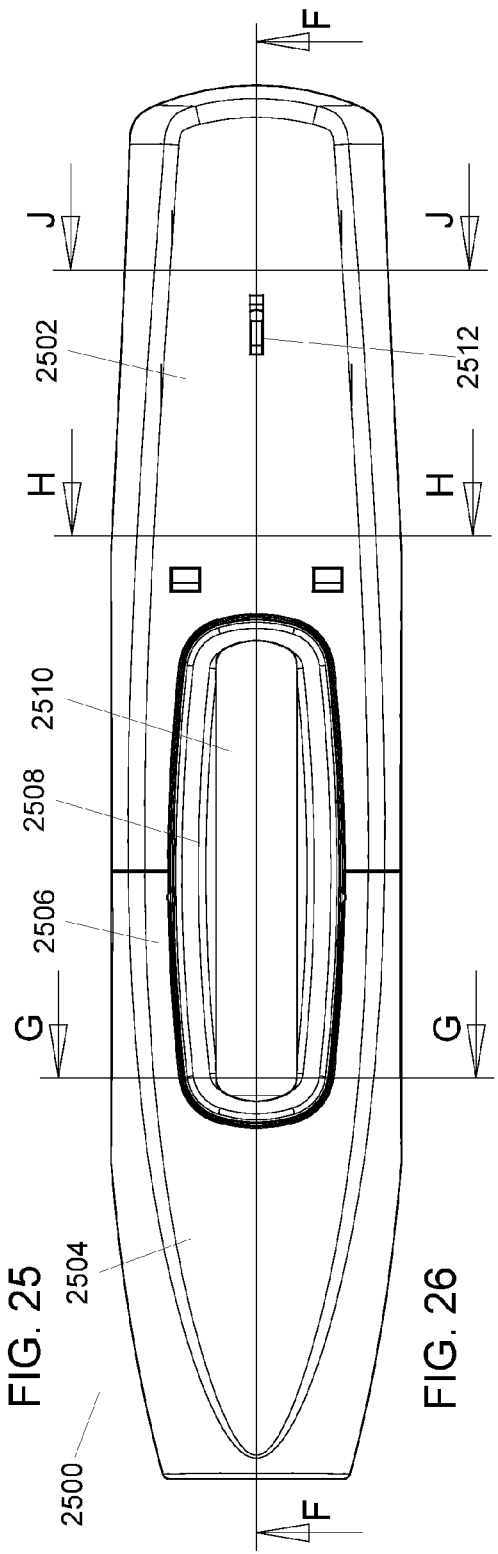
FIG. 24
FIG. 25
FIG. 26

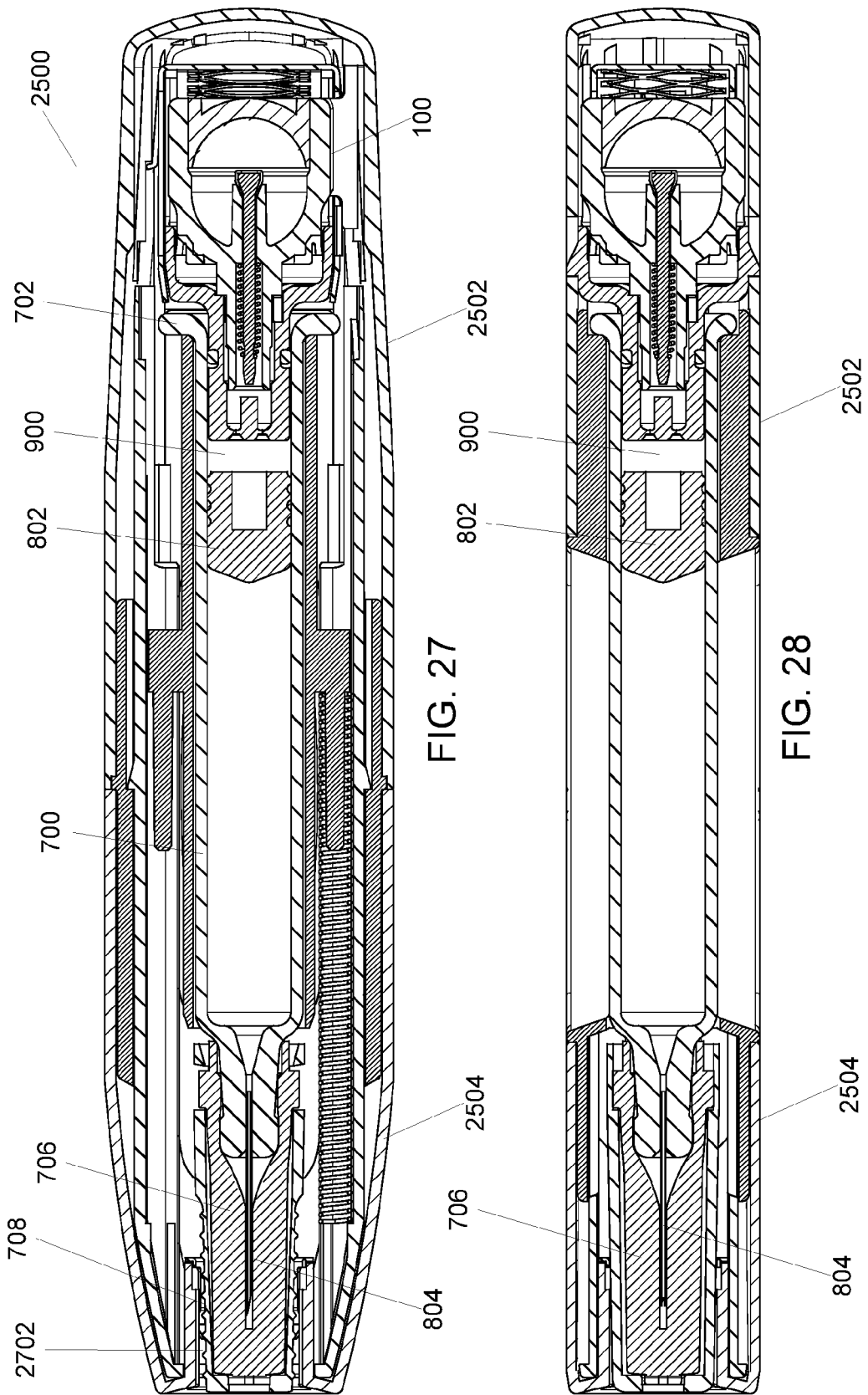

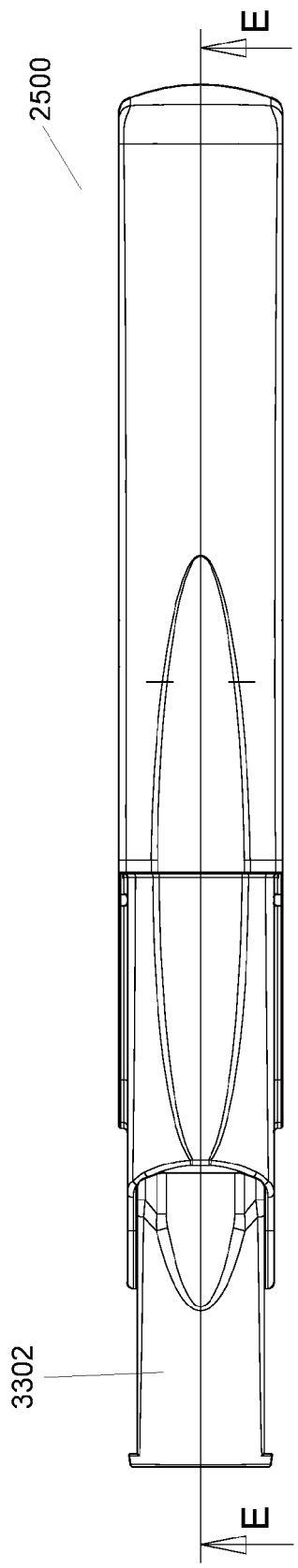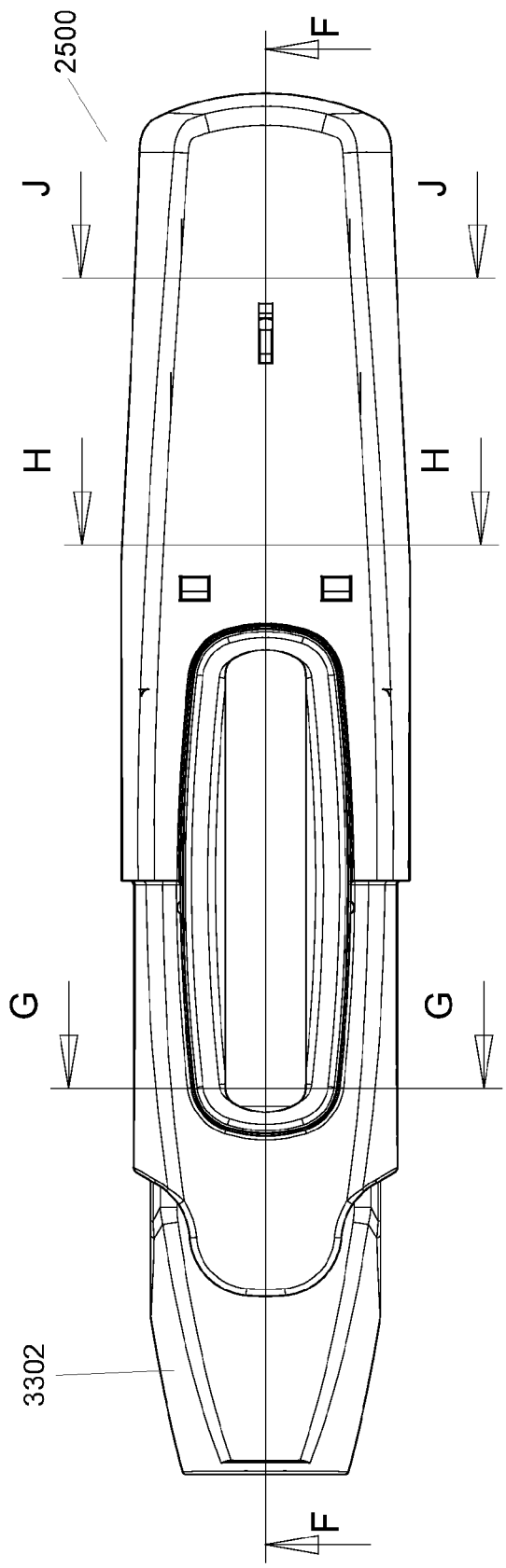

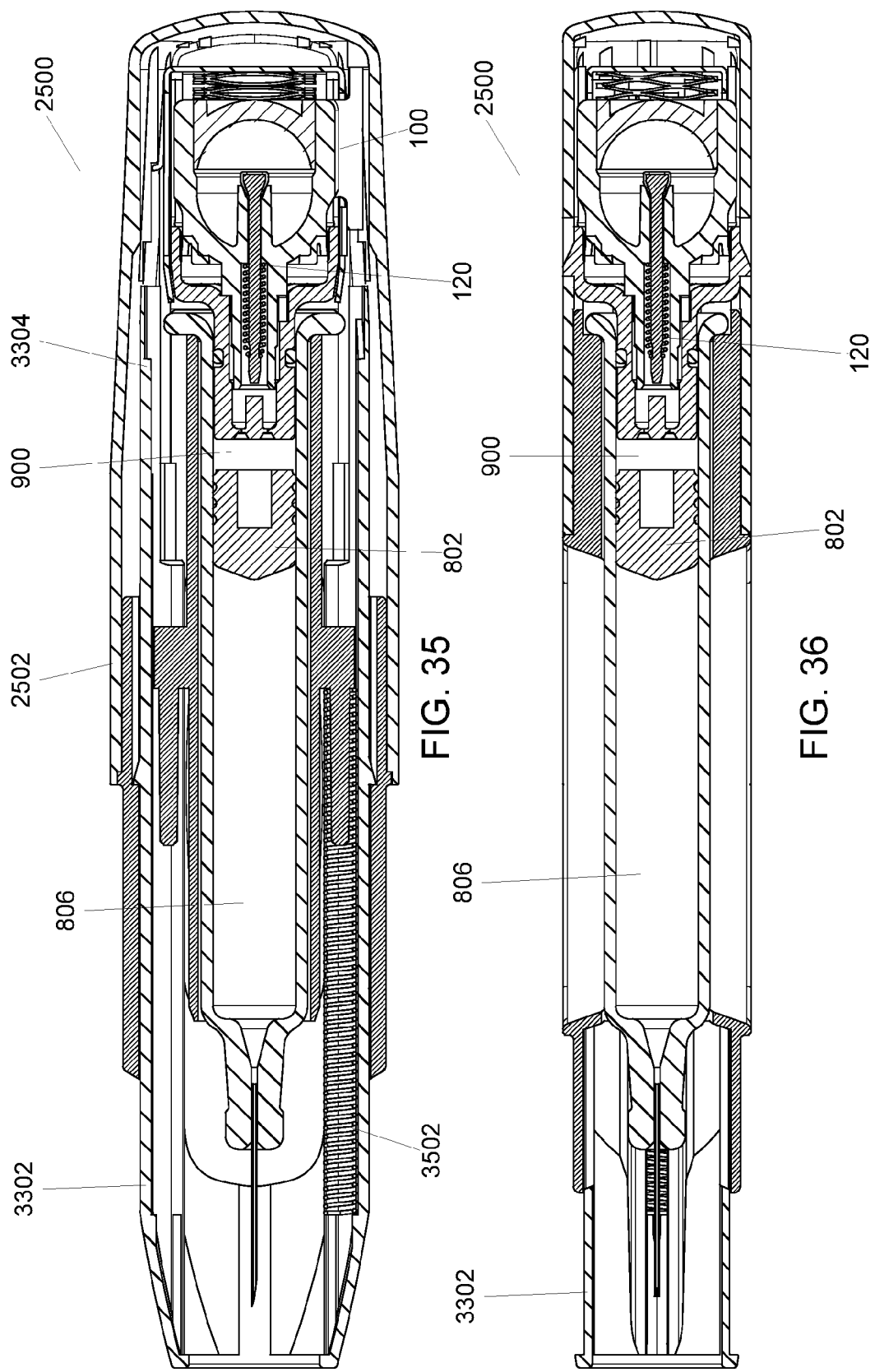

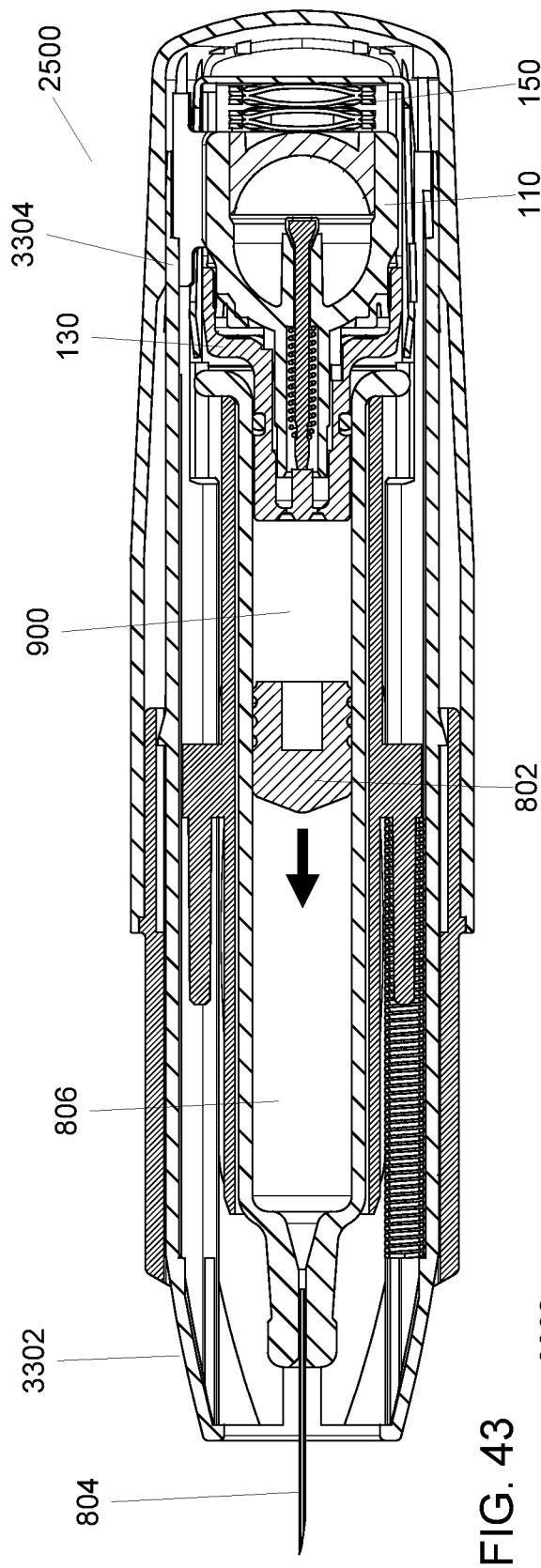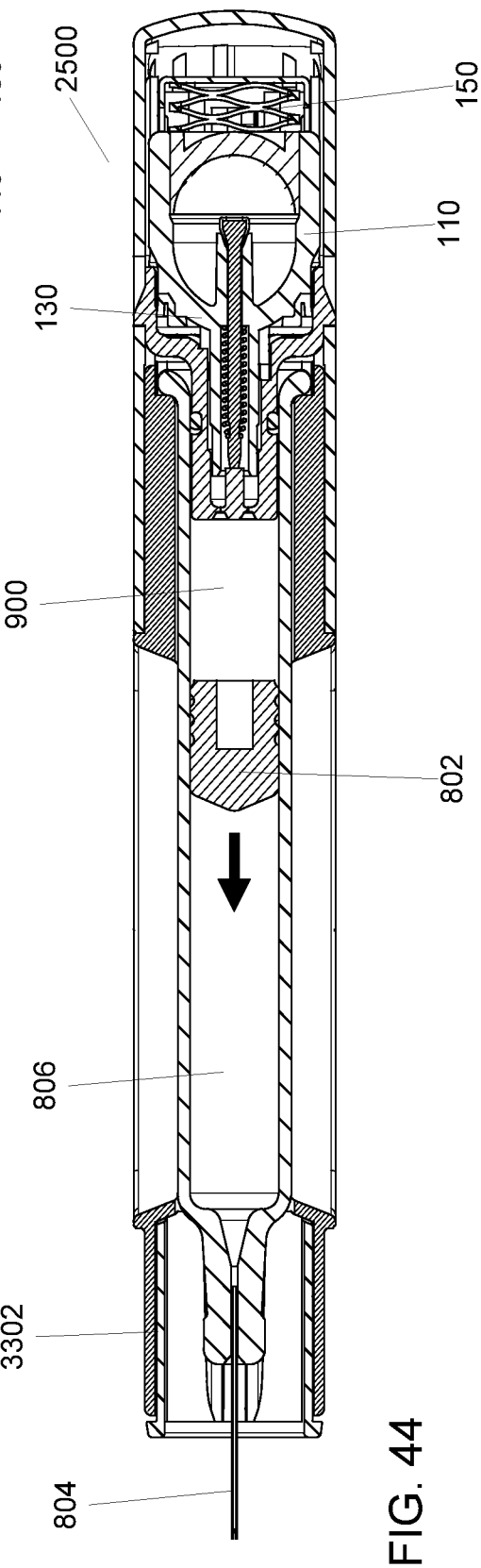
FIG. 43
FIG. 44

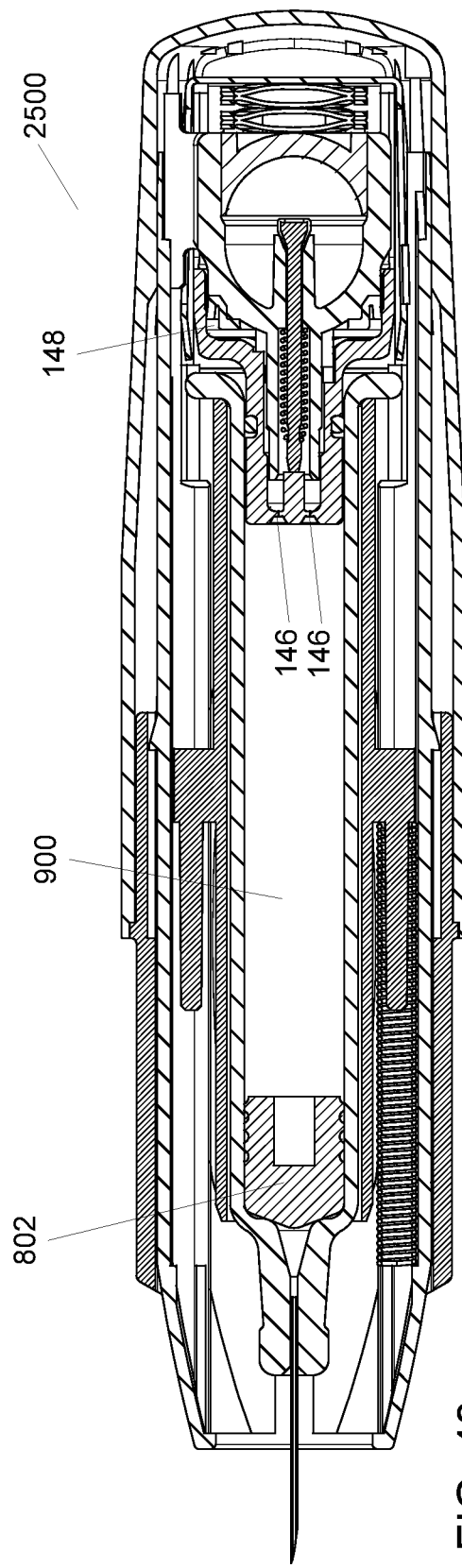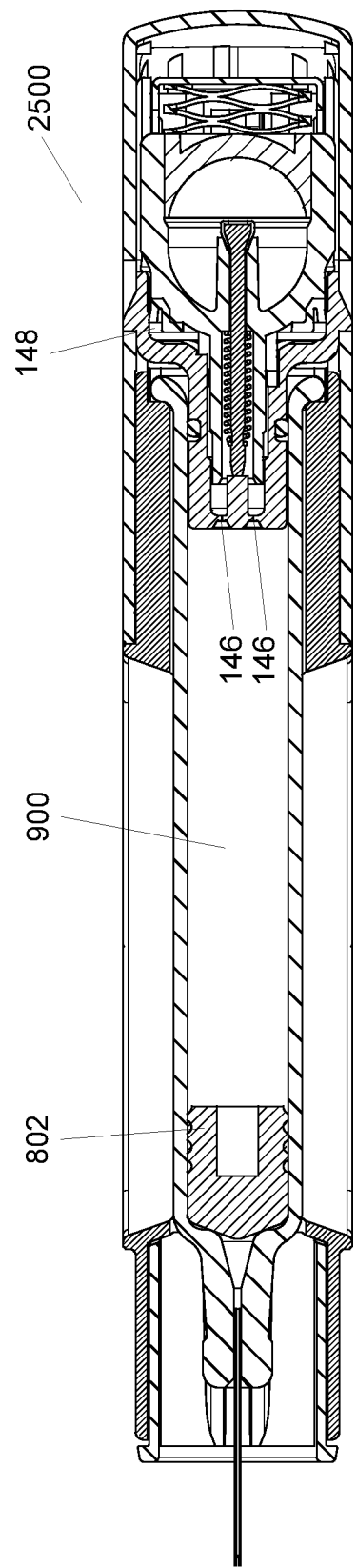
FIG. 49
FIG. 50

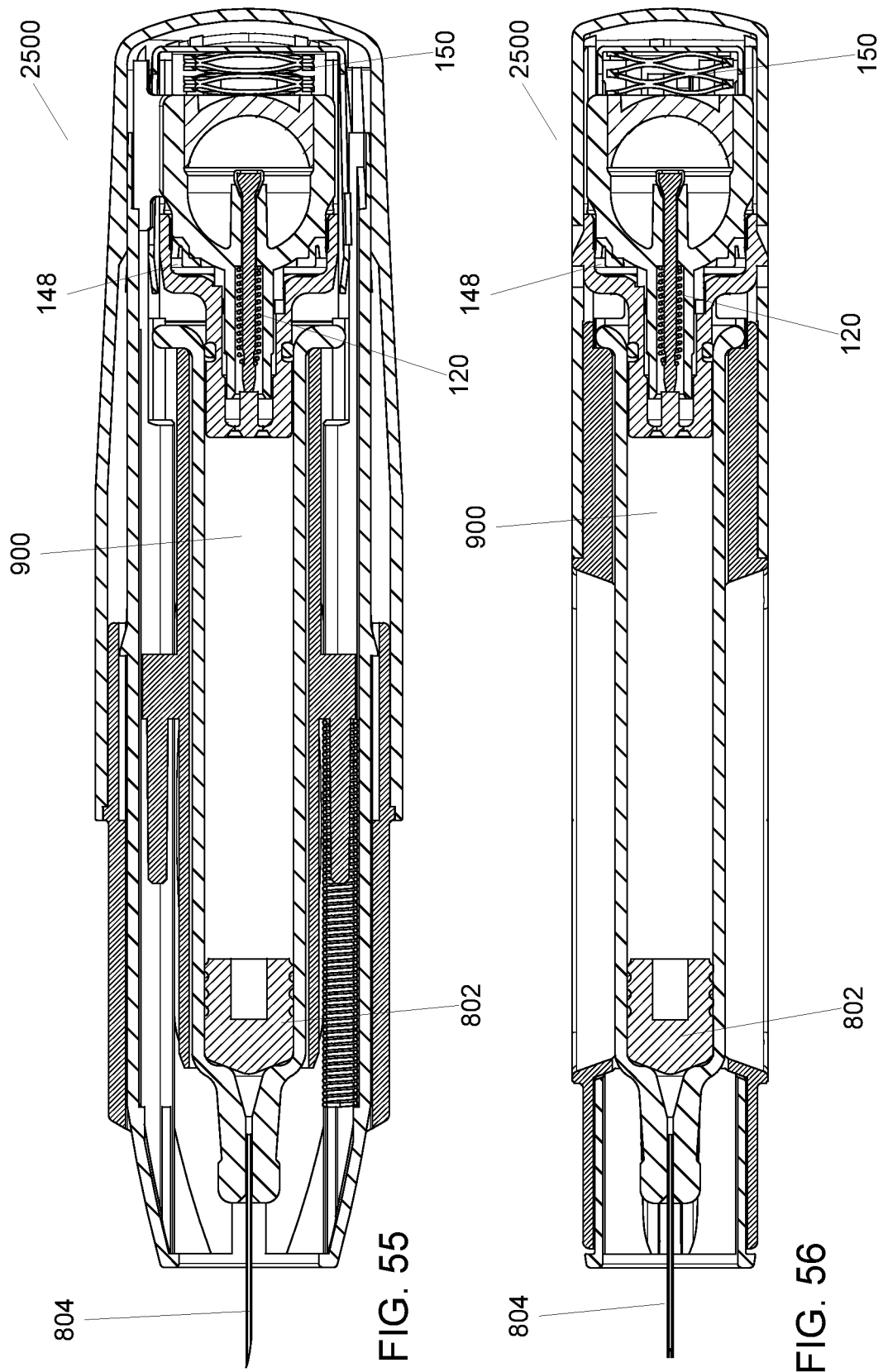

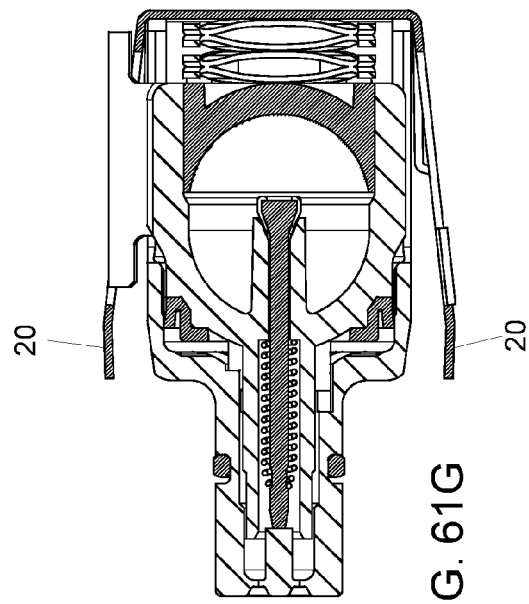
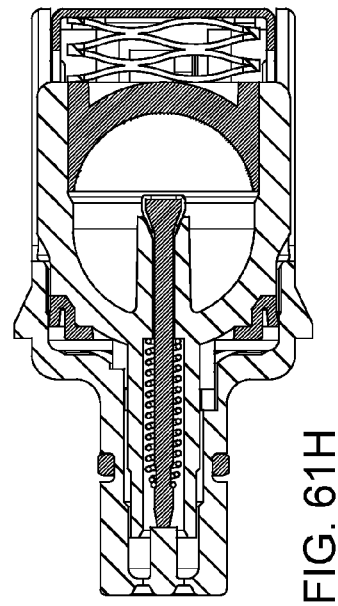
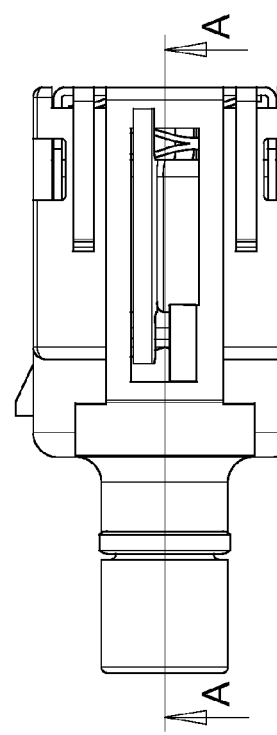
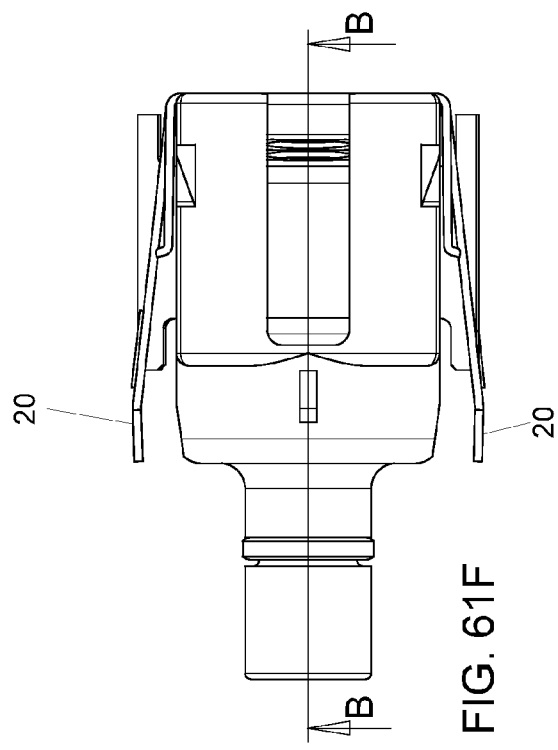
FIG. 61E
FIG. 61F
FIG. 61G
FIG. 61H

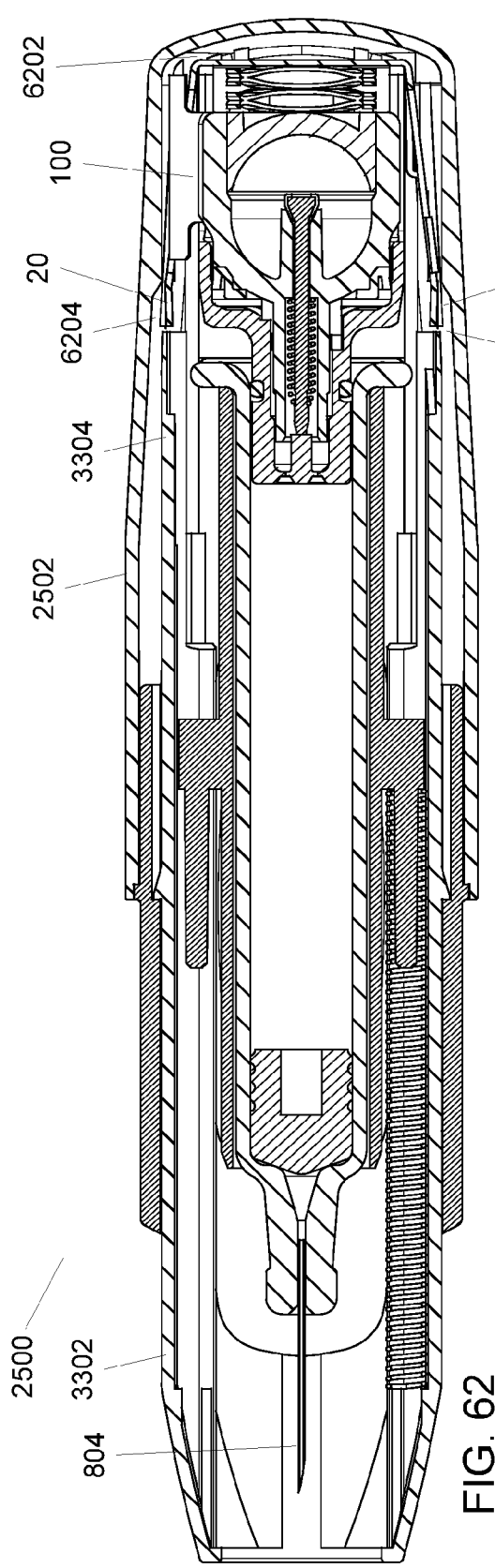
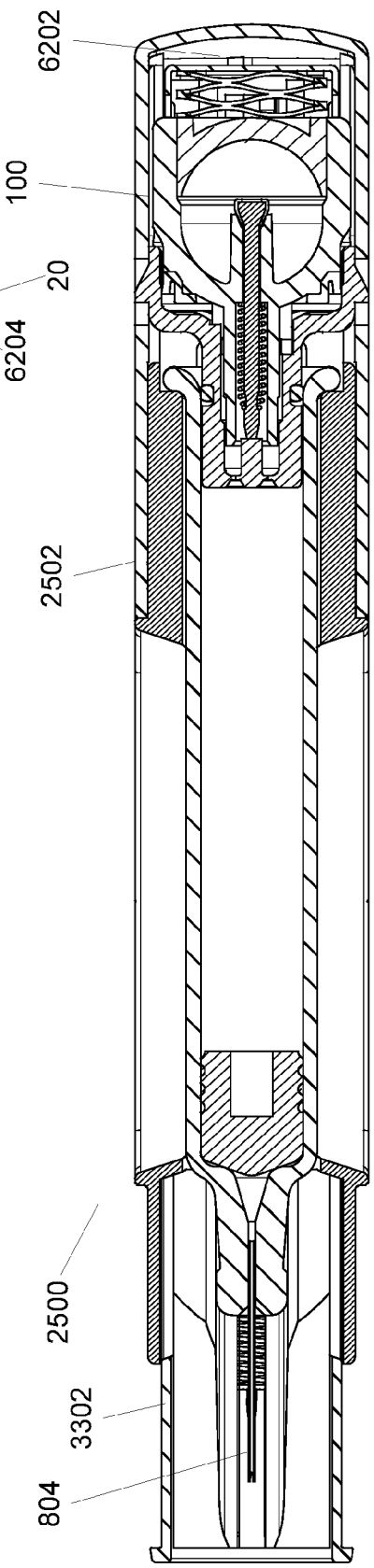
FIG. 62
FIG. 63

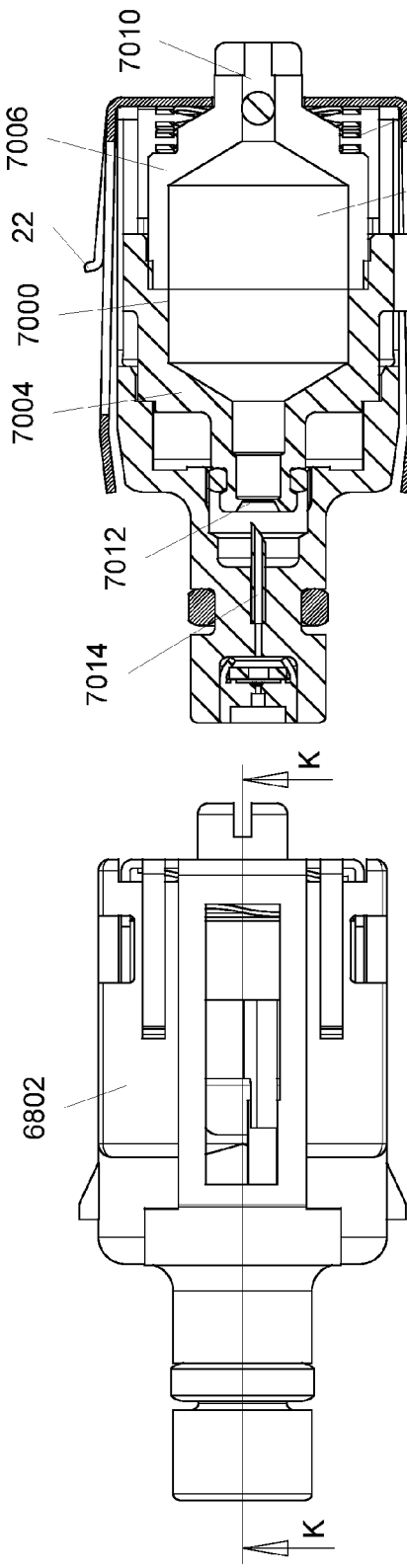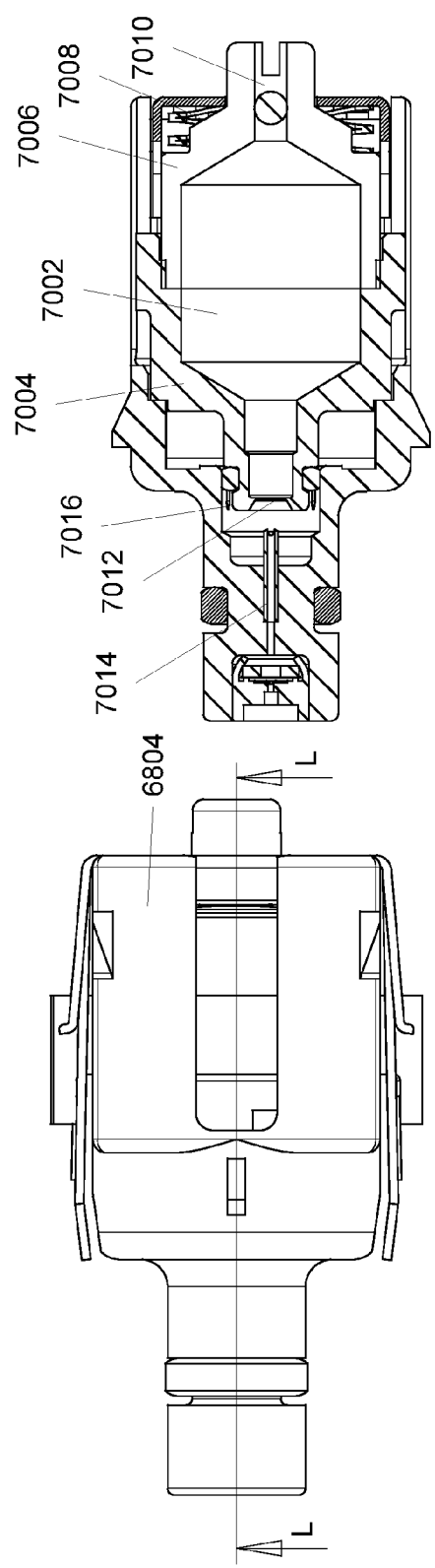

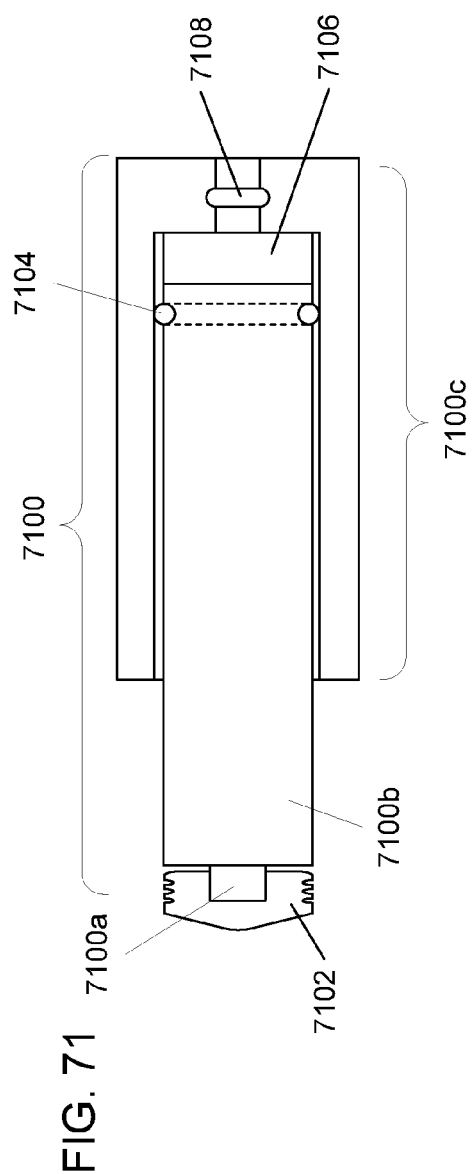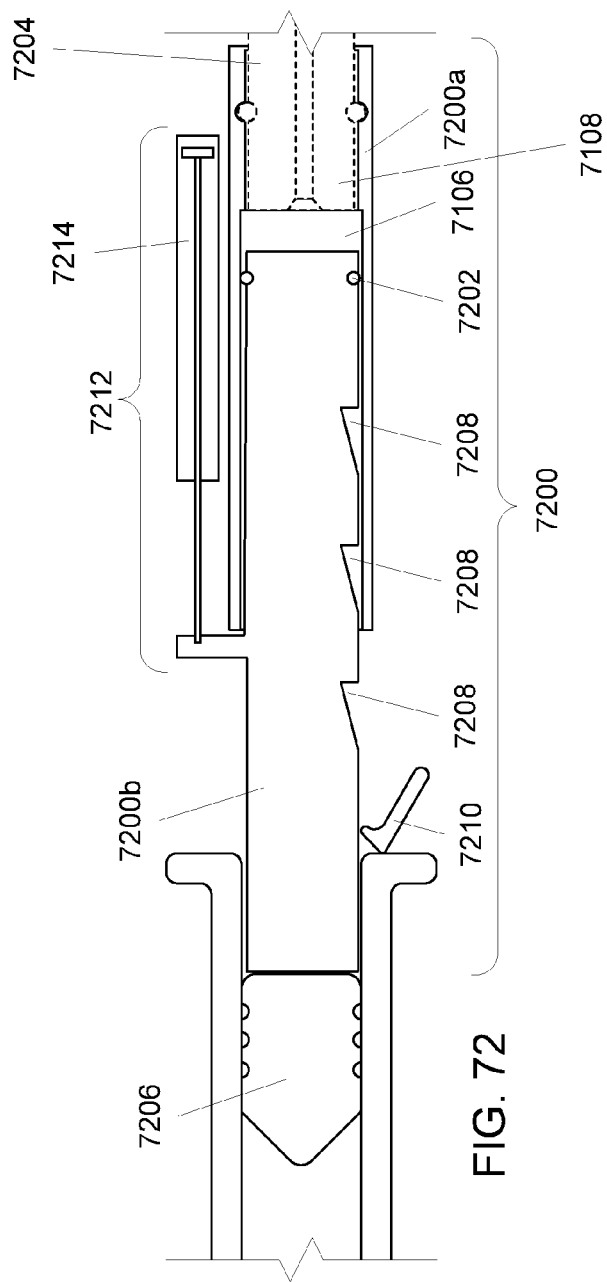
FIG. 71
FIG. 72

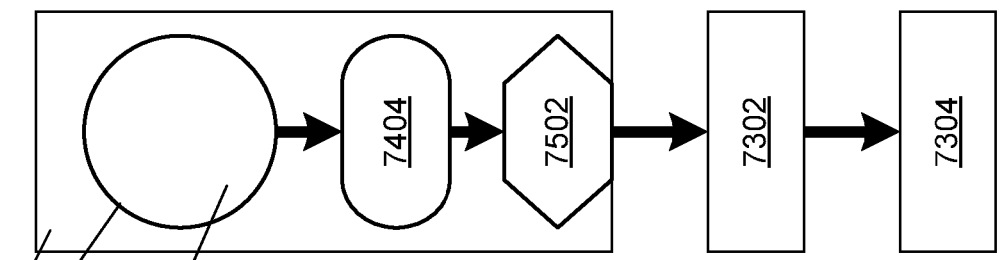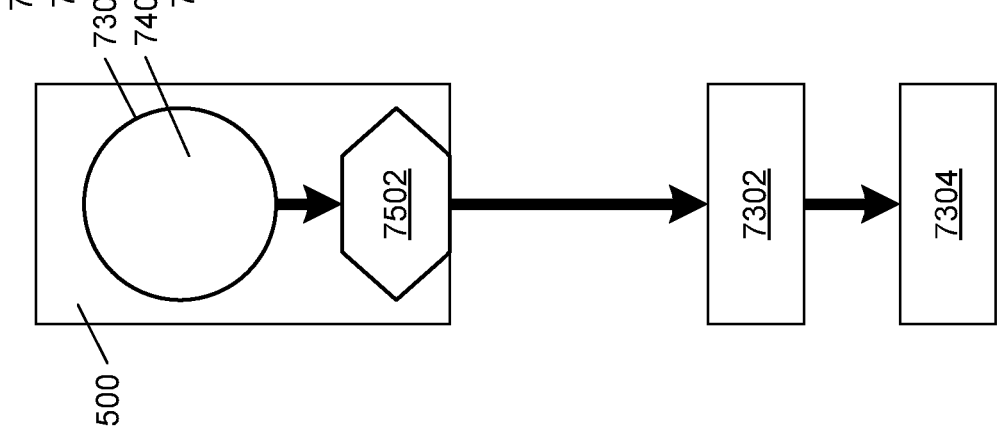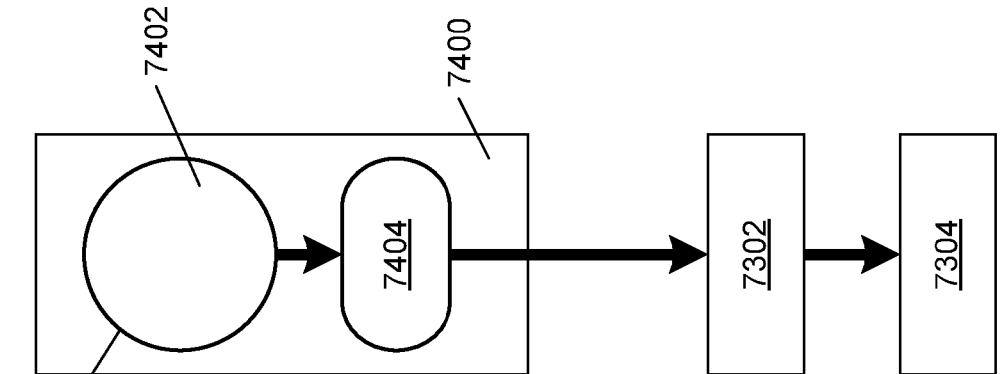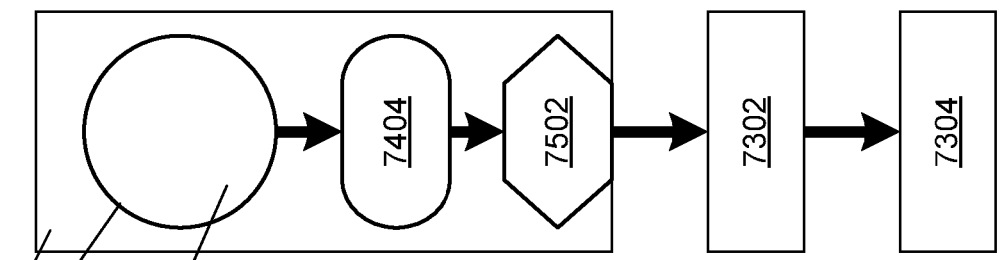

AUTOINJECTOR

CROSS-REFERENCE TO RELATED APPLICATION

This application claims the priority benefit of U.S. Provisional Patent Application No. 61/717,704, filed Oct. 24, 2012. The disclosures of which is incorporated by reference in its entirety as if fully set forth herein.

BACKGROUND

Field

This disclosure relates generally to drug delivery devices, and, more particularly, to delivering of a drug through a needle-based drug delivery device.

Background

An autoinjector is a medical device designed to deliver one or more doses of a particular drug in a manner that facilitates self-administration of the drug via a syringe needle. Autoinjectors were originally designed for military use to counteract nerve-agent poisonings. The devices later moved into the civilian realm, with the first civilian devices being introduced in the mid to late 1970s, to dispense epinephrine to treat anaphylaxis. More recently, these devices have seen broadened use.

By design, autoinjectors are easy to use and are intended for administration by patients to themselves, or by untrained personnel. Thus, they are typically self-contained and designed to require only a few basic steps to operate.

Typically, autoinjectors are spring actuated. This means that one or more springs are used to drive the drug through the needle of the autoinjector, and in some cases, to insert the needle into the patient as well. At least one spring is used to apply a force to the stopper of a syringe or cartridge, much in the manner that a person would manually actuate a syringe plunger, and drive the drug out of the syringe into the injection site. These autoinjectors typically deliver a full dose of their drug in about 5 to 10 seconds.

An alternative form of autoinjector is the gas jet injector, which dispenses with a needle entirely; instead using a high-pressure narrow jet of the drug itself to penetrate the skin. Gas jet injectors have predominantly been used for mass vaccinations, not single dose delivery, and involve delivery of the drug at pressures of about 4,000 psi almost instantaneously. Newer gas jet injectors use slightly lower pressures. In general however, gas jet injectors are limited in volume they can deliver in a single "shot" and the depth to which they can deliver the drug. In addition, as explosive/high impact technologies, they cause impact and jarring that can be problematic.

Current designs involve making tradeoffs among various controllable and uncontrollable factors to insure reliable, proper and complete dose delivery. However, the selected tradeoffs that provide for reliable, proper and complete dose delivery can result in the inability to provide certain desirable feature(s) or requiring of greater complexity to provide less than desirable version(s) of such feature(s).

BRIEF SUMMARY

Power packs employing the teachings herein have been developed for use with autoinjectors to overcome one or more of the foregoing problems, as well as to provide additional advantages.

One aspect of what has been developed involves a main body including a container, the container having a drug therein, a hollow needle coupled to the container; and a power source having a liquefied gas therein as a driver, a flow regulator, and at least one outlet through which some of the driver can exit the power source in a gaseous state, the power source body and container being coupled together such that, when an injection is initiated, driver will exit the power source via the at least one outlet under pressure and will apply an adaptively variable force to drive the drug from the container and out of the main body through the hollow needle while the flow regulator controls an exit flow rate such that the liquefied gas within the power source is maintained at substantially its vapor pressure.

Another aspect involves an autoinjector having a main body including a container, the container having a drug therein, a hollow needle coupled to the container through which the drug can be delivered; and a power source having a liquefied gas therein as a driver, a flow regulator, and at least one outlet through which some of the driver can exit the power source in a gaseous state, the power source and container being coupled together for operation such that, when an injection is initiated, the flow regulator will control an exit rate of the driver such that the liquefied gas in the power source is maintained at substantially its vapor pressure and the power source will apply a first force to deliver the drug via the hollow needle at a delivery rate that is a constant delivery rate, unless an obstruction force that causes the delivery of the drug to change to a reduced delivery rate occurs, and, when the obstruction force that causes the delivery of the drug to change to a reduced delivery rate occurs, the power source will apply an increased force in opposition to the obstruction force until the obstruction force is overcome and an increase in rate of drug delivery towards the constant delivery rate is achieved.

Yet a further aspect involves an autoinjector having a main body including a container, the container having a drug therein, a hollow needle coupled to the container through which the drug can be delivered; and a power source having a liquefied gas therein as a driver, a flow regulator, and at least one outlet through which some of the driver can exit the power source in a gaseous state, the power source and container being coupled together for operation such that, when an injection is initiated, the flow regulator will control an exit rate of the driver such that the liquefied gas in the power source is maintained at substantially its vapor pressure and the power source will apply a first force to deliver the drug via the hollow needle at a delivery rate that is a constant delivery rate, unless a reduced force opposing the first force is encountered such that the reduced opposing force causes the delivery of the drug to change to an increased delivery rate, and, when the reduced opposing force causes the delivery of the drug to change to the increased delivery rate, the power source will apply a force less than the first force until the increased delivery rate has reduced to the constant delivery rate.

The foregoing and following discussion outline, rather generally, the features and some technical advantages of one or more embodiments of this disclosure in order that the following detailed description may be better understood. Additional features and advantages of this disclosure will be described herein and may be the subject of claims of this or another application.

BRIEF DESCRIPTION OF THE DRAWINGS

This disclosure is further described in the detailed description that follows, with reference to the drawings, in which:

FIGS. 1A through 1H respectively illustrate, in simplified form, different exterior views of one example of a representative inventive power pack embodying the instant innovations;

FIGS. 2A through 2D show the power pack of FIGS. 1A through 1D upon entering the "activating" state;

FIGS. 2E and 2F show the upper face and right face of the power pack when it is in the "activating" state;

FIG. 2G is a cross sectional view of the power pack taken along C-C of FIG. 2E;

FIG. 2H is a cross sectional view of the power pack taken along D-D of FIG. 2F;

FIG. 3 shows the positions of the wings on the canister in the initial position and the activating position;

FIG. 4 is an enlargement of the central portion of FIG. 2G;

FIG. 5 is a further enlargement of part of FIG. 4;

FIG. 6A is a cross sectional view of the power pack taken along C-C of FIG. 2E;

FIG. 6B is a cross sectional view of the power pack taken along D-D of FIG. 2F;

FIG. 7 is a simplified view of an example conventional syringe configuration with which power packs as described herein may be used;

FIG. 8 is a cross-sectional view of the syringe of FIG. 7 taken through the center in the X-Y plane;

FIG. 17 is a front perspective view of an alternative design for an autoinjector implementation;

FIG. 18 is a rear perspective view of the alternative design for the autoinjector implementation of FIG. 17;

FIG. 19 is an enlarged front elevational view of the alternative design for the autoinjector implementation of FIG. 17;

FIG. 20 is an enlarged rear elevational view of the alternative design for the autoinjector implementation of FIG. 17;

FIG. 24 is an alternative bottom plan view of the alternative design for the autoinjector implementation of FIG. 17;

FIG. 25 is a right side plan view of another example variant autoinjector;

FIG. 26 is a top plan view of the variant autoinjector of FIG. 25;

FIG. 27 is a cross sectional view of the variant autoinjector taken along E-E of FIG. 25;

FIG. 28 is a cross sectional view of the variant autoinjector taken along F-F of FIG. 26;

FIG. 33 is a right side elevational view of the autoinjector of FIG. 25;

FIG. 34 is a top plan view of the autoinjector of FIG. 33;

FIG. 35 is a cross sectional view of the variant autoinjector taken along E-E of FIG. 33;

FIG. 36 is a cross sectional view of the variant autoinjector taken along F-F of FIG. 34;

FIG. 43 is a cross sectional view of the variant autoinjector taken along E-E of FIG. 41;

FIG. 44 is a cross sectional view of the variant autoinjector taken along F-F of FIG. 42;

FIGS. 49 and 50 are cross sections showing the autoinjector at the point where the full dose has been delivered;

FIGS. 55 and 56 are cross sections showing the autoinjector after the end of dose indicator has been given;

FIGS. 61A-61H illustrate the power pack of FIGS. 1A-1H when the feature is in the "uncompressed" or "released" state;

FIGS. 62 and 63 are cross sections of the autoinjector respectively taken along E-E of FIG. 33 and F-F of FIG. 34 in this final state;

FIGS. 70A and 70B respectively show the upper face and right face of an example power pack implementation in its initial state;

FIG. 70C is a cross sectional view of the power pack taken along K-K of FIG. 70A;

FIG. 70D is a cross sectional view of the power pack 6800 taken along L-L of FIG. 70B;

FIG. 71 illustrates, in simplified form, one example of an intermediate member;

FIG. 72 illustrates, in simplified form, an alternative example intermediate member;

FIGS. 73-76 illustrate, in the most generic form, several power pack approach variants.

DETAILED DESCRIPTION

Figure 9:
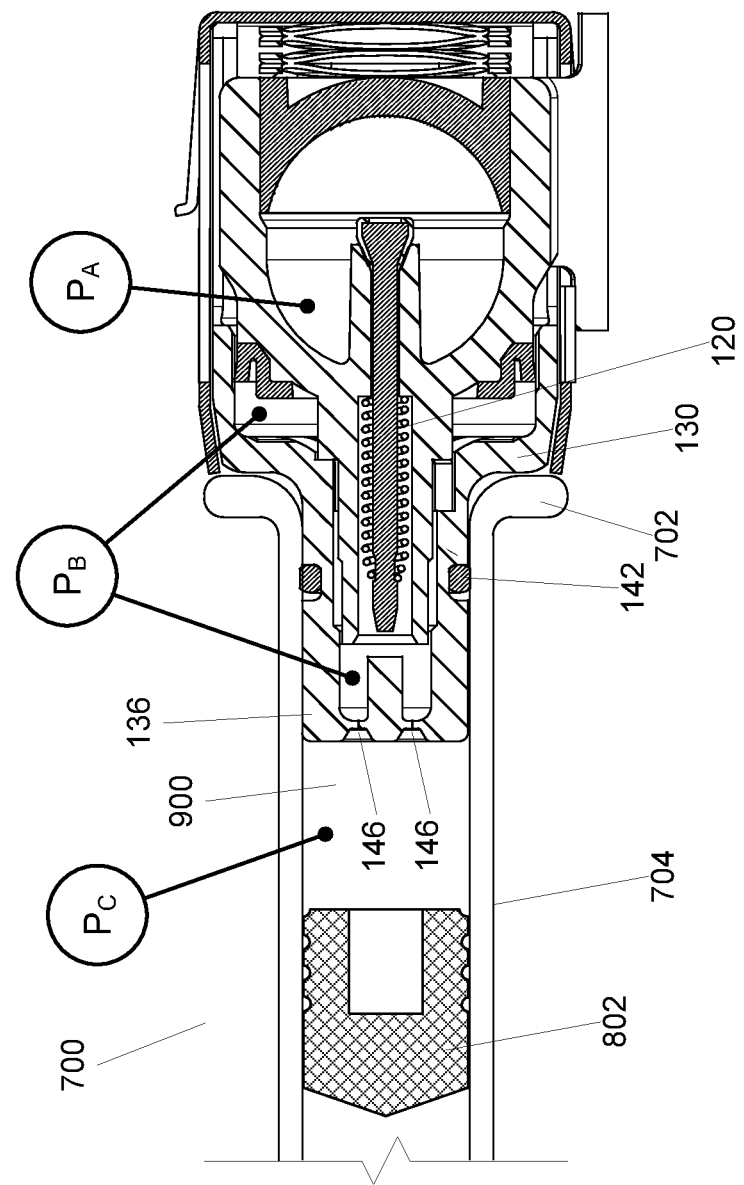
FIG. 9 illustrates, in simplified form, the combination of a portion of the cross section of the syringe of FIG. 7 and the power pack (cross section of FIG. 1E) as the syringe and power pack would be used together.

In simplified overview, a constant pressure source power pack has been designed for use in conjunction with a needle-based drug dose delivery device, for example, an autoinjector, infuser, pump, pen, etc., that provides significant advantages, particularly over the foregoing approaches. This power pack uses a reservoir of a driver (e.g. propellant, or compressed or liquefied gas) that acts as a constant pressure source and is used to apply a force to a component of the delivery device, for example, a stopper, rod, the drug container or other member, in a controlled manner, to thereby deliver the dose of drug from the container via a hollow needle (i.e. an injection). Notably, some power pack variants designed using the principles described herein can deliver the drug in a more controllable way than is done with conventional autoinjectors while accommodating manufacturing variabilities that can affect the force required to deliver the dose. For example, some power pack variants designed using the principles described herein can more easily overcome variances in syringe wall siliconization or "sticking" resulting from a longer shelf life before use that can impede smooth and continuous stopper movement during use. Still further, power pack variants designed using the principles described herein can readily be constructed to accommodate different viscosity drugs or combinational drugs that must be mixed immediately prior to use.

Moreover, power pack variants designed using the principles described herein can easily be provided as self-contained units, separate and apart from an autoinjector body and syringe. In this manner, replacement of the syringe and power pack can allow an autoinjector body to be reused, thereby reducing waste and cost. Alternatively, autoinjectors can be constructed that can contain, as an integral part, a power pack constructed in accordance with the teachings herein. Irrespective of whether they are removable or integral, such power packs can be deployed in autoinjectors of varying ornamental designs without departing from the teachings herein.

In addition, irrespective of the internals of the autoinjectors described herein, different ornamental designs for an autoinjector can be created as shown or described herein as can various specific components thereof.

For ease of explanation, as used herein, the term "syringe" is intended mean any combination of a drug-containing container, a hypodermic needle and a pathway between the two through which the drug can be delivered from the container into a living body via the hypodermic needle, irrespective of the relative proximity between the container and needle themselves. Representative, specific examples of "syringes" as defined herein include (but are not intended to be limited to): conventional staked-in needle syringes, ISO 11040-4 conforming prefilled syringes, removable hub needle/syringe body systems including those with a leur taper, infusion sets, single use and multi-use cartridge-based syringe systems, multi-chambered and variable dose syringes, as well as cartridges, vials and pouches (rigid or collapsible) which are configured to contain a drug and be used in conjunction with a needle to deliver a small injection volume (i.e. dose) of the drug.

Similarly, the use of the term "autoinjector" herein is intended to encompass both the conventional understanding of that term, as well as any other small form factor, hand-holdable or wearable, injection-type, or infusion-type (i.e. for delivery of a drug via a needle over a period of time lasting on the order of several minutes), drug delivery device.

The above will become evident from the following description and the figures wherein same number in the different views connote the same item.

For purposes of explanation, in general, the power pack approach will be described in the following manner. First, the description of a commercially suitable example implementation of one power pack variant is provided. Then, commercially suitable example implementations of autoinjectors containing, or suitable for use with, a power pack constructed in accordance with the principles herein are described. Next, various alternative variant details will be provided that can be used in some implementations. Finally, a generic example of the power pack approach is described due to the sheer number of different variant implementations that can be constructed without departing from the power pack approach as described herein.

Power Pack Structure and Operation

FIGS. 1A through 1H respectively illustrate, in simplified form, different exterior views of one example of a representative, commercially suitable example implementation of the inventive power pack 100. As shown, the power pack 100 is in its "initial" state, meaning the state in which it is ready to be, and capable of being, used as described herein.

Specifically, FIG. 1A is a front perspective view of the power pack 100, in which the upper face 10 is the same as the lower face 12 (not shown) and the right face 14 is the same as the left face 16 (not shown). FIG. 1B is a front plan view of the power pack 100. FIG. 1C is a rear perspective view of the power pack 100 and FIG. 1D is a rear plan view of the power pack 100.

FIGS. 1E and 1F are, respectively, plan views of the upper face 10 and right face 14 of one example of a representative inventive power pack 100 embodying the instant innovations. FIG. 1G is a cross sectional view of the power pack 100 taken along A-A of FIG. 1E. Similarly, FIG. 1H is a cross sectional view of the power pack 100 taken along B-B of FIG. 1F.

The components of the example power pack 100 will now be described with reference to the cross sections shown in FIGS. 1G and 1H.

As shown, in general overview in FIGS. 1G and 1H, the power pack 100 is made up of a canister 110, a valve mechanism 120, an activator body 130. As shown, purely for ease of manufacture of this variant example, the canister 110 is made of two components, a canister front 112 and a canister back 114 which can be coupled and sealed to each other to together define a reservoir 116, the volume which is used to hold a propellant or compressed or liquefied gas 111. For simplicity of explanation, the term "driver" will be used to refer interchangeably to a propellant comprising a compressed or liquefied gas.

Note here that, as used herein, "liquefied gas" is used to refer to a gas that has been compressed to its vapor pressure so that an equilibrium exists within the vessel in which it is contained such that some portion of the volume is liquid. Advantageously, it is known from basic thermodynamics that materials in their liquid form require much less space than in their gaseous form, often several hundred times less space. The pressure required for common liquefied gases at room temperature range from around 17 psi for n-butane, around 760 psi for nitrous oxide ($N_2O$) and to around 850 psi for carbon dioxide ($CO_2$). In addition, combinations of gasses can be used to modify the pressures to around a particular desired pressure. For example, specific hydrocarbon propellants (e.g. butane, isobutane, and propane) can be mixed in varying quantities in known manner to obtain pressures ranging from over about 17 psi to about 108 psi. Practically any pressure within the n-butane to carbon dioxide range can be obtained by mixing various gases having differing vapor pressures. It is further known from thermodynamics that, when a liquefied gas stored in a closed container, its internal pressure is directly related only to its temperature and, for a fixed temperature, the pressure generally remains effectively constant until all the liquid portion has boiled off into the gaseous state. However, the refrigeration effect of expanding gases means that, in practice, as the contents are expelled from the container, the temperature of the liquefied gas may decrease leading to pressure decrease. Consequently, some variants will require use of other means, as described herein, to deal with such a resultant pressure decrease. The use of a liquefied gas at the appropriate pressure in the manner described herein can provide advantages over present autoinjector technology because it allows for construction of a power pack that can operate as a compact energy and constant pressure source. In addition, and advantageously, power packs can be constructed as described herein using a liquefied gas at a higher pressure than would be needed and regulate the pressure down to the desired use pressure. In doing so, advantages over conventional autoinjectors can be obtained.

In contrast, the use of the term "compressed gas" as used herein means a gas that is stored at a pressure and temperature where the gas is never liquefied. With compressed gasses, as the gas is expelled from the container in which it is stored, the internal container pressure decreases. Common examples of such containers are SCUBA air tanks, which are commonly pressurized to around 3000 psi and compressed natural gas (CNG) tanks, which are commonly pressurized to about 2900-3600 psi. With compressed gasses, a pressure-regulating device must be used to obtain a constant pressure. In addition, because no liquefying occurs, the use of compressed gas is less desirable than liquefied gas because the container will tend to be larger and, due to the strength needed to contain the higher pressures, may be heavier as well.

Finally, it should be noted that, as used herein, the terms "propellant," "liquefied gas" or "compressed gas" are intended to also include gasses that may be the result of a chemical reaction within, or associated with, the storage container, in the instant example, the canister 110. Since the use of a particular "propellant," "liquefied gas" or "compressed gas" will be implementation specific, as used herein, the term "driver" is intended to generically encompass "propellants," "liquefied gases" and "compressed gases," the selection of which will be a function of the particular intended implementation, an not mandated by the approach itself.

The canister 110 further includes a valve seat 118 against which part of the valve mechanism 120 will interact to prevent the driver from unintended escape. The canister 110 is shaped to contain the driver as efficiently as possible and facilitate controlled release when the valve mechanism 120 is actuated. As a result, the canister 110 will typically be shaped so that the reservoir 116 is some form of substantially rounded volume, for example, for high pressure drivers, a volume that is shaped substantially like a sphere, capsule (a.k.a. "stadium of revolution"), egg, ellipsoid, prolate spheroid, superegg (of n=2, 3 or 4) or other related shape, so as to contain the driver under pressure without rupture. For lower pressure drivers or higher strength materials, any shape suitable to contain the driver without rupture may be used.

In many implementations, it is important to only dispense the gas phase of the driver from the canister. It is known that pressure regulators do not function well when the liquefied state is present because the liquid will continue to boil off inside the regulator, which can cause the pressure to rise above the desired regulated pressure. In addition, flow regulators will often behave differently with a liquid phase than a gaseous phase. If the canister is configured such that it can only be used in a single orientation and will remain essentially stationary, it is simple to draw only gaseous phase by only drawing from above the top level of the liquid phase. However, autoinjectors are typically used in different orientations, even by the same user for the same drug in different circumstances. Thus, irrespective of canister 110 shape, for applications where the driver in the canister 110 is maintained under pressure in a liquid state, the valve seat 118 should typically be configured to be located within the canister 110 at about the center, focus or centroid of the canister 110, such that the canister 110 can be filled with driver to a level that is always below the valve seat 118 so as to enable the power pack 100 to be stably oriented in any direction without liquid-state driver covering the valve seat 118. In this way, the power pack 100 can be actuated while avoiding liquid-state driver exiting through the valve mechanism 120. This means that the liquid state driver will occupy less than 50% of the volume, and more typically between about 25% and about 45% of the volume, and most likely between about 30% and about 40% of the volume, although less can be used as well provided the amount of driver and the pressure that it can exert (as described in greater detail below) is sufficient to move a syringe stopper enough to deliver the proper dose of drug from within the syringe it is operating on. Note further that, with some implementations that use a driver that is liquefied gas, it may further be desirable to include a diffuser in the canister to control boil off of the liquefied gas in order to minimize or prevent the liquefied gas from being expelled if liquid phase is in contact with the valve seat 118.

By way of examples, representative, non-exhaustive suitable drivers can include carbon dioxide ($CO_2$), isobutane, propane, R134a and dimethyl ether (DME).

The valve mechanism 120 is made up of the valve seat 118, a valve 122, having an elongated stem 124 portion and an enlarged head 126 portion, a valve spring 128.

The activator body 130 includes an interior void 132 sized to closely accommodate the outer peripheral shape of at least the forward-most part of the canister 110 while still allowing the canister 110 to rotate relative to, and within, the activator body 130 through, for example, an arc of less than about 90° and, depending upon the particular implementation, an arc typically of less than 30°, and ideally, an arc of about 15° or even less. As will be described in greater detail below, this rotation affects the ability to actuate the power pack 100 (i.e. release the driver for use).

The activator body 130 further includes a valve actuation pin 134 sized so that it can interact with the valve mechanism 120 as described below. In addition, with this implementation example, the activator body 130 at the exhaust end 136 includes a journal 138 on its exterior 140 that is appropriately sized to receive a flexible syringe seal 142 which will be used to form a pressure seal between the power pack 100 and a syringe it will interact with. Alternatively, the power pack 100 can be configured to seal against the outside of the syringe as well, or instead of, sealing against the inside of the syringe. Still another potential alternative would be to use a seal that seals the power pack 100 to flanges on the syringe or some other place. In this regard, the important factor is that there is a seal between the exhaust of the power pack 100 and the volume into which the driver will pass to move a syringe stopper (directly or indirectly), not its type, orientation or location.

Similarly, a canister seal 144 is located between the exterior of the canister 110 and the interior of the activator body 130 to prevent the drive gas from escaping between the two during use and to form a cavity 148 into which driver can enter and back pressure can build up during use. Finally, the activator body 130 has at least one, and typically multiple, gas outlet(s) 146 through which the driver will pass during activation which act as a flow metering or control mechanism in addition to, or in conjunction with, pressure control.

In general, the rate of flow of the gas exiting the canister can easily be controlled by any of many methods to great advantage because simple flow rate control can be used to solve, if not eliminate, problems common to conventional mechanical energy reliant injectors. For example, flow control can be used to control injection speed.

With conventional purely mechanical injectors, injection speed is often directly related to the force applied by the injection spring. If no additional damper is provided, the resistance which regulates the speed of injection is primarily a result of the viscous resistance of the liquid drug passing through the needle, and to a lesser degree by, for example, friction between the stopper and wall of the syringe or other mechanical drag forces, which can vary among specific injector units. Since, even between two of the same injector and drug pairing, this variability can exist, there must always be some margin in the injection spring force available to overcome the variability in forces required to empty the syringe. Thus, for a given injector intended for use with a specific drug, the injection spring must be designed for a force higher than is needed for the typical or average delivery of the injection. Compounding the problem, most springs lose force as they are released. As a result, since the variability in force can occur anywhere along the required stopper travel (including near the end of its travel) spring force available near that end point must be sufficiently high to provide a sufficient safety margin, rendering the initial applied force unnecessarily larger than required. This higher force is the largest factor determining the injection speed, and it is common with such devices to try to minimize the available force margin in order to regulate the injection speed to a rate slower than what the over-sized spring provides, but this requires some added mechanism which involves increased cost and often size.

In contrast, implementations of the approach described herein advantageously can more easily regulate the injection speed for a given drug without overcompensating at the start of the injection or risking insufficient force at the end. Specifically, through use of the principles described herein of a constant pressure source coupled with a flow regulator, autoinjectors can be configured to provide a wide range of injection times that is not tied to injection forces, as it is with many mechanically powered injectors. The pressure can be selected to be sufficient for the highest rated injection force, yet the flow rate of the driver can be regulated down to the desired flow rate. Thus, by implementing the instant approach, an injection can occur at around the desired slow rate but, if an obstruction is encountered, the pressure will then rise as driver passes through the flow regulator until the obstruction is overcome (at which point the pressure will reduce) or the driver comes to equilibrium with the driver in the constant pressure source.

Other advantages obtainable by using the combination of a constant pressure driver and flow regulation will be described later.

Returning to the instant example implementation, the power pack 100 further includes a spring 150, which as shown is a wave spring, which abuts, and interacts with, the canister back 114 to, as described below, provide a force that urges the canister 110 towards the valve actuation pin 134. A clip 152 is affixed to the power pack 100 on the opposite side of the spring 150 constrains the spring 150 within the power pack 100. In this "initial" state, the spring 150 is maintained in at least a partly compressed state between the canister back 114 and the clip 152.

FIGS. 2A through 2D show the power pack 100 of FIGS. 1A through 1D upon entering the "activating" state. To reach the activating state, the canister 110 is rotated within the activator body 130 which is only evident in these views by the position of the wings 18 that are part of the canister 110 and externally visible.

FIGS. 2E and 2F show the upper face 10 and right face 14 of the power pack 100 when it is in the "activating" state. In order to show what happens in the transition between the "initial" and "activating" states, FIG. 2G is a cross sectional view of the power pack 100 taken along C-C of FIG. 2E and FIG. 2H is a cross sectional view of the power pack 100 taken along D-D of FIG. 2F.

As can be seen in FIGS. 2G and 2H, the rotation of the canister 110 places the canister 110 in a position that allows the spring 150 to expand and urge the canister 110 deeper into the activator body 130. This rotation of the canister 110 is notable by comparison of the position of the wings 18 through juxtaposition of FIG. 1B with FIG. 2B or FIG. 1D with FIG. 2D and the movement is evident by the reduction in volume of the cavity 148.

FIG. 3 shows the positions of the wings 18 on the canister 110 in the initial position and, in dotted lines, the activating position. As can be seen, for this example implementation, the canister will have to be rotated through an arc of about 15° from the position for the "initial" state to the position for the "active" state. Depending upon the particular implementation, this arc can be smaller than about 15° and can even generally be as large as about 45° or so, but a smaller arc is more desirable because it allows for a simpler design.

Turning back to discussion of the activation state, as shown in greater detail in FIG. 4, which is an enlargement of the central portion of FIG. 2G, the movement of the canister deeper into the activator body 130, in turn, causes the valve actuation pin 134 to contact the syringe end 404 of the stem 124 portion which causes the valve spring 128 to compress and the enlarged head 126 portion to move away from the valve seat 118 allowing (as shown by dashed line) gaseous driver to exit the canister 110 via the valve seat 118, pass along the stem 124 portion. As further shown in FIG. 5 (which is a further enlargement of part 406 of FIG. 4) the driver can then exit the power pack 100 through the outlet(s) 146, with some driver also leaking between the exterior of the valve mechanism 120 housing and its corresponding interior portion of the activator body 130 into the cavity 148 (not shown).

Returning to FIG. 3, it is worth noting at this point that the size and number of outlet(s) 146 can be used to regulate the flow of the driver exiting the power pack and, consequently, the time it takes to move the syringe stopper from actuation to full dose delivery.

When, for example, the force needed to move a particular syringe stopper to deliver a dose of a specific viscosity drug through a specific size needle is known, as are the desired average time for delivery of a full dose and the initial state pressure in the canister 110, the proper sizing of the outlet(s) can straightforwardly be used to regulate the flow and achieve the intended average delivery time for the dose. In addition, in some cases, it may be desirable to have a number of rather small outlet(s) 146 as opposed to fewer (or even a single) large outlet to account for manufacturing variances during hole formation, contaminants entering the holes during manufacture or assembly, or potentially for blockages caused by solid impurities in a particular driver. Thus, if a larger number of smaller outlet(s) are used, if one or a few are blocked by foreign matter, the overall operation of the power pack 100 will not be as likely to be adversely affected, as compared to using one or only a few slightly larger outlets because the affect of an individual blockage on flow rate will be less. Conversely, in some cases, using a few larger outlets can be advantageous, for example, where likely impurities will be known to be much smaller than the size of any individual outlet. Advantageously, depending upon the size, material involved, required precision, and number of outlets, creation of the outlet(s) 146 can be accomplished through any suitable process, for example, micro hole drilling using micro drills, micro-CNC or laser drilling technology. Such hole-forming technologies, per se, are all known and thus, need not be described herein. As shown in FIGS. 1B, 2B and 3 (among others) the example power pack 100 has twelve holes, each about 0.03 millimeters in diameter.

As will be explained in greater detail below, advantageously, the exit pressure of the power pack 100 will be self-regulating in that the flow of gas will automatically increase or decrease to maintain a constant pressure at the outlet. The interaction of the canister 110 with the spring 150 and valve mechanism 120 (with the valve actuation pin 134) cooperative to regulate the pressure through metering of gaseous driver out of the canister 110.

Specifically, if the pressure on the syringe side of the activator body 130 decreases to below that of the spring 150, the spring 150 will urge the canister 110 in that direction (i.e. deeper into the activator body 130), which causes the valve actuation pin 134 to open the valve mechanism 120 further and release more driver. In contrast, as the pressure on the syringe side of the activator body 130 increases, it asserts a force opposite to that exerted by the spring 150, predominantly via pressure build up in the cavity 148. If the pressure on the syringe side of the activator body 130 (e.g. in the cavity 148) increases to the point that it applies a greater force than the force exerted by the spring 150, the canister 110 will be urged towards the spring 150 causing the valve mechanism 120 to move away from the valve actuation pin 134 allowing the valve spring 128 to relax (i.e. decompress) and cause the space between the enlarged head 126 portion and the valve seat 118 to decrease, thereby reducing release of driver via the valve mechanism 120.

In between the two extremes, under ideal conditions during dose delivery, the power pack 100 will reach an equilibrium state where only a specific constant pressure exerted by the driver will be needed to keep the stopper of the syringe moving at a desired rate. In such a case, during that period the pressure in the cavity 148 will exert a force on the canister seal 144 that is equal and opposite to the force exerted by the spring 150. As a result, the position of the enlarged head 126 portion relative to the valve seat 118 will remain constant, as will the position of the spring 150, and the canister 110 relative to the activator body 130. At this point it should be noted that, ideally, the valve mechanism 120 and outlet(s) 146 should be designed collectively such that the rapid opening and closing ("chattering") of the valve mechanism 120 is avoided. In addition, it is desirable to specifically have the valve mechanism 120 and outlet(s) 146 designed such that steady movement of a syringe stopper during drug delivery can occur through a steady "leakage" flow of driver from the canister 110.

FIGS. 6A and 6B are respectively the cross sectional views of the power pack 100 taken along C-C of FIG. 2E (FIG. 6A) along D-D of FIG. 2F (FIG. 6B) at an example equilibrium point during the activation state (i.e. the valve mechanism 120 is slightly open in a steady-state position.)

In general, the foregoing describes the internal structure, function and operation of a representative example power pack 100. Note that, other than the interior of the canister 110, the specific shapes and sizes of the components are more a function of the particular autoinjector with which they will be used, aesthetic issues, or other design criteria which are all irrelevant to understanding the general structure and operation of the power pack aspect of the invention. Other shapes, sizes and configurations can be straightforwardly created by employing the teachings contained herein. Thus, the specific shape(s) of the example power pack 100 or any component(s) thereof should not be considered as limiting the scope of the invention except as expressly claimed.

Finally, with respect to the power pack 100 itself, it should be noted that one or both of the exterior faces 10, 12 may also optionally include features that can be used to provide benefits not specifically required for drug delivery. For example, one or more features 20, 22 (FIGS. 1A-1D) can optionally be included to provide, or interact with other portions or features of the autoinjector to provide, for example, an indication that the complete dose of drug has been delivered. This can take the form of a visual indicator, such as a colored component becoming visible or disappearing, or an audible indicator, such as a "click" or other audible noise being created or triggered, or some combination of the two. Similarly, features 20, 22 can additionally or alternatively be used for some other purpose(s), for example, to trigger retraction of the needle once drug delivery is complete, trigger and/or "lock" a safety shield into a position such that a used, non-retracted needle cannot easily or accidentally be contacted, and/or trigger or cause some other action to prevent re-use of the autoinjector.

As will now be understood, power packs employing the teachings herein are designed to work in conjunction with syringes to deliver a drug dose. In order to ensure proper understanding, a brief discussion of syringes will be provided with reference to FIGS. 7 and 8.

FIG. 7 is a simplified view of an example conventional syringe configuration with which power packs as described herein may be used. As shown the syringe 700 includes a flange 702, a body 704 and cap 706. The cap 706 provides a protective covering over a syringe needle (not shown). In addition, the cap 706 includes features 708 to make the cap 706 easier to grip and remove when the syringe 700 is to be used.

FIG. 8 is a cross-sectional view of the syringe 700 of FIG. 7 taken through the center in the X-Y plane. As can be seen in the cross section, the syringe 700 also includes a stopper 802 that can move along the length of the syringe 700 within the body 704 and a hollow needle 804 through which a dose of a drug is administered, which, as shown in this FIG. is a staked needle. Collectively, the body 704, stopper 802 and needle 804 generally define the boundaries of a chamber 806 where the drug is stored prior to administration. The drug is administered through the needle 804 by application of pressure on the side 808 opposite the chamber 806 to the stopper 802 via a plunger (not shown). This pressure drives the stopper 802 along the body 704 towards the needle 804 which forces the drug out through the hollow needle 804.

With the foregoing in mind, the interaction of the power pack 100 with a syringe will be described. For simplicity, the syringe of FIGS. 7 and 8 will be used for purposes of illustration with the understanding that power packs configured in accordance with teachings contained herein can, with non-inventive straightforward modification of size and shape, be used with any of numerous syringe sizes and configurations, as well as cartridges, vials, collapsible bags or any other appropriate primary drug containers.

FIG. 9 illustrates, in simplified form, the portion of the cross section of the syringe 700 of FIG. 7 combined with the power pack 100 (cross section of FIG. 1E) as the syringe 700 and power pack 100 would be used together.

As shown, with this example implementation, the exhaust end 136 of the activator body 130 is dimensioned to fit inside, and closely conform to, the interior dimension of the body 704 of the syringe 700. The exhaust end 136 of the power pack 100 is inserted into the syringe body 704 with the syringe seal 142 providing a tight seal between the two to prevent leakage of the driver. Alternatively, the activator body could be constructed so as to envelop, as opposed to being inserted in, the end of the syringe 700, the important aspect being that the activator body 130 is coupled to the end of the syringe 700 in a manner that forms a tight seal between the power pack 100 and the component that will directly or indirectly move the stopper of the syringe so that the driver does not leak, thereby causing an undesired pressure drop.

Initially, with this implementation, the driver is a liquefied gas that is wholly contained within the canister 110 and is maintained at a pressure equal to or above the vapor pressure (denoted "$P_A$") of the driver. Upon actuation, the driver exits the canister 110 via the valve mechanism 120 which acts as a pressure regulator and can be used, as appropriate, to reduce the pressure to a regulated pressure (denoted "$P_B$") prior to exiting the outlet(s) 146. Once the driver exits the outlet(s) 146, it is trapped within a region 900 bounded by the power pack 100, the internal wall of the syringe body 704 and the stopper 802. Again (or alternatively), by appropriate sizing, the outlet(s) 146 can be used to regulate the flow and thereby, in some cases, reduce the pressure of the driver in this region (denoted "$P_C$") such that the pressure is below $P_B$ but above the pressure necessary to move the stopper 802. This causes the driver to have the effect of a conventional syringe plunger and drive the plunger towards the needle 804 and, consequently, the drug out through the needle 804.

Advantageously, in some implementations, by appropriately changing the sizing of the outlet(s) 146 and/or the opening of the valve mechanism 120, the time for completion of the injection can be modified.

In general, syringes for use with autoinjectors are standardized and manufactured to specifications that establish internal tolerances and maximum allowable variances/deviations from those tolerances to be within the specification, however the siliconization process can cause, or result in, internal glide force variances along the interior of the syringe body 704 that are independent of the manufacturing specifications and that can, as noted above, detrimentally affect stopper movement. Similarly, the viscosities of drugs that are deliverable through such syringes are also known. Thus, for a given combination of standard syringe size and shape, siliconization amount or distribution, and drug viscosity, the maximum pressure that could be required for delivery of the drug via a syringe that is within the specification but has a deviation related to siliconization will vary. Specifically, a problem currently exists in some cases with conventional syringes wherein variance of the interior wall 808 along the syringe body 704 due to siliconization imperfections or variation can act against movement of the stopper 802 during drug delivery. This variance can, in some cases, alter the friction between the stopper 802 and interior wall 808 along the stopper's path during delivery and thereby affect the force necessary to continue to move the stopper 802 within the syringe body 704.

As noted above, with spring actuated autoinjector approaches, such motion-affecting circumstances must be anticipated, so the autoinjector must be preconfigured with spring(s) that exert a force that is equal to or greater than that highest impeding force that could be encountered during drug delivery. Moreover, since simple mechanical springs cannot adjust force that they apply over most of their range the design must take into account a "worst case" and drug delivery speed with those autoinjectors, being a function of that force, will often necessarily be higher for unimpeded cases and can result in unintended or unacceptable drug delivery speeds or other unintended performance issues. On the other hand, if the spring is made weaker, to slow the injection speed, an impeded case can cause the stopper to stall or halt at an imperfection in a manner that can't be overcome and thereby the device can fail to deliver the desired dose.

Advantageously, with the power pack approach described herein, the pressure applied to the stopper 802 is auto-regulated so impeded movement due to such imperfections will cause pressure within the region 900 to build up until the impediment is overcome, at which point, smooth delivery at reduced pressure will resume. This fact, considered in conjunction with appropriate sizing of the valve mechanism 120 and outlet(s) 146 sizing allows the designer to significantly lengthen the time required to deliver a full dose via the injection, without the need to pre-allow for such impediment situations. As long as a power pack implemented in accordance with the teachings herein can exert a pressure force (referred to herein as the "Minimum Safety Pressure" or "MSP") at least as high as that maximum pressure required for the allowable variations of an "in-specification" syringe and drug combination, the drug will be properly delivered at a rate equal to or less than the desired rate (i.e. so long as the pressure force normally exerted by the driver as it exits the outlet(s) 146 of the power pack 100 to properly drive the stopper 802 is sufficiently lower than the pressure in the canister 110, so that it can build up to a pressure necessary to overcome the impediment).

As noted above, optional features can be incorporated into or actuated by the power pack. Advantageously, by employing the teachings herein, the impediment-caused pressure build up can be used to help implement one or more of the features. For example, at the end of the dose, the stopper 802 of the syringe 700 will have traveled within the syringe body 704 (towards the needle 804) essentially as far as it can go. Advantageously, once the stopper 802 cannot move any farther, as long as the valve mechanism 120 remains open, pressure will continue to build up in the region 900 and, consequently, propagate backwards into the cavity 148 where it will act against the power pack 100 itself, at a high enough pressure, cause the power pack 100 to move backwards from the stopper and within the autoinjector in which it is housed. This "reverse" activator body 130 movement can then be employed, alone or in conjunction with some other feature or apparatus, for example, to trigger some action, for example, an end of dose indication and/or needle shield deployment. By way of simple example, as shown, the feature 22 can be configured to interact with, and engage, a component of the autoinjector in which it is housed to provide an end of dose indication. The minimum pressure necessary to initiate this reverse movement is referred to herein as the Trigger Pressure ("$P_T$").

For purposes of further illustration and understanding, Table 1 specifies, for different drivers, example approximate pressure(s) $P_A$, $P_B$, $P_C$ and $P_T$ for the illustrative combination of power pack 100 and syringe as in FIG. 9, using a syringe that is a standard 1 mL glass syringe with a staked-in needle pre-filled with a 1 centipoise (cP) viscosity liquid and with the outlet(s) sized for a time for drug delivery of about 5 seconds (i.e. the typical full-dose injection time of many conventional spring actuated autoinjectors).

TABLE 1

| Driver | $P_C$ | MSP | $P_B$ | $P_A$ | $P_T$ |
|---|---|---|---|---|---|
| $CO_2$ | ~10-~20 | ~64 | ~140 | ~845 | ~64-~93 |
| Isobutane | ~10-~20 | ~31 | ~31 | ~31 | N/A |
| Propane | ~10-~20 | ~64 | ~108 | ~108 | ~64-~93 |
| R134a | ~10-~20 | ~45 | ~71 | ~71 | ~45-~60 |
| DME | ~10-~20 | ~35 | ~63 | ~63 | ~35-~50 |

(pressure ranges denoted in pounds per square inch ("psi"))

Note in Table 1 that with this specific configuration, for isobutane, propane, R134a and DME, the pressures $P_A$ and $P_B$ are the same. This is because, with this particular configuration, the valve mechanism 120 remains entirely open until the entire dose has been delivered. In addition, note that the maximum back pressure for isobutane is insufficient to drive the power pack 100 backwards at the end of a dose in this particular example implementation, so no $P_T$ is specified.

Autoinjector Design, Structure and Operation

Having described the interaction between a power pack and syringe, the structure and operation of some example autoinjector designs that could, but need not, incorporate a power pack implemented in accordance with the teachings herein will now be described.

Figure 13:
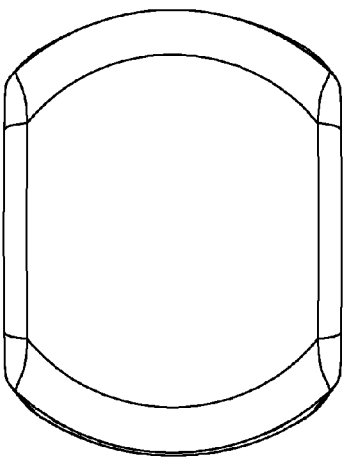
FIG. 13 is an enlarged rear elevational view of the autoinjector implementation of FIG. 10.
Figure 11:
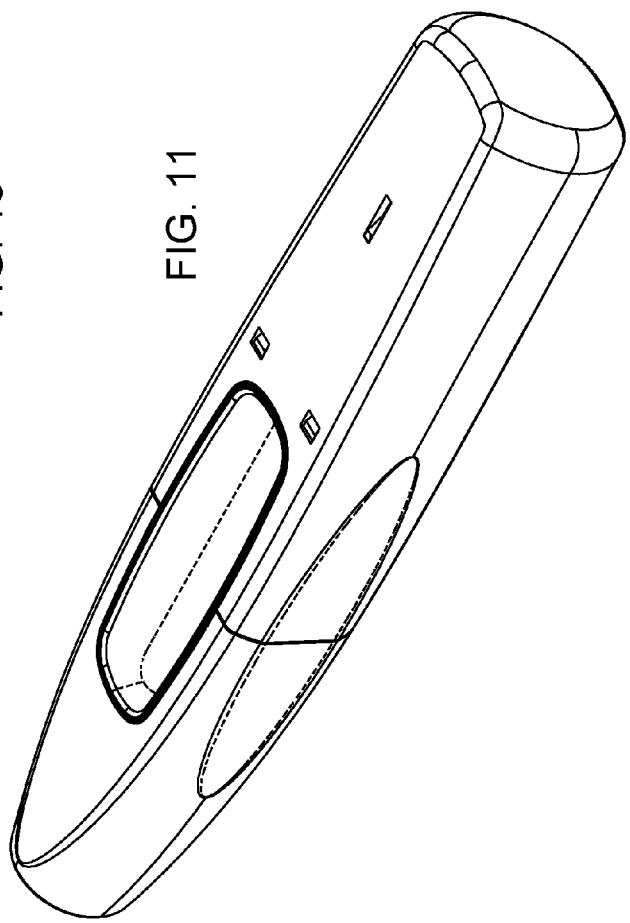
FIG. 11 is a rear perspective view of the autoinjector implementation of FIG. 10.
Figure 10:
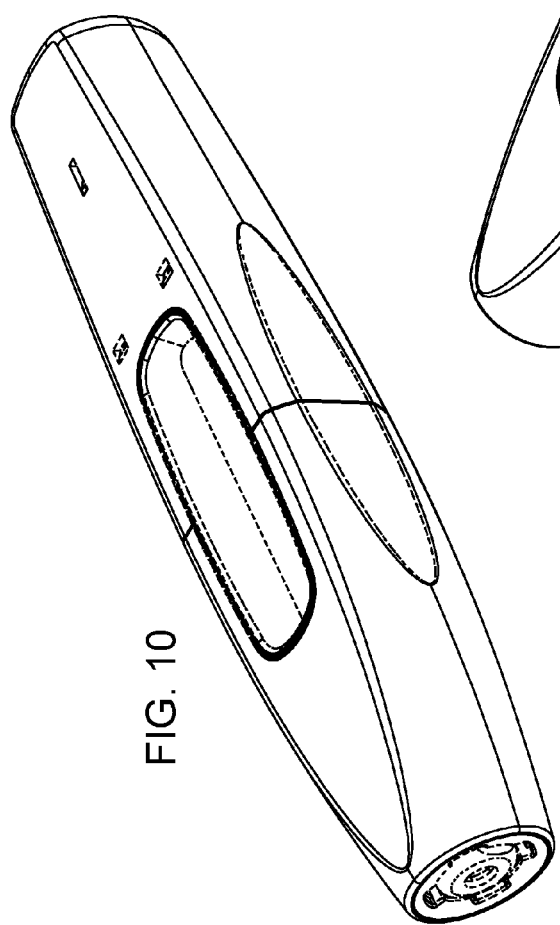
FIG. 10 is a front perspective view of a design for an autoinjector implementation.
Figure 12:
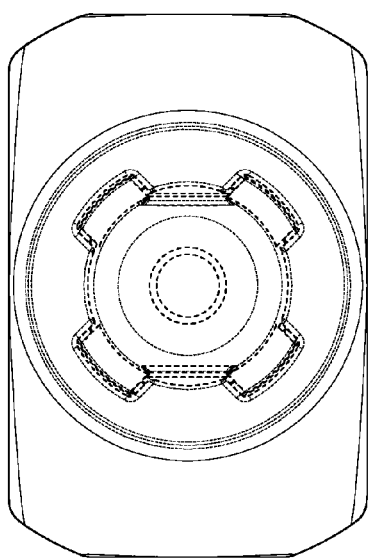
FIG. 12 is an enlarged front elevational view of the autoinjector implementation of FIG. 10.
Figure 14:
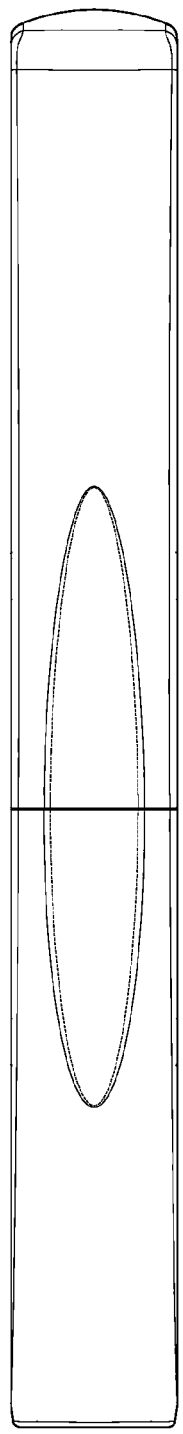
FIG. 14 is a right side elevational view of the autoinjector implementation of FIG. 10, the left side being a mirror image thereof.
Figure 15:
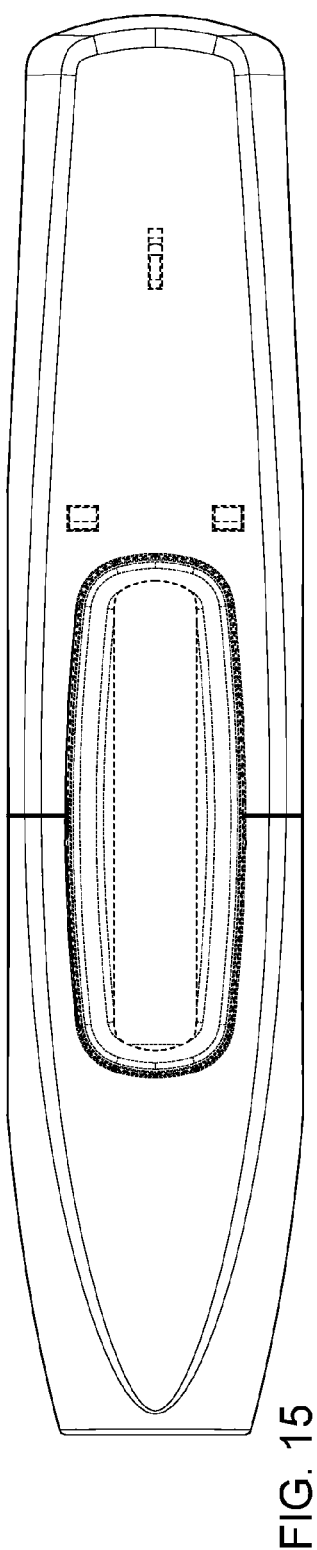
FIG. 15 is a top plan view of the autoinjector implementation of FIG. 10.
Figure 16:
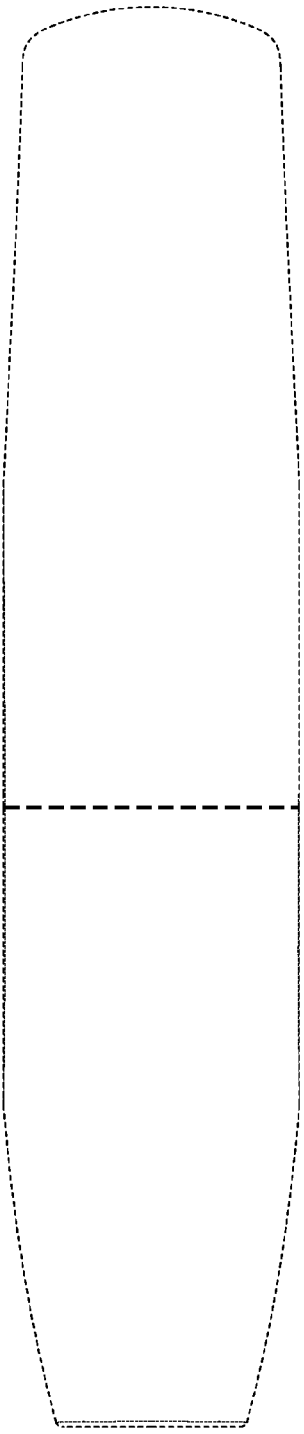
FIG. 16 is a bottom plan view of the autoinjector implementation of FIG. 10.

FIG. 10 is a front perspective view of a design for an autoinjector implementation; FIG. 11 is a rear perspective view of the design for the autoinjector implementation of FIG. 10; FIG. 12 is an enlarged front elevational view of the design for the autoinjector implementation of FIG. 10; FIG. 13 is an enlarged rear elevational view of the design for the autoinjector implementation of FIG. 10; FIG. 14 is a right side elevational view of the design for the autoinjector implementation of FIG. 10, the left side being a minor image thereof; FIG. 15 is a top plan view of the design for the autoinjector implementation of FIG. 10; and FIG. 16 is a bottom plan view of the design for the autoinjector implementation of FIG. 10.

Note that, in the views of FIG. 10 through FIG. 16, the broken lines illustrate optional additional features which need not form a part of the design. Note that an alternative variant of the design has the rear plan view being a mirror image of the top plan view of FIG. 15.

Figure 21:
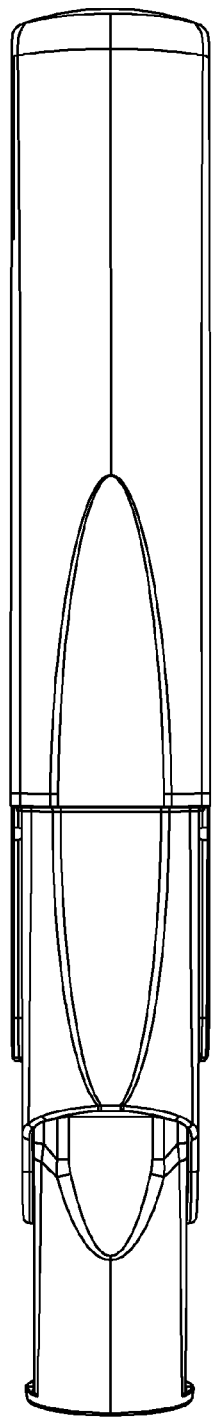
FIG. 21 is a right side elevational view of the alternative design for the autoinjector implementation of FIG. 17.
Figure 22:
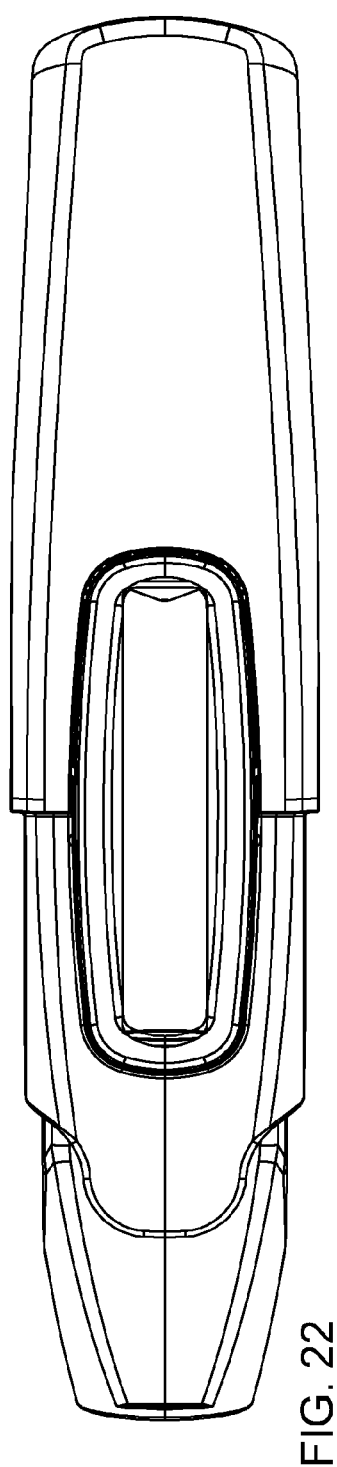
FIG. 22 is a top plan view of the alternative design for the autoinjector implementation of FIG. 17.
Figure 23:
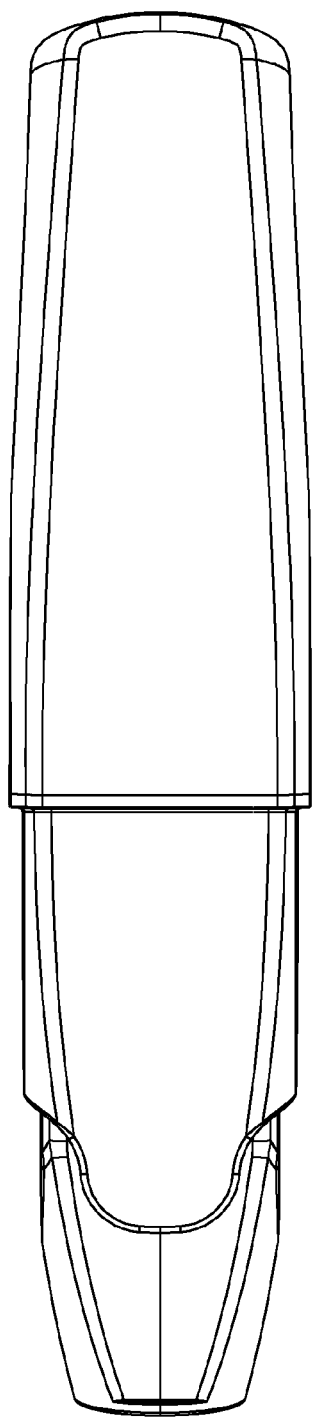
FIG. 23 is one bottom plan view of the alternative design for the autoinjector implementation of FIG. 17.

FIG. 17 is a front perspective view of an alternative design for an autoinjector implementation; FIG. 18 is a rear perspective view of the autoinjector implementation of FIG. 17; FIG. 19 is an enlarged front elevational view of the autoinjector implementation of FIG. 17; FIG. 20 is an enlarged rear elevational view of the autoinjector implementation of FIG. 17; FIG. 21 is a right side elevational view of the autoinjector implementation of FIG. 17, the left side being a mirror image thereof; FIG. 22 is a top plan view of the autoinjector implementation of FIG. 17; FIG. 23 is one bottom plan view of the autoinjector implementation of FIG. 17; FIG. 24 is an alternative bottom plan view of the autoinjector implementation of FIG. 17; and, yet other alternative bottom plan views would be either a mirror image of, or identical to, the top plan view of FIG. 22.

Note that, as with FIGS. 10 through 16, in the views of FIG. 17 through FIG. 24, the broken lines illustrate optional additional features which need not form a part of the design.

FIG. 25 is a right side elevational view of yet another variant autoinjector 2500 incorporating the teachings herein and FIG. 26 is a top plan view of the variant autoinjector 2500 of FIG. 25. As shown, the autoinjector 2500 is made up of a main body 2502 and a removable end cover 2504. Note that, in this view, the end cover 2504 covers, and conceals, part of the main body 2502.

In this variant, the top surface 2506 main body 2502 also includes a window 2508 through which a portion 2510 of the body 704 of a syringe 700 contained within the main body 2502 is visible. In addition, as shown, the top surface 2506 of the main body 2502 also includes an optional slot feature 2512 (which, for simplicity in this example, is shown as externally visible). The optional slot feature 2502 is designed to mate with a complementary protruding feature on the activator body of a power pack, for example, to optionally serve as a linear guide for the activator body in the longitudinal direction, to optionally resist rotation of the activator body during use), and/or to axially retain the power pack within the main body during assembly.

Having previously described the specific interaction between an example power pack 100 and syringe 700, the structure and operation of this example variant autoinjector 2500, which is configured for use with a power pack implemented in accordance with the teachings herein, will now be described with reference to FIGS. 25 and 26 as well as their cross sections.

FIG. 27 is a cross sectional view of the variant autoinjector 2500 taken along E-E of FIG. 25 and FIG. 28 is a cross sectional view of the variant autoinjector 2500 taken along F-F of FIG. 26.

Turning now to the cross sectional views if FIG. 27 and FIG. 28, it will be recalled that the syringe of FIGS. 7 and 8 included a cap 706 that had "grip" assisting features 708 on a surface thereof. Advantageously, as can be seen in FIG. 27, the inside of the end cover 2504 has features 2702 that configured to correspondingly mate with the features 708 of the cap 706 covering the needle 804 of the syringe 700. In this manner, advantageously, the cap 706 and syringe 700 combination can be maintained together when they are fitted into the main body 2502. Thus, a pre-filled syringe 700 can be received into the autoinjector 2500 without the needle 804 ever being exposed. In addition, by virtue of his feature, when use is initiated, removal of the end cover 2504 will also cause removal of the cap 706 from the syringe 700. Similarly, if the needle is not part of a retractable configuration, replacing the end cover will also replace the cap 706 over all or part of the needle 804.

As can also be seen in FIGS. 27 and 28, the syringe flange 702 is constrained within the main body 2502 and can, in some configurations, act as a depth stop for the power pack 100.

Figure 32:
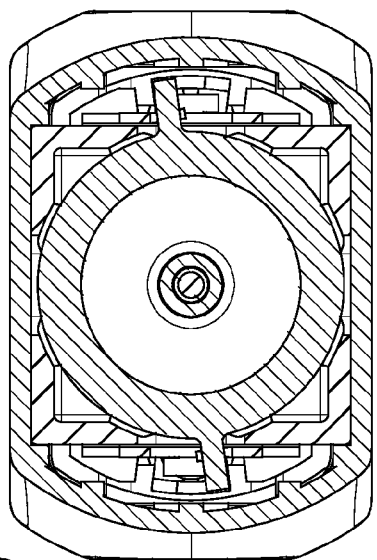
FIG. 32 is a cross sectional view of FIG. 26 taken along J-J.
Figure 31:
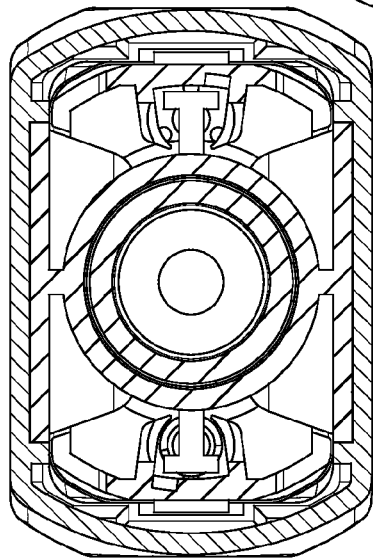
FIG. 31 is a cross sectional view of FIG. 26 taken along H-H.
Figure 29:
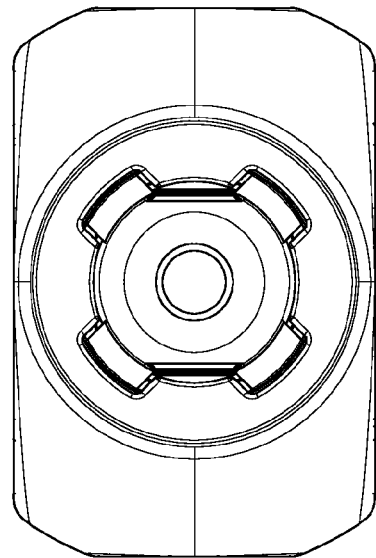
FIG. 29 is a needle-end view of the autoinjector of FIG. 25.
Figure 30:
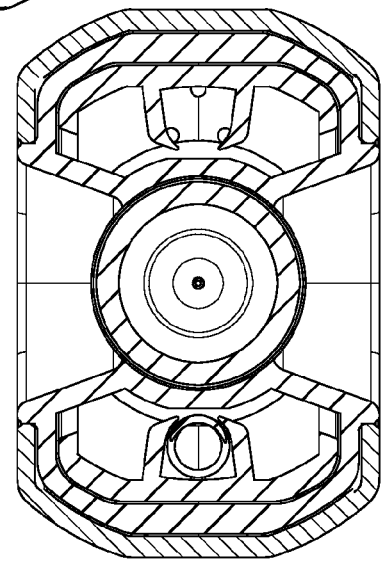
FIG. 30 is a cross sectional view of FIG. 26 taken along G-G.

Thus, FIGS. 25 through 28 show this autoinjector 2500 in the fully assembled state at a point in time prior to use. In addition, FIG. 29 is a needle end-on view of the autoinjector of FIG. 25. Moreover, to further aid in understanding the autoinjector 2500 and its operation, for completeness, various cross sections are also included for each stage of operation. For example, FIG. 30 is a cross sectional view of the autoinjector of FIG. 26 taken along G-G, FIG. 31 is a cross sectional view of the autoinjector of FIG. 26 taken along H-H and FIG. 32 is a cross sectional view of the autoinjector of FIG. 26 taken along J-J.

FIG. 33 is a right side elevational view of, in this case, the autoinjector 2500 of FIG. 25. Alternatively, FIG. 33 could also be a right side view of an alternative variant autoinjector that does not include an end cover 2504. FIG. 34 is a top plan view of the autoinjector 2500 of FIG. 33. As can be seen in these two views, the autoinjector 2500 includes a shield 3302 that impedes access to the needle of the syringe within the autoinjector 2500. As will be evident in subsequent views, the shield is movable between an extended position, as shown in FIGS. 33 and 34, and a retracted position within the main body 2502.

FIG. 35 is a cross sectional view of the variant autoinjector 2500 taken along E-E of FIG. 33 and FIG. 36 is a cross sectional view of the variant autoinjector 2500 taken along F-F of FIG. 34. Note that FIGS. 33-36 illustrate the autoinjector 2500, with the power pack 100 (and consequently the autoinjector 2500 overall) in the "armed" state.

As shown in FIGS. 35 and 36, the shield 3302 is maintained in an extended position by a compressible shield spring 3502. In addition, a portion 3504 of the shield 3502 extends along the inside of the main body 2502 so that it can interact with the power pack 100 as will be described below.

Figure 40:
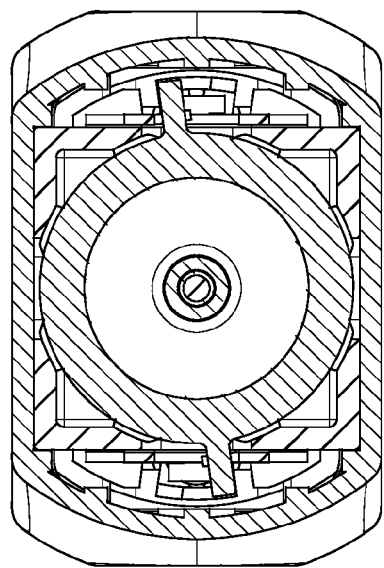
FIG. 40 is a cross sectional view of the autoinjector of FIG. 34 taken along J-J.
Figure 39:
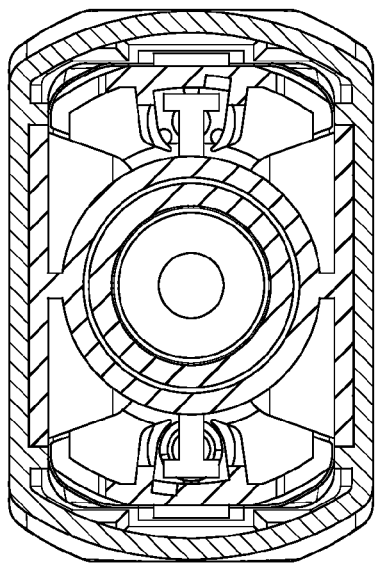
FIG. 39 is a cross sectional view of the autoinjector of FIG. 34 taken along H-H.
Figure 37:
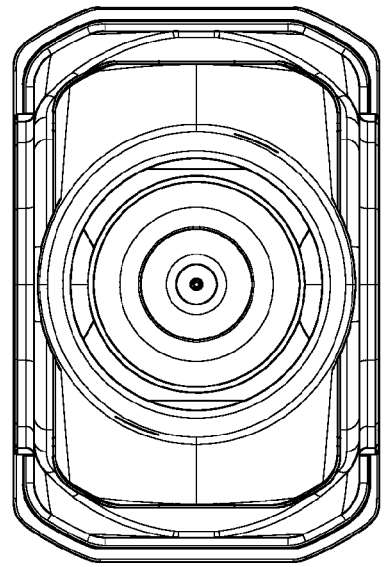
FIG. 37 is a needle end-on view of the autoinjector of FIG. 34.
Figure 38:
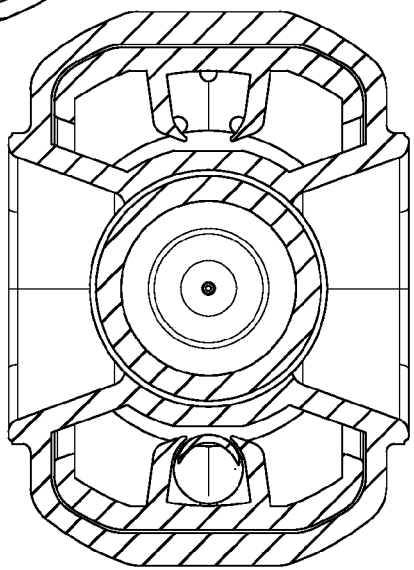
FIG. 38 is a cross sectional view of the autoinjector of FIG. 34 taken along G-G.

FIG. 37 is a needle end-on view of the autoinjector of FIG. 34. Again, for completeness, FIG. 38 is a cross sectional view of the autoinjector of FIG. 34 taken along G-G, FIG. 39 is a cross sectional view of the autoinjector of FIG. 34 taken along H-H and FIG. 40 is a cross sectional view of the autoinjector of FIG. 34 taken along J-J.

Figure 41:
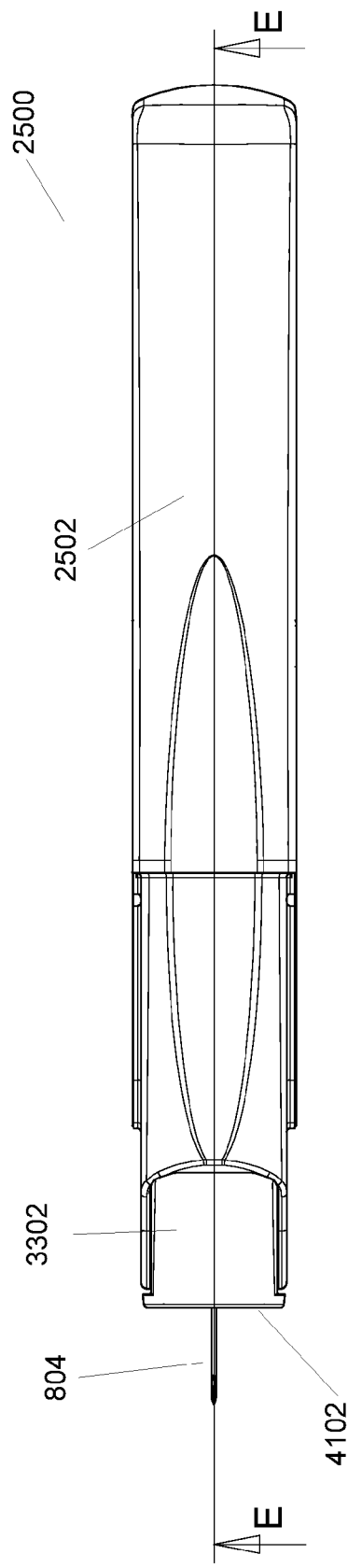
FIG. 41 is a right side elevational view of the autoinjector of FIG. 25.
Figure 42:
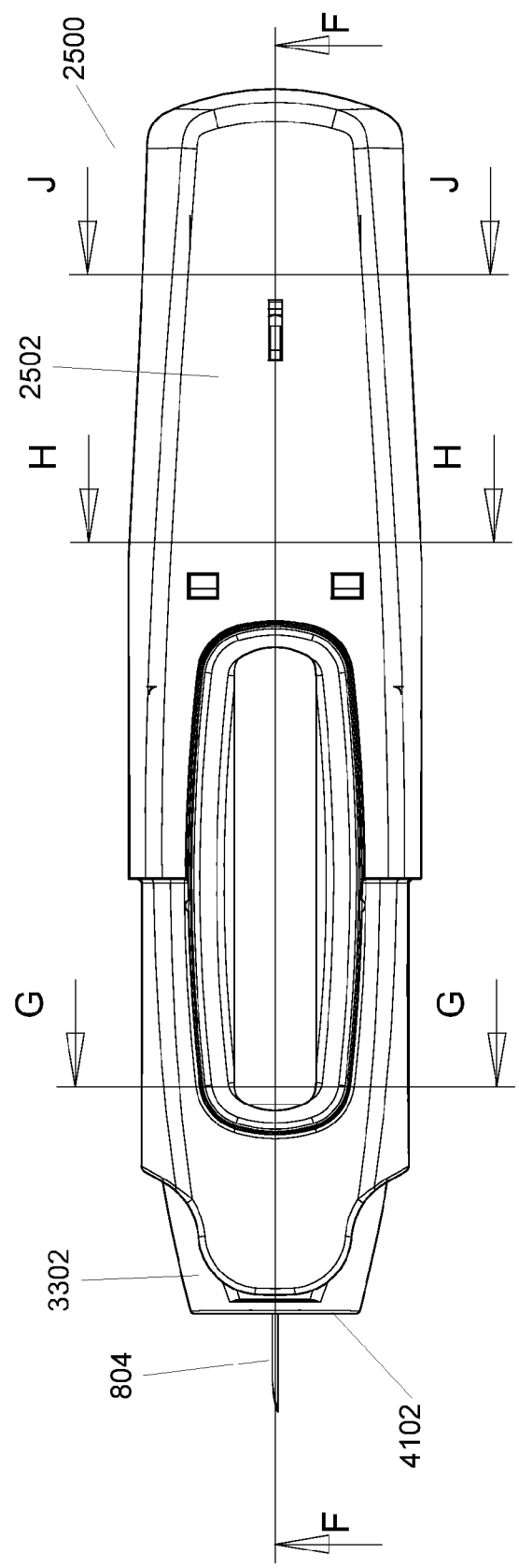
FIG. 42 is a top plan view of the autoinjector of FIG. 41.

FIG. 41 is a right side elevational view of, in this case, the autoinjector 2500 of FIG. 25 as it would look once the needle 804 has been inserted into the person at the injection site. FIG. 42 is a top plan view of the autoinjector 2500 of FIG. 41. As can be seen in these two views, pressing the extreme end 4102 of the shield 3302 against the person will cause the shield 3302 to move from the extended position of FIGS. 33 and 34, to the retracted position within the main body 2502.

FIG. 43 is a cross sectional view of the variant autoinjector 2500 taken along E-E of FIG. 41 and FIG. 44 is a cross sectional view of the variant autoinjector 2500 taken along F-F of FIG. 42. As can be seen by comparison of FIGS. 43 and 44 with FIGS. 35 and 36, the retraction of the shield 3302 has caused the portion 3304 to move closer to the power pack 100. Through this movement, the canister 110 is caused to rotate within the activator body 130, which allows the canister 110 to move deeper into the activator body 130, at the urging of the spring 150 as described above. At this point it should be noted that the rotation can be caused in any appropriate manner, for example, by causing the portion 3304 to move along an inclined plane (not shown), to trigger actuation of an auxiliary spring, or in any other manner, the particular method being unimportant to understanding the operation. As shown however, the portion 3304 imparts a force onto an inclined plane to thereby cause the rotation. In turn this causes opening of the valve mechanism 120 and allows some of the driver to exit the outlet(s) 146 and pass into the region 900 on the power pack 100 side of the stopper 802 so as to apply a force to the stopper 802 and thereby move it in the direction of the needle 804 and, in turn, force the drug (not shown) within the chamber 806 out through the hollow needle 804. Thus, FIGS. 41-44 illustrate the autoinjector 2500, with the power pack 100 (and consequently the autoinjector 2500 overall) in the "activating" state.

Figure 48:
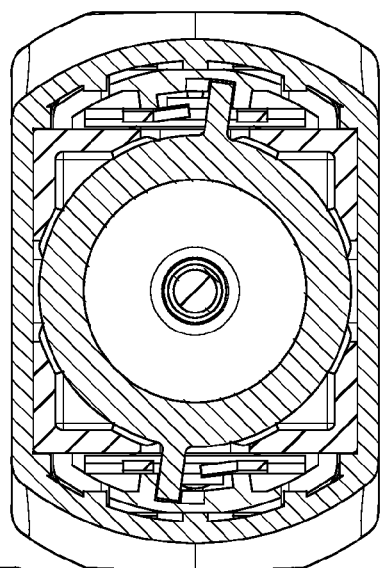
FIG. 48 is a cross sectional view of the autoinjector of FIG. 42 taken along J-J.
Figure 47:
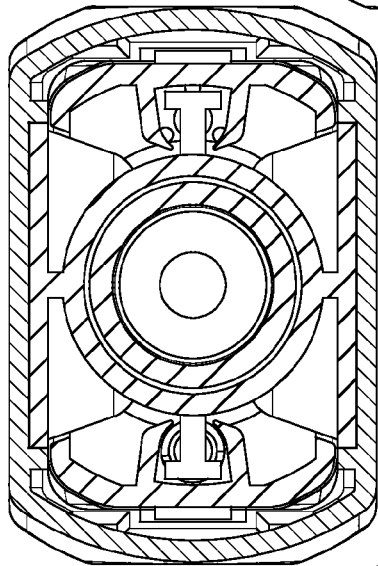
FIG. 47 is a cross sectional view of the autoinjector of FIG. 42 taken along H-H.
Figure 45:
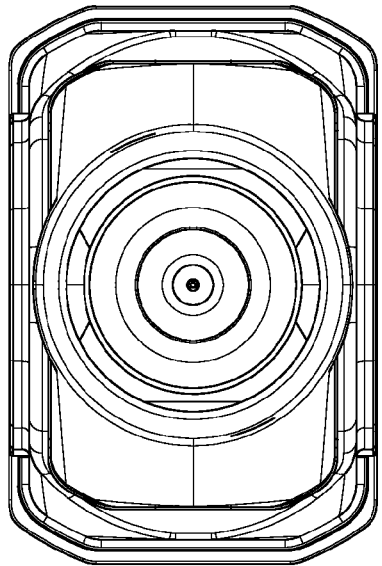
FIG. 45 is a needle end-on view of the autoinjector of FIG. 42.
Figure 46:
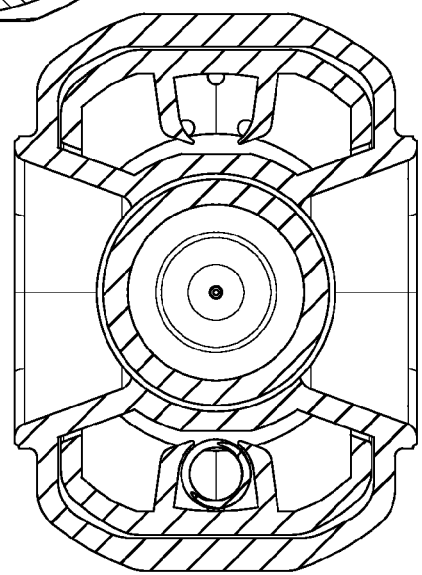
FIG. 46 is a cross sectional view of the autoinjector of FIG. 42 taken along G-G.

FIG. 45 is a needle end-on view of the autoinjector of FIG. 42. Again, for completeness, FIG. 46 is a cross sectional view of the autoinjector of FIG. 42 taken along G-G, FIG. 47 is a cross sectional view of the autoinjector of FIG. 42 taken along H-H and FIG. 48 is a cross sectional view of the autoinjector of FIG. 42 taken along J-J.

After a time following activation, the force applied by the driver will cause the stopper 802 to reach a position where a full dose of the drug has been delivered. FIGS. 49 and 50 are cross sections identical to the cross sections of FIGS. 43 and 44 except FIGS. 49 and 50 are cross sections showing the autoinjector 2500 at the point where the full dose has been delivered.

Figure 54:
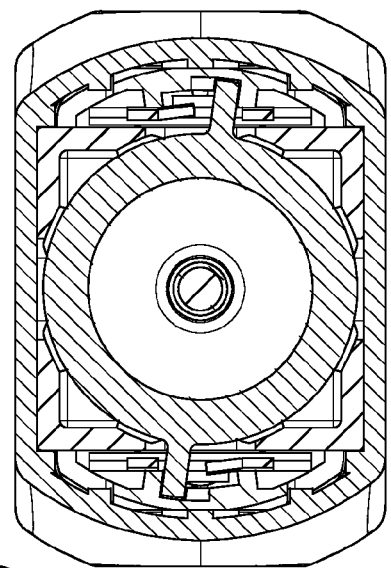
FIG. 54 is a cross sectional view of the autoinjector of FIG. 48 taken along J-J at the end of the dose delivery.
Figure 53:
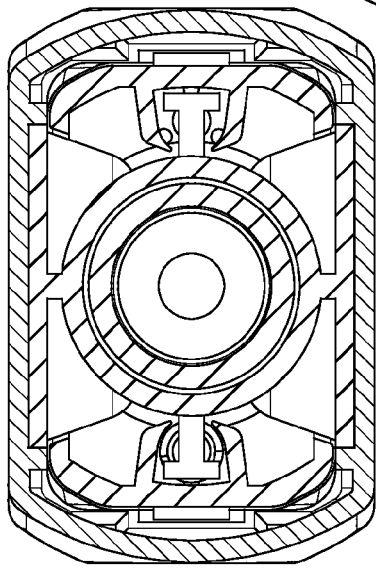
FIG. 53 is a cross sectional view of the autoinjector of FIG. 42 taken along H-H at the end of the dose delivery.
Figure 51:
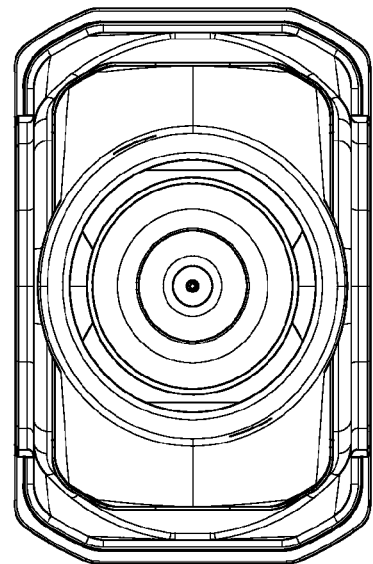
FIG. 51 is a needle end-on view of the autoinjector of FIG. 42 at the end of the dose.
Figure 52:
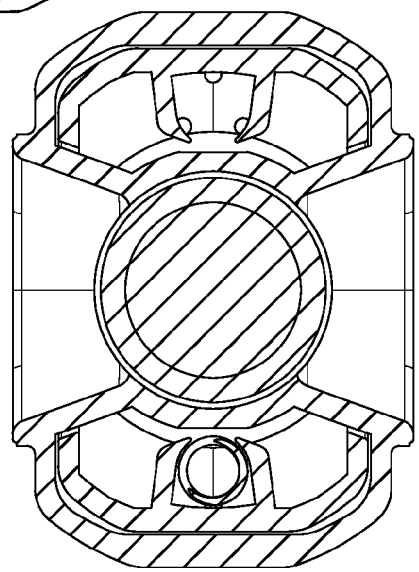
FIG. 52 is a cross sectional view of the autoinjector of FIG. 42 taken along G-G at the end of the dose delivery.

FIG. 51 is a needle end-on view of the autoinjector of FIG. 42 at the end of the dose (and is identical to FIG. 45). Again, for completeness, FIG. 52 is a cross sectional view of the autoinjector of FIG. 42 taken along G-G at the end of the dose delivery, FIG. 53 is a cross sectional view of the autoinjector of FIG. 42 taken along H-H at the end of the dose delivery and FIG. 54 is a cross sectional view of the autoinjector of FIG. 48 taken along J-J at the end of the dose delivery.

As should also be recalled, as described above, some autoinjector 2500 variants can be configured such that, upon full dose delivery, the valve mechanism 120 will not be allowed to fully close. As a result, the "end of dose" situation will initially operate like an "impeded movement" circumstance as described above, but, since the stopper 802 (being at the limit of its allowed travel) cannot move, pressure will continue to build in the region 900 until (assuming an implementation where sufficient pressure is available) the pressure exceeds the force holding the entire power pack 100 in place. As a result, the power pack 100 will be forced away from the needle 804. This "backwards" movement can be used to provide an "end of dose" indication to the user. Since this pressure build up in the region 900 to cause the power pack 100 movement will be relatively quick (on the order of 3-10 seconds depending upon flow restriction, injection speed and trigger pressure $P_t$), as was described above, this indicator to the user that the complete dose has been delivered will be accurate and the user can immediately remove the device.

In fact, by way of an explanatory aside, the ability to provide a end of dose indication in this way can provide is a distinct advantage of such implementations over existing technology. With a conventional spring system and rigid plunger rod autoinjector that provides an end of dose indication, the components are typically arranged so that the release mechanism is activated just prior to the end of the plunger movement, which is before the dose is actually completed. Designers try to make this difference as small as possible, but cannot make it coincide with the true end of dose due to the inherent nature of the mechanical components involved. As a result, most instruction manuals for conventional devices instruct the use to continue to hold the device in the skin for some period of seconds after the end of dose indication is provided to ensure that drug is not still being expelled if the device is removed upon receipt of the indication. In contrast, some implementations of the principles described herein that employ this feature will not suffer from the same problem because the nature of the pressure system is that the sequence will be reversed. The dose will be completed at the lower pressure first, and then (due to the stopper reaching the "end of dose" point) the pressure will build until the trigger pressure ($P_t$) is achieved. Thus, the time required for the pressure to build will necessarily introduce a user-transparent delay between the actual completion of the dose and the indicator being triggered. For example, presume an implementation where the pressure required for a smooth 5 second injection with a 1 mL glass syringe is approximately 15 psi and the worst-case design pressure for a sticky syringe is 40 psi. Further presume that the constant pressure source in the canister 110 is at 80 psi. Thus, if the pressure goes over 40 psi, this can be an indication that either the syringe injection force needed is excessive, or that the stopper has encountered another obstruction, such as the end of the syringe barrel. By assuming that a pressure of 60 psi indicates an unacceptable defect or the end of a complete dose. Upon reaching 60 psi (which could take between about 5 and 10 seconds with the example configuration) it is safe to assume that the injection has been completed. Thus, a mechanism can be included that is calibrated to create an event at 60 psi, such as an audible click signaling that the injection has been completed, retraction of the needle, or some other event, in this example indicating to a user that it is safe to remove the device. FIGS. 55 and 56 are cross sections showing the autoinjector 2500 after an end of dose indication has been given.

With the specific implementation variant shown, the indicator is an audible "click" sound created by the features 22. Specifically, in this example, the features 22 are springs which, in the uncompressed position, are away from the activator body 130. Thus, prior to use, these features 22 will be compressed against the activator body 130 when the power pack 100 is in the pre-use position. However, advantageously, complementary features can be provided on part of the autoinjector in which the power pack is housed such that, when the power pack 100 moves away from the needle 804 by a predetermined amount, the features 22 will no longer be constrained and they will spring out to a more uncompressed state. This movement of the features 22 can directly cause the click by the "snapping" motion, or can trigger some other action that causes the click. As shown, the features directly cause the click through movement past a sharp transition (not shown) and the ends impacting internal locations on the autoinjector that houses the power pack 100. Alternatively, the implementation can be arranged so that the click actually occurs once the force causes the features 22 to release their grip on the housing and forces the power pack rapidly backwards (due to the pressure) causing it to ultimately impact the rear of the housing itself, the audible click being caused by the impact itself. Of course, as will be provided below, neither of these optional approaches are the only way that an end of dose indicator can be provided.

Figure 60:
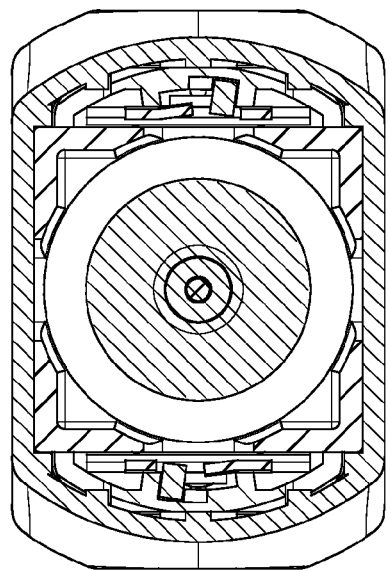
FIG. 60 is a cross sectional view of the autoinjector of FIG. 48 taken along J-J following the indicator "click" being provided.
Figure 59:
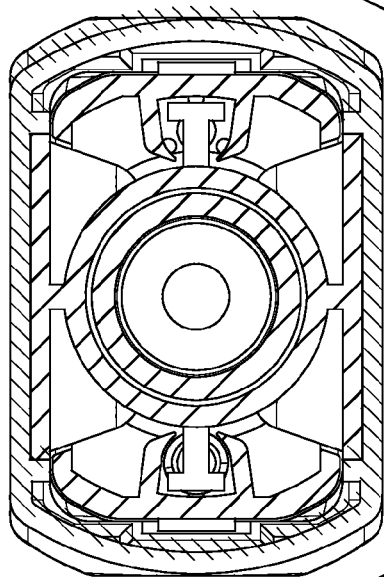
FIG. 59 is a cross sectional view of the autoinjector of FIG. 42 taken along H-H following the indicator "click" being provided.
Figure 57:
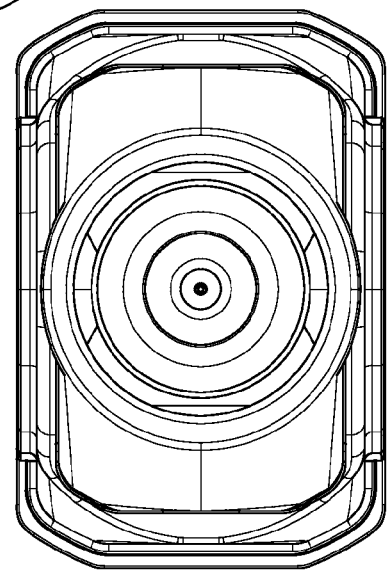
FIG. 57 is a needle end-on view of the autoinjector of FIG. 42 following provision of the indication.
Figure 58:
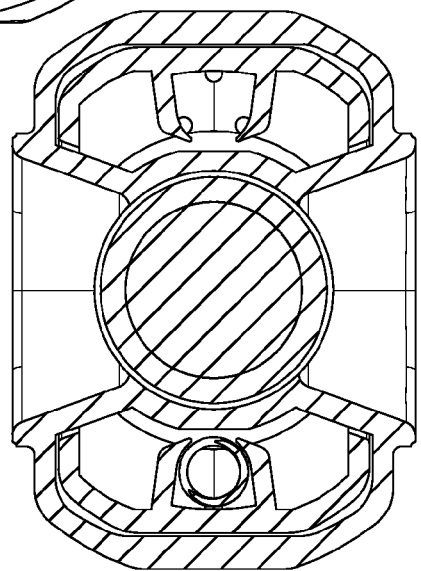
FIG. 58 is a cross sectional view of the autoinjector of FIG. 42 taken along G-G following the indicator "click" being provided.
Figure 61B:
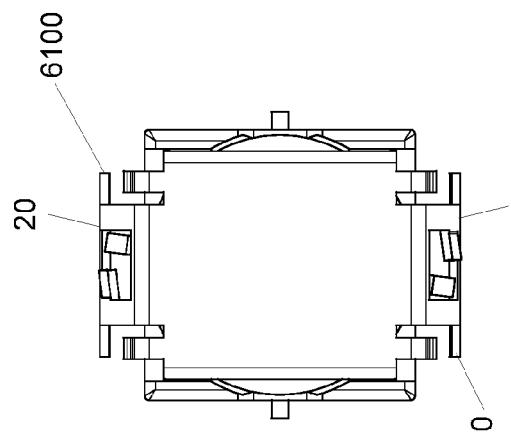
Figure 61D:
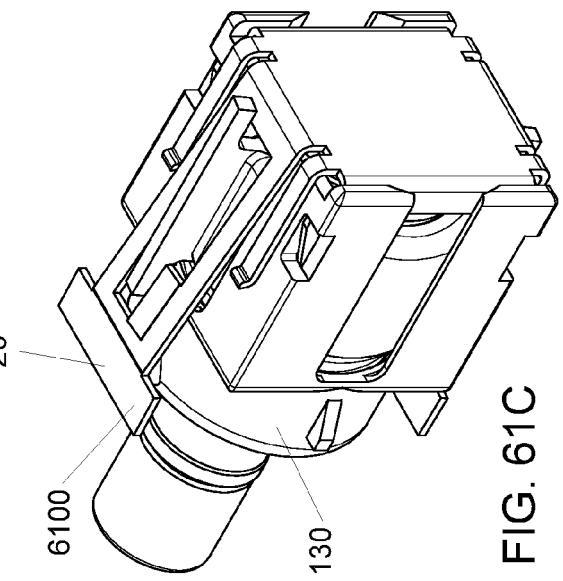
Figure 61A:
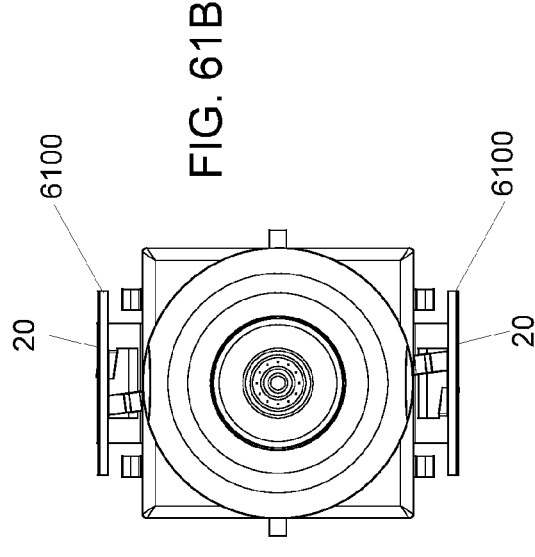
Figure 61C:
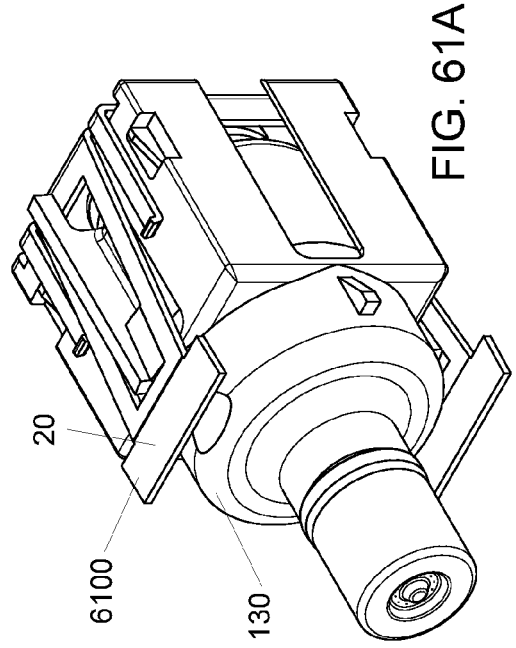

FIG. 57 is a needle end-on view of the autoinjector of FIG. 42 following provision of the indication. Again, for completeness, FIG. 58 is a cross sectional view of the autoinjector of FIG. 42 taken along G-G following the indicator "click" being provided, FIG. 59 is a cross sectional view of the autoinjector of FIG. 42 taken along H-H following the indicator "click" being provided and FIG. 60 is a cross sectional view of the autoinjector of FIG. 48 taken along J-J following the indicator "click" being provided.

Presumably, upon receiving the indicator, the person will withdraw the autoinjector 2500 which, in turn will remove the needle 804. This will relieve the compression pressure on the internal spring 3502 causing the shield 3302 to deploy out of the main body 2502 and, from an external view, this will result in the autoinjector 2500 having an external configuration identical to the configuration of FIGS. 33 and 34.

Internally however, with this variant autoinjector 2500, the configuration will be slightly different.

Specifically, it will be recalled from FIGS. 1A-1H, that the example power pack 100 included additional features 20, 22. With the variant autoinjector 2500, one of the features 20 serves an additional purpose. With this variant, the feature 20 is actually made of a spring metal. In that regard, FIGS. 1A-1H (among others) illustrate feature 20 in a compressed position. In contrast, FIGS. 61A-61H illustrate the power pack 100 of FIGS. 1A-1H when the feature 20 is in the "uncompressed" or "released" state wherein the end 6100 of the feature 20 are moved away from the activator body 130.

With this backdrop, the remaining operation of the example autoinjector 2500 variant can now be described.

FIGS. 62 and 63 are cross sections of the autoinjector 2500 respectively taken along E-E of FIG. 33 and F-F of FIG. 34 in this final state. As can be seen in FIG. 62, the shield 3302 has deployed out of the main body 2502 and, the power pack 100 has moved to a position 6202 farthest from the needle 804. In this position, the feature 20 is aligned with a recess 6204 in the main body 2502 and not otherwise constrained. The end 6100 of the feature 20 is thereby enabled to move into the recess through transition of the feature 20 to its "uncompressed" or "released" state. Notably, in this position, the feature will, thereafter, block the portion 3304 from moving in a direction closer to the end of the autoinjector farthest from the needle 804. As a result, since the portion 3304 is coupled to the shield 3302, the feature 20 acts as a lock that maintains the shield in its extended position and thereby acts to prevent easy access to, or unintended contact with, the needle 804 after use.

Figure 67:
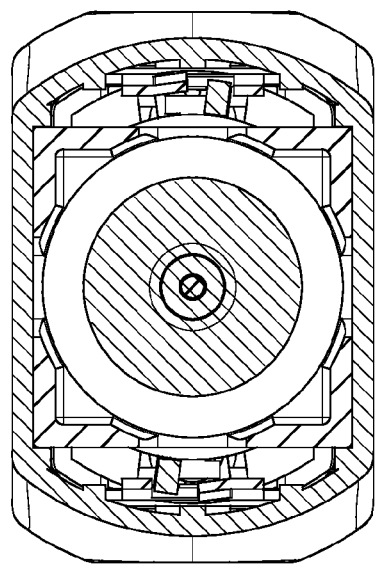
FIG. 67 is a cross sectional view of the autoinjector of FIG. 34 taken along J-J when internally in the "lock out" position.
Figure 66:
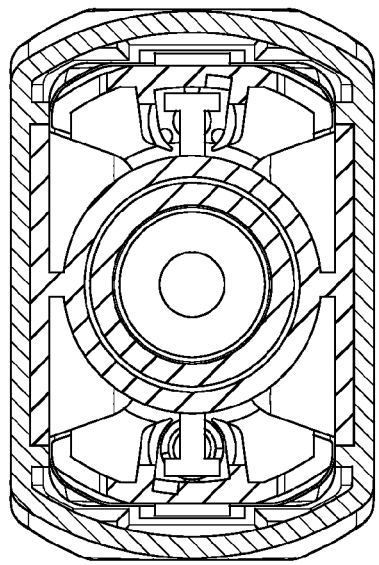
FIG. 66 is a cross sectional view of the autoinjector of FIG. 34 taken along H-H when internally in the "lock out" position.
Figure 64:
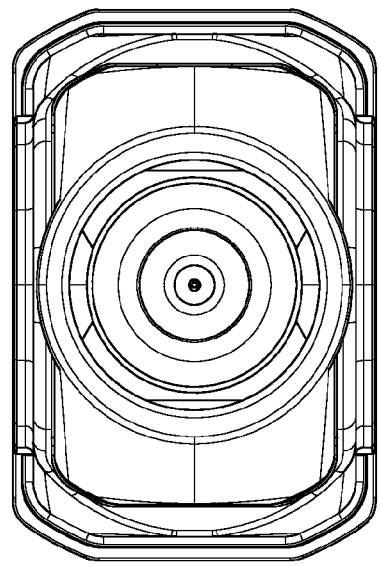
FIG. 64 is a needle end-on view of the autoinjector after the lock feature has been activated.
Figure 65:
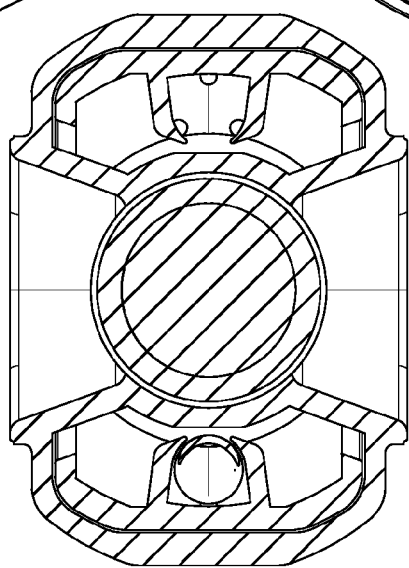
FIG. 65 is a cross sectional view of the autoinjector of FIG. 34 taken along G-G when internally in the "lock out" position.

FIG. 64 is a needle end-on view of the autoinjector 2500 after the lock feature 20 has been actuated (the "lock out" position). Again, for completeness, FIG. 65 is a cross sectional view of the autoinjector of FIG. 34 taken along G-G when internally in the "lock out" position, FIG. 66 is a cross sectional view of the autoinjector of FIG. 34 taken along H-H when internally in the "lock out" position, and FIG. 67 is a cross sectional view of the autoinjector of FIG. 34 taken along J-J when internally in the "lock out" position.

Alternative Variants

Although various aspects of the instant approach have been described using certain specific example implementation variants, by no means is the approach intended to be limited to such variants. Different variants can be constructed using various permutations and combinations of various components described herein.

For example, although the regulation of the flow rate of the driver was described above as involving outlet(s) 146, other approaches can be alternatively be used because there are many methods available for regulating the flow rate of gases, most based on placing an inline restriction that the gas must pass through, particularly considering the relatively low flow rates needed for the small injection volumes typical for the classes of devices to which the description herein applies. By way of example, regulation of the driver flow rate can be accomplished using, for example: (1) a permeable membrane made of, for example, plastic, fiber, a microporous film (by way of non-limiting example, Celgard® Commercial Monolayer Polypropylene (PP) Separators commercially available from Celgard, L.L.C., 13800 South Lakes Dr., Charlotte, N.C. 28273, for example, the Celgard® 2500 micron thick monolayer polypropylene), (2) a sintered porous metal, porous metal foam, porous ceramic or porous ceramic foam, or other solid, but porous material, or (3) a suitable material containing orifices other than round holes, for example, slots, conic sections, rhombuses or other regular or irregular closed polygons, formed by any suitable process including etching, drilling (physical or laser), micromilling, etc.), the important aspect being that the material be of a type that will not adversely react with the driver and is porous in a manner such that it is capable of modifying the flow rate of the driver on the output side to the desired flow rate within the space available in the particular design during use.

Similarly, the canister of an autoinjector constructed in accordance with the teachings herein can be made of any material that will not adversely react with the driver, can be configured to withstand the maximum driver pressure during storage (which may include accounting for or insulating from temperature fluctuations), and has an acceptable permeability rate, and hence pressure loss (based upon the specific driver to be used) over the intended shelf-life of the device. Thus, example materials suitable for use as the canister include certain plastics, metals and glass.

For example, there are specific advantages that can be achieved using molded plastic resins for the canister, such as lower overall cost and the ability to easily integrate different physical features into the components, thus reducing component count and device size. One representative, non-limiting example of a specific suitable plastic for the canister is a plastic known as "Polyamide MXD6" (PAMXD6) which is commercially available under the Reny brand from Mitsubishi Engineering-Plastics Corp., which has a current presence in the U.S. through MEP America, Inc., 420 Lexington Avenue, Suite 219, New York, N.Y. 10170.

Alternatively, the canister can be made from a metal, including, by way of non-limiting example, drawn or machined steel or aluminum cartridges which can be configured to have a valve or pierce-able or frangible area included inside, attached to it or associated with it for exit of the driver. For ease of manufacture, the canister can be made of multiple pieces that can be joined together, provided the joint has an appropriately strong bond between pieces. Such joints may be formed by, for example, gluing, spin-welding, brazing, or other appropriate joint forming method.

Moreover, for some implementations, it may be desirable to use one or more ampoule-like glass capsule(s) containing a small amount of liquefied gas driver. With such a configuration, release of the driver can be accomplished by fracture of some portion capsule. Such a configuration could provide advantages in terms of simplicity and cost in some implementations.

As a further extension, particular implementations, could straightforwardly involve use of a canister with two or more chambers or two or more different canisters, which have different pressure drivers. Such a configuration can provide further advantages in multi-dose configurations or where mixing of constituents of the drug to be given must be stored separately and mixed a nominal time before injection.

Different variants may also employ alternative approaches to driver release.

For example, the canister may have a valve that can be opened and closed, such as for use when regulating the pressure or other purposes, such as re-sealing prior to emptying of the canister is desired. An advantage to configurations that use a valve is that it can also be used for the canister-filling process.

For a canister that does not need to be resealed or otherwise opened and re-closed, release of the driver can be accomplished by piercing or breaking the canister in some way. Approaches for releasing a gas from a container are well known, so the selection of the particular approach for doing so in the particular configuration will be non-inventively straightforward. Such configurations could provide additional benefits not obtainable with some valve configurations. For example, permeable canister materials could be avoided entirely thus eliminating the possibility of driver volume and/or pressure loss over time and, in some cases, could result in minimizing required driver volume. In addition, fewer parts may be needed with such an approach, which consequently reduces cost and potentially size, while likely increasing reliability. Filling of a canister of this design can be accomplished, in different known manners, including for example, by providing a small hole in the canister which is plugged with a precision steel ball and can be employed with both metal and non-metal canisters.

Figure 68C:
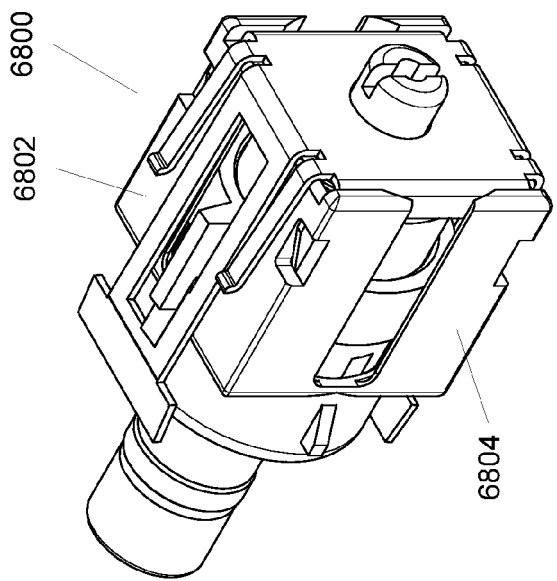
FIGS. 68A-68D respectively illustrate, in simplified form, different exterior views of one example of a representative inventive power pack employing some variant aspects.
Figure 68D:
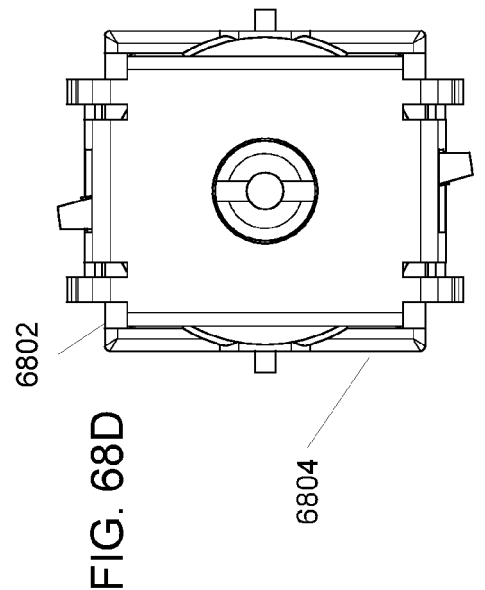
Figure 68A:
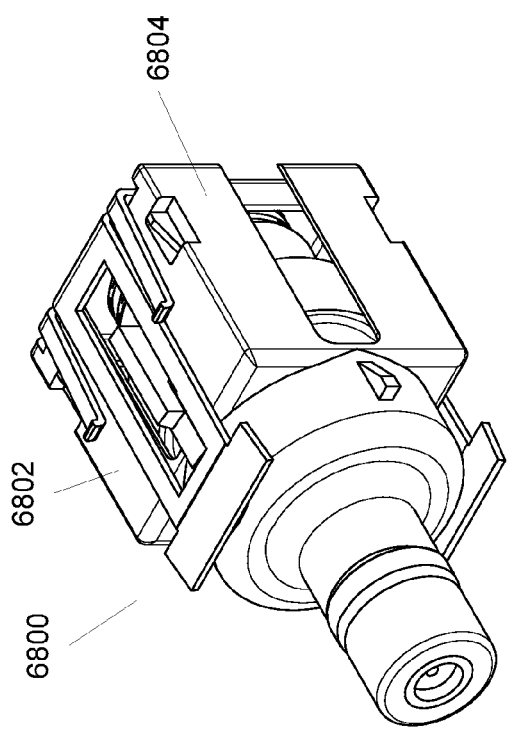
Figure 68B:
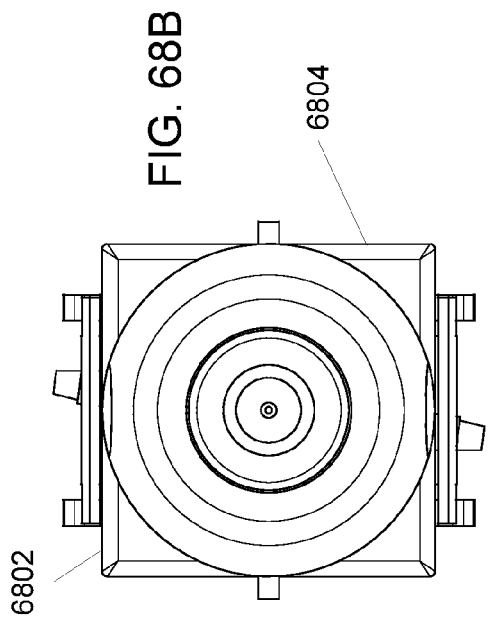

FIGS. 68A-68D respectively illustrate, in simplified form, different exterior views of one example of a representative inventive power pack 6800 employing some of the variant aspects described above. Specifically, FIG. 68A is a front perspective view of the power pack 6800, in which the upper face 6802 is the same as the lower face (not shown) and the right face 6804 is the same as the left face (not shown). FIG. 68B is a front plan view of the power pack 6800. FIG. 68C is a rear perspective view of the power pack 6800 and FIG. 68D is a rear plan view of the power pack 6800.

Figure 69:
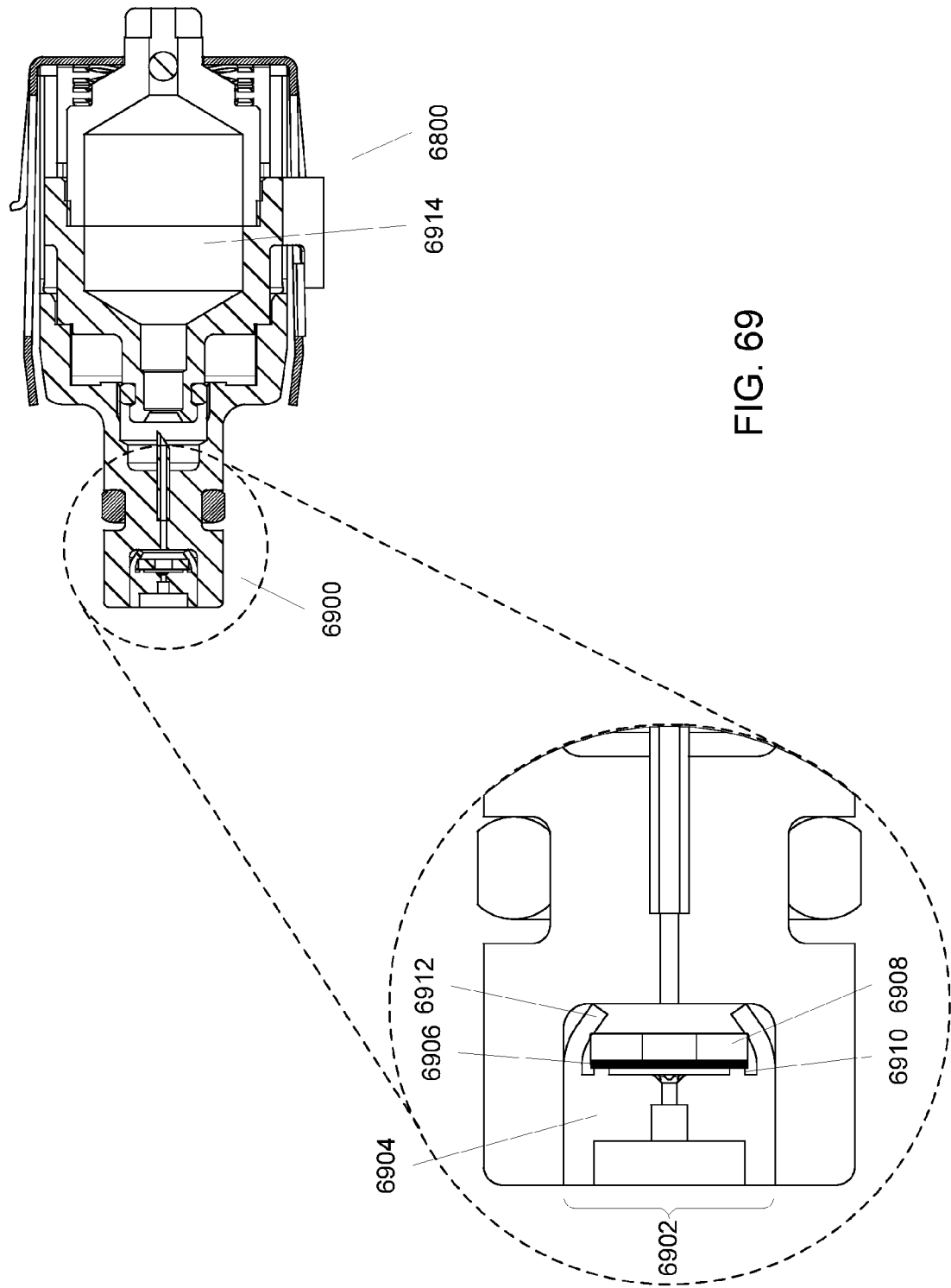
FIG. 69 illustrates, in simplified form, a representative cross section of the power pack with the exhaust end enlarged to better illustrate the details of this variant flow regulator.

FIG. 69 illustrates, in simplified form, a representative cross section of the power pack 6800 with the exhaust end 6900 enlarged to better illustrate the details of this variant flow regulator 6902. Specifically, this example implementation flow regulator variant is made up of a flow regulation body 6904 which, advantageously, is configured so that it can be constructed separately and then installed within a part the exhaust end 6900. As shown, the flow regulation body 6904 is designed to (and, as shown is) tightly pressure fit into the exhaust end 6900. The example flow regulation body 6904 shown also includes a microporous membrane 6906, such as described above, which is specifically used to regulate the flow. The membrane 6906 is held in place by a washer 6908 which sandwiches the membrane 6906 between itself and a ring-shaped feature 6910 of the flow regulation body 6904. In this implementation example, tabs 6912 (or other element) on the innermost periphery of the flow regulation body 6904 are used to constrain the washer 6908 (and consequently the membrane 6906) in place such that driver exiting the canister 6914 must pass through the membrane 6906 before exiting the power pack 6800.

FIGS. 70A and 70B respectively show the upper face and right face of the example power pack 6800 implementation in its initial state. FIG. 70C is a cross sectional view of the power pack 6800 taken along K-K of FIG. 70A and FIG. 70D is a cross sectional view of the power pack 6800 taken along L-L of FIG. 70B. As can be seen in FIGS. 70C and 70D, this power pack variant is somewhat different from the commercial variant described previously. Those differences will now be described.

Specifically, the reservoir 7002 of the canister 7000 in this variant is primarily shaped like a cylinder capped at either end by two conic sections. In this variant configuration, the canister 7000 is made of two pieces of metal, a front piece 7004 and a back piece 7006 which are joined together, specifically, the front piece 7004 and back piece 7006 are machined aluminum joined by spin welding. Behind the canister 7000 is a spring 7008, in this case a wave spring, located and constrained as described above, that is similarly designed to urge the canister 7000 forward within the power pack 6800 upon activation. The back piece 7006 includes a fill valve 7010 (such as a ball check style valve or an opening that can easily be plugged after filling to seal against driver leakage), through which the canister can be filled with a driver, in this case a compressed or liquefied gas, and then be sealed.

The front piece 7004 includes a relatively thin portion 7012 that is thick enough to avoid rupture under the force exerted, post-filling, by the driver, but thin enough to easily be pierced by, for example, a sharpened angle-cut tube 7014 such as shown or any other geometry or element, the important aspect being the ability to pierce to release the driver while allowing the driver to pass and exit the power pack 6800.

Figure 70E:
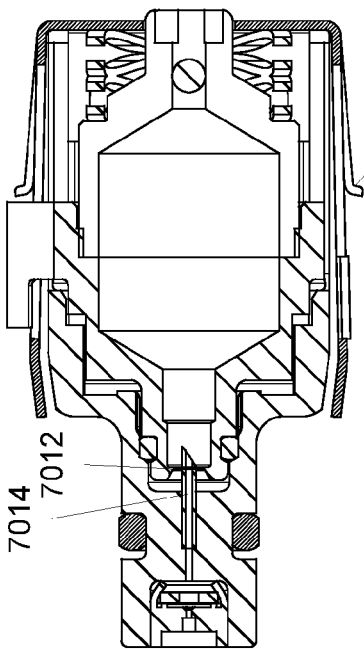
FIGS. 70E and 70F respectively are cross sections of the power pack in the "activating" state.
Figure 70G:
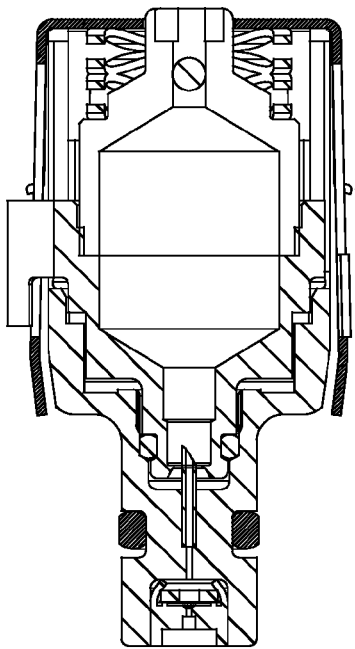
FIGS. 70G and 70H respectively are the cross sections of the power pack when the power pack has reached the "end of dose" state.
Figure 70F:
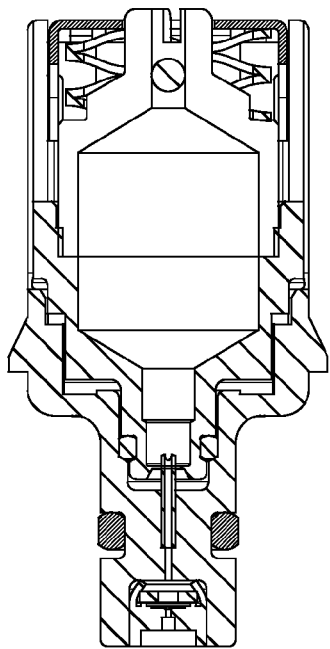

FIGS. 70E and 70F respectively are the cross sections of the power pack 6800 when the power pack 6800 is in the "activating" state. As can be seen, entering the "activating" state causes the power pack 6800 to move forward such that the tube 7014 pierces the portion 7012, allowing the driver to exit the power pack 6800 at about full (i.e. canister-level) pressure, but with its flow rate regulated by the membrane 6906.

Figure 70H:
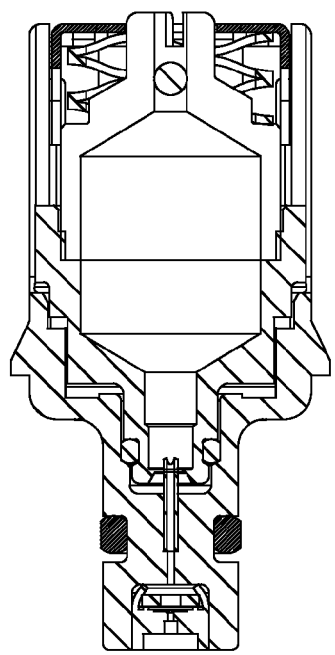

FIGS. 70G and 70H respectively are the cross sections of the power pack 6800 when the power pack 6800 has reached the "end of dose" state. In this state, most of the components of the power pack 6800 are in the same place. However, in this state, the features 22 have been compressed due to the driver pressure build-up that will force the power pack backwards (i.e. away from the needle end of the autoinjector with which it is associated.

Figure 70J:
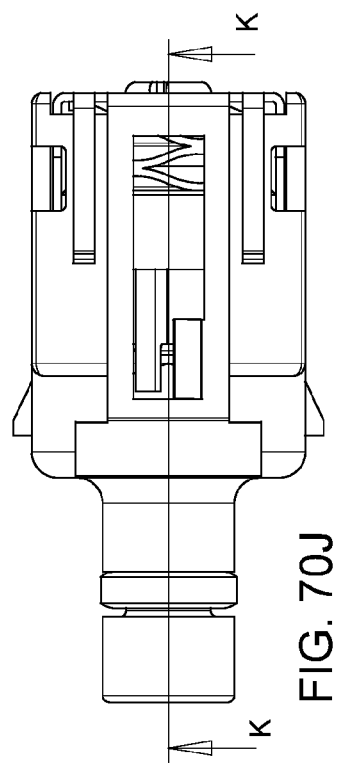
FIGS. 70J and 70K respectively show the upper face and right face of the example power pack implementation in its "final" state.
Figure 70L:
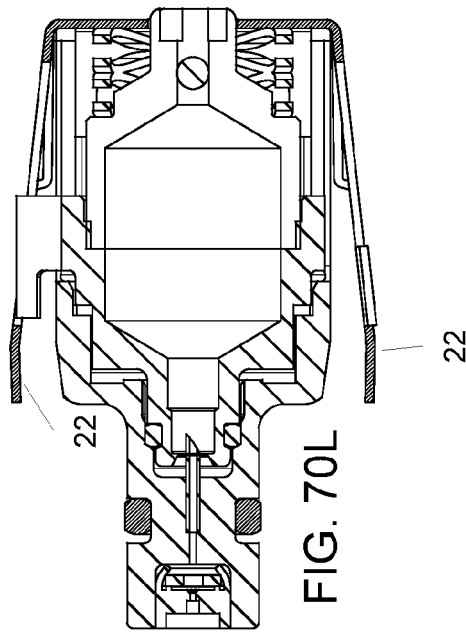
FIG. 70L is a cross sectional view of the power pack taken along K-K of FIGS. 70A and 70J.
Figure 70K:
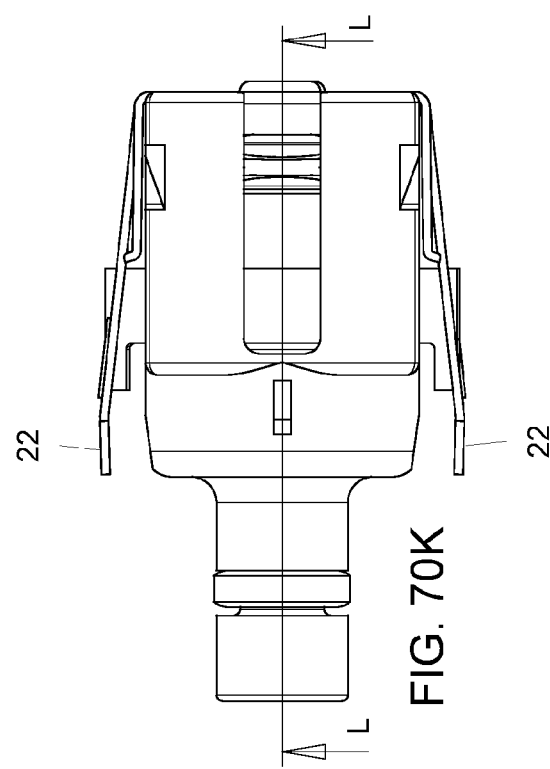
Figure 70M:
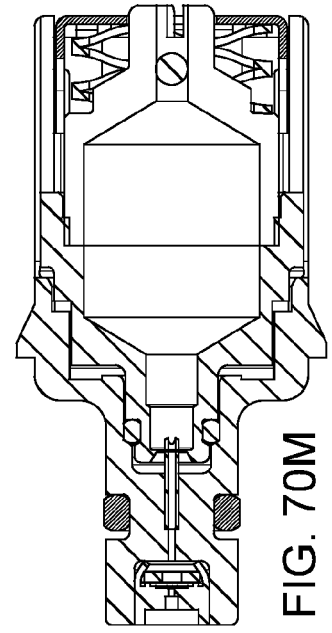
FIG. 70M is a cross sectional view of the power pack 6800 taken along L-L of FIGS. 70B and 70K.

FIGS. 70J and 70K respectively show the upper face and right face of the example power pack 6800 implementation in its "final" state. (Note: to avoid confusion between an "I" and a "1", no "FIG. 70I" is used) FIG. 70L is a cross sectional view of the power pack 6800 taken along K-K of FIGS. 70A and 70J, and FIG. 70M is a cross sectional view of the power pack 6800 taken along L-L of FIGS. 70B and 70K. Again, this "final" state configuration is essentially the same as the "end of dose" configuration of FIGS. 70G and 70H except that, at this point, the movement of the power pack 6800 backwards will have reached a point where the holding force of the spring-like features 22 is exceeded allowing the power pack to move to a new position under pressure.

As should now be appreciated and understood in a general sense, the essence of the technology described herein is a power pack device that uses a driver, in the form of a constant pressure gas as a pressurized fluid energy source (as opposed to a mechanical drive energy source), to expel a specified dose from a drug container in a compact drug delivery device while making it possible to provide features which are ordinarily expensive to provide, somewhat unreliable, and bulky to implement, in a purely mechanical system. In addition, power pack implementations conforming to the generic approach can provide advantages that are valuable and/or cannot be cheaply or reliably provided with conventional autoinjectors, if they can be provided at all.

For example, as noted with respect to the specific implementation above, when using a flow regulator with the constant pressure source, the rise in pressure that occurs upon encountering obstructions, if the constant pressure source has sufficient pressure overcome the highest expected resistance during a normal injection, can be used to trigger events that are valuable in an auto injector. Other features and functions that could take advantage of this delayed rise in pressure can be straightforwardly and reliably implemented include: other end of dose feedback (audible or visual), retraction of the needle, activation of a needle shield, activation of another stage (in a multi-stage device), priming, dual chamber cartridge mixing and resetting for a repeat dose.

One advantage that can be obtained by some implementations is a reduction in syringe force during the injection and, thus, reduced risk or elimination of, syringe glass breakage. Syringe failure via glass breakage is a common problem with mechanical spring-based autoinjectors. With such devices, when activated, the spring and plunger are released suddenly and accelerate in space for some distance until impact with the syringe stopper occurs. This causes an impulse force on the syringe that is occasionally strong enough to break the glass flanges of the syringe. In contrast, with many implementations using the instant approach, there is no unrestrained high velocity moving mass to cause an impact, and gas pressure increases gradually, so the possibility of such breakage is reduced, if not eliminated.

Moreover, loud noise and vibration during activation are often byproducts of the sudden acceleration common to mechanical spring-based autoinjectors and are generally considered undesirable in needle-based injection systems. In contrast, implementations using the instant approach have no impact, which can translate to elimination of such undesirable noise and vibration, even though there may be some noise associated with activation.

A further variant, usable with implementations that include a window such that at least some portion of the needle end of the body of the syringe is visible, can be constructed that can provide a visual indication of the end of a dose. With such variants, a colorant is added to the driver. As the driver fills the syringe body behind the stopper and the stopper moves towards the needle, the colored driver will become visible. With proper placement of the window area, a window that changes color (due to presence of the colored driver and stopper position) can be a visual indication of the end of a dose.

Up to now, most of the variants that have been described involve, in use, direct application of force by the driver to deliver the dose, whether by moving a stopper of a syringe, collapsing a drug containing pouch, or by inflating a pouch or otherwise increasing pressure in one part of a container to drive the drug out another part. However, in some cases it may be necessary of desirable to include some form of physical intermediate member between the exhaust of the power pack and the stopper or other element that acts directly on the drug to be injected. Depending upon the particular application and implementation, such an intermediate member might be one or more of: a simple close-ended tube or cup that slides and pushes directly on the syringe stopper or flexible drug container), or alternatively, moves while sealed against the drug container, a plunger rod, a telescoping column (damped or undamped), a flexible piece such as a ribbon that unfolds or unwinds, a collapsible bellows, etc., or it might be a more complex member that itself contains some mechanism or can absorb part of the driver pressure to effect some other action. A few non-exhaustive examples of applications that can advantageously be provided using such an intermediate member include: for pre-loading a spring that will later retract the needle or deploy a needle shield, trigger an end of dose indication or dose progress either visually or audibly, to cause a pre-mixing of dose components by dispensing the components from chambered cartridges and interrupting stopper movement after the mixing but prior to injection into the patient, enable a dose stop feature (i.e. for precise dosing of only part of the syringe contents (0.3 mL from a 1 mL filled syringe, for example), or other appropriate or desired action.

In addition, some syringe stoppers are known to have a large diameter to depth ratio. With such stoppers, the use of a gaseous driver to directly move the stopper could be problematic in some cases because, if one part of the stopper's periphery encounters higher friction, the stopper could rotate and either jam or also possibly compromise the seal. Advantageously, an intermediate member can be used to avoid this issue. To do so, the intermediate member would be configured to contact the stopper in a way that mimics a traditional syringe plunger rod at the stopper and thereby stabilizes and provides proper guidance for the stopper. FIG. 71 illustrates, in simplified form, one example of an intermediate member 7100 to address this issue and which, in this example implementation, is made up of three parts. The first part 7100a is sized and shaped to be inserted into, and conform to, the interior of a syringe stopper 7102. The second part 7100b is sized such that the stopper end of that part 7102b is substantially as wide as the stopper itself. The third part 7100c is configured to enclose at least a portion of the second part 7100b and be movably sealed to the second part 7100b by a seal 7104 such that a sealed chamber 7106 is formed between the two into which driver can flow via an inlet 7108 configured to accept the exhaust end of a power pack as described herein (not shown) to drive the stopper away from the power pack without allowing the stopper to pivot in a way that compromises the seal to the drug being delivered.

Still further, an intermediate member can be used to provide mechanical speed regulation in cases where flow regulation may not be suitable, for example, in cases where extremely slow injections are desired. In addition, in some cases other means of speed regulation may also need to be mechanically or hydraulically coupled to the intermediate member.

Another use for an intermediate member is for pre-delivery drug mixing or multiple dose delivery. FIG. 72 illustrates, in simplified form, an alternative example intermediate member 7200 that can be used for one of these purposes. As shown, the intermediate member 7200 includes a housing 7200a which surrounds a rod 7200b inserted therewithin. As with FIG. 71, a seal 7202 is used within the housing 7200a to seal the housing 7200a to the rod 7200b. The seal 7202 is positioned in a manner that allows driver from a power pack 7204 to exert pressure within a chamber 7106 formed between the two to move the rod 7200b relative to, and within, the housing 7200a to drive a stopper 7206 forward. The rod 7200b also includes at least one detent 7208 with which a pawl 7210 can interact to halt the movement of the rod 7200b, for example, unless (or until) some further action occurs. In this manner, in the initial case, the movement up to the point the pawl 7210 catches on the detent 7208 can be used to, for example, mix drug components or provide an initial dose. A further action, which may be based upon build up of driver pressure or some other occurrence, can then cause, in the case of drug component mixing, delivery of a dose of the mixed drug, or, in the case of a multiple dose device, delivery of a subsequent dose.

As an aside, as shown in FIG. 72, the intermediate member 7200 also optionally includes a speed regulation device 7212, in this case a hydraulic damper 7214 coupled to the rod 7200b as described above.

Yet another application in which an intermediate member may be advantageously employed is for automatic penetration. To implement this approach, a plunger rod that is detented against the drug container is used to allow gas-driven penetration. Upon activation, driver causes the syringe to move with the plunger rod until the plunger rod reaches full penetration. At this point, an artificial "blockage" condition occurs, causing the pressure to build until sufficient force is present to decouple the plunger rod from the syringe, allowing the injection to begin. This approach may specifically be advantageous when stopper glide forces are very low and the stopper needs to be undisturbed until full penetration has occurred.

Finally, some may recognize from the description above that some variants may have an issue with respect to pre-pressurizing of the volume between the syringe stopper and the power pack's seal (the "trapped volume"). At some point, a significantly complete seal must be present. The seal may be created during assembly, or at the time of activation. If the seal is created during assembly of the power pack to the syringe, in many cases there will be pressure created due to the displacement required to engage the seal on the inside of the syringe barrel. This is potentially undesirable because this pressure, if sufficiently high, may cause fluid to leak out of the syringe or, more likely, will cause syringe contents to partially expel when the sterile cap over the needle is removed. This is undesirable, not only because it could be a nuisance, but because it can be wasteful of an expensive drug and, in general, is considered objectionable for this class of devices.

One conceptual approach to dealing with this potential issue is venting of the trapped volume. Venting the trapped volume, if it is significantly large, may even be desirable even if there is no initial pressure build up, because of the possibility that the device will likely experience atmospheric pressure changes during the time between manufacture and use, such as changes due to altitude.

Advantageously, there are several potential alternative solutions that can be used to minimize or avoid the problem.

If the seal is created during assembly, one approach is to allow for a very slight "breathing" of the "trapped volume" in order to allow release of pressure over a length of time, but be insignificant during the length of a typical injection. This approach can be implemented using any one or more of a permeable seal material, a flow restrictor, an interrupted sealing surface, etc. However, this approach may be unsuitable for use with certain drivers, namely those which should not be released into the atmosphere during and/or after activation. Thus, for such an approach, a driver should be selected that is reasonably inert and acceptable to be released into the atmosphere in the quantities at issue. One example driver fitting this category is R134a, which is used in pressurized-metered dose inhalers. Drivers such as some hydrocarbon propellants are commonly released to the atmosphere in small quantities, for example, propellants used in aerosol cans. Since the quantity of driver used in an auto-injector is far less than the amount of propellant expelled during use of a typical aerosol can, those propellants may be acceptable as drives for some implementations as well. However, it should be recognized that flammability issues with those drivers may make them unacceptable for certain applications or environments.

Another alternative solution that can be used with some implementations is to create a full seal between the syringe and power pack during assembly, but allow venting within the power pack while in the un-activated state. A seal somewhere between the canister front and the syringe can be arranged to be un-engaged from a vent (for example, bypass vent 154 of FIG. 1G; or bypass vent 7016 of FIG. 70D) until activation, at which point the forward movement of the canister during activation in the case of the implementations of FIGS. 27-67, or some other action for other implementations, also causes the seal to close off or isolate the vent, ensuring that the driver will not exhaust out the vent during the intended use as long as the canister remains in the forward position or, with the other implementations, the seal remains closed.

Yet a further alternative, similar to the preceding one, is to create the seal between the syringe and exhaust end of the power pack upon activation by, upon activation, causing the power pack to move towards the needle such that a seal is formed between the syringe and exhaust end of the power pack at the limit of that movement. This could be accomplished in various ways, such as engaging a radial seal (u-cup, o-ring, etc.), an axial seal (such as a tapered "cone" that seals at the opening of the syringe), or through some other mechanism between the two, the important aspect being the creation of the seal so that driver does not leak out as opposed to the type of seal formed or how the seal is implemented.

Having described certain specific implementations and implementation variants of the power pack approach, the foregoing power pack approach can be implemented generically in any one of four approaches. FIGS. 73-76 illustrate, in the most generic form, several power pack approach variants that form the innovative approach described herein.

Specifically, FIG. 73 illustrates, in generic form, the simplest version power pack 7300 usable to employ the instant approach to delivering a drug from its container 7302 via a needle 7304. With this variant, the power pack 7300 is essentially made up of a canister 7306 that contains the driver 7308 (which will typically be a liquefied gas with a moderate vapor pressure, meaning one that is high enough to push past any expected "sticky" point or obstruction, for example due to sticky or high break-loose forces, siliconization or other issues). This approach is best used for implementations where the "syringe" to "syringe" variability and/or performance is consistent or for "syringe" variants that use pouches such that there is no issue of stickiness or break-loose force at all, so that no further control is required. With this variant, the constant pressure from the canister generates a smooth, consistent injection without need for a pressure regulator or flow regulator. Note also that, with this variant, the constant pressure is always fully acting on stopper or other actuator that forces the drug out the needle. In other words, if the canister vapor pressure is 50 psi the actuator will be exposed to 50 psi of pressure. Advantageously, this is the simplest and likely cheapest configuration. However, with this approach, the pressure must be sufficient to apply the maximum force necessary and will likely provide the fastest injection relative to the next three generic variant (all other things being equal).

FIG. 74 illustrates, in generic form, a more complex alternative version power pack 7400 usable to employ the instant approach to delivering a drug from its container 7402 via a needle 7304. With this variant, the power pack 7400 is essentially made up of the canister 7306 as before, which contains a driver 7402 of a pressure much higher than the maximum force that could be needed to deliver the drug under the greatest margin of error (i.e. stickiness, break-free, deviation or obstruction) situation. In addition, with this configuration, the power pack 7400 also includes a pressure regulator 7404 which reduces the pressure to some intermediate pressure that is still high enough to push past any expected "sticky" point or obstruction, for example due to sticky or high break-loose forces, siliconization or other issues). Again, the constant pressure at the output of the regulator 7404 can be considered as having the same operation as the "canister-only" configuration of FIG. 73, and the constant pressure output from the regulator, albeit lower than canister 7306 pressure of this power pack 7400, will provide a smooth, consistent injection.

Since many drug container 7302/needle 7304 combinations only require application of a relatively low pressure to deliver a drug dose, one advantage of using this pressure regulator configuration is that it allows use of a high pressure liquefied gases such as $CO_2$ if a pressure level is needed that is greater than necessary to deliver the dose, for example to overcome significant obstruction or to use the higher pressure for some other purpose. Depending upon the particular implementation, the regulated pressure will be much lower for normal drug delivery, so it can be configured to act directly on a stopper or flexible bladder, etc., or indirectly via an intermediate member, but higher pressure can be available for some other purpose.

FIG. 75 illustrates, in generic form, a more complex version power pack 7500 usable to employ the instant approach to delivering a drug from its container 7302 via a needle 7304. With this variant, the power pack 7500 is essentially made up of the canister 7306 as before, which contains a driver 7402 of a pressure moderately higher than the maximum force that could be needed to deliver the drug under the greatest margin of error (i.e. stickiness, break-free, deviation or obstruction) situation. However, because this moderate pressure may be high enough to cause the syringe to inject too quickly in some variants, with this configuration the power pack 7500 also includes a flow regulator 7502. The flow regulator 7502 is configured to meter the amount of driver that can pass out of the power pack 7500, thereby restraining and controlling the rate at which the driver 7402 can exit the power pack to a desired level, resulting in a speed controlled and slower injection than would occur in the power pack 7500 without the flow regulator 7502.

Advantageously, with this configuration, the flow restrictor 7502 limits the pressure applied to deliver the drug during normal injection but, as with the configuration of FIG. 74, the pressure increases when an "obstruction" condition exists. For example, if the driver 7402 in the canister 7306 is at 80 psi, but the pressure needed for a normal injection is 15 psi, the rate the driver 7402 exits the power pack 7500 will be regulated so that it cannot exit as quickly, with the net effect being a gentler application of pressure (which appears from the drug perspective to be close to 15 psi) during normal injection, but up to the full 80 psi is available as a margin of error or to be used for some other purpose, like triggering some other action, for example, as previously described.

FIG. 76 illustrates, in generic form, a the most complex generic version power pack 7600 usable to employ the instant approach to delivering a drug from its container 7302 via a needle 7304. This variant power pack 7600 is a generic version of the specific implementation of FIGS. 27-67 in that it includes the canister 7306, pressure regulator 7404 and flow regulator 7502. As a result, this configuration can provide advantages available in the configuration of FIGS. 73 through 75 while allowing for use of a broader range of pressures for the driver 7402.

It should now also be specifically appreciated that implementations of both the generic configuration of FIG. 74 and the generic configuration of FIG. 76 can provide one or more of the following advantages. They can allow for slow injection during normal resistance but provide increased force when necessary during dose delivery but, when an "obstruction" condition occurs, the pressure can increase (theoretically, until equilibrium with the canister pressure is reached). Moreover, since it will take a finite amount of time for the pressure rise, these configurations can allow for some intermediate (i.e. between unobstructed normal and full canister) pressure level to be used for some other action, for example, initiating a sequence or event that takes into account, and advantage of, this inherent delay. One example of such an approach is to use the intermediate pressure to trigger auto-retraction of the needle at the end of the dose but it prevents a "wet" injection because, the inherent delay between the end of the dose and reaching the pressure that causes the needle retraction to occur, provides certainty that the injection will not still be occurring when needle is withdrawn. Another example, is to use an intermediate pressure to provide an audible, visual or tactile indication that the injection is complete, with the inherent delay for pressure build up reliably ensuring that this is the case.

Having described various aspects of different variant power packs and components that can be used in conjunction with those power packs to deliver a dose of a drug or provide other advantages, a further aspect will now be described which is wholly independent of, but usable with, autoinjectors as described herein. This aspect relates to an apparatus for use with the needle shield that comes on a pre-filled syringe. The apparatus allows the shield to be maintained in place when the syringe is loaded into the autoinjector and be removed and replaced, when the autoinjector cap is removed, thereby preserving safety and sterility during loading and before and after use. In that regard, as used in the description that follows, the term "needle shield" is intended to refer to a flexible tip cap (whether made of rubber or some other flexible material) as well as a rigid shield, made of, for example, a rigid plastic or rubber compound) that comes on a pre-filled syringe or covers a staked-in syringe needle or removable needle that can be affixed to a syringe body by, for example, via a Luer taper or Luer-lock fittings, as defined in the ISO 594, and/or DIN and EN 1707:1996[2] and 20594-1:1993 standards.

Figure 77A:
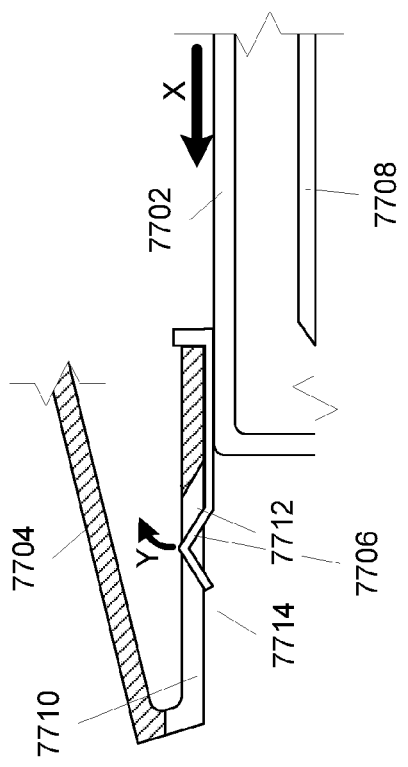
FIGS. 77A through 77C illustrate, in simplified form, a cross section of a representative needle shield 7702 and autoinjector cap 7704 joined together using a low insertion/high grip force approach.
Figure 77B:
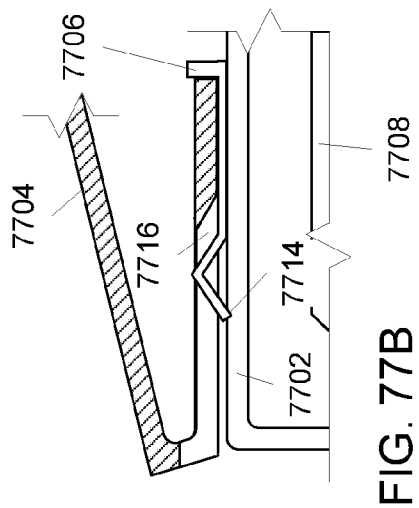
Figure 77C:
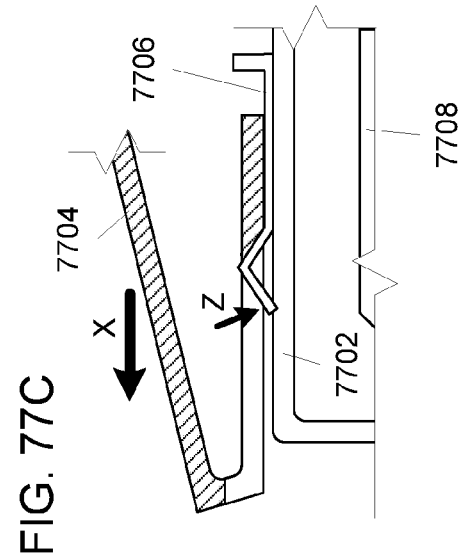

FIGS. 77A through 77C illustrate, in simplified form, a cross section of a representative needle shield 7702 and autoinjector cap 7704 which will be joined together with this approach. In general overview, as shown in FIGS. 77A-77C, the approach uses one or more flexible metal grippers 7706 that allow for easy insertion of the needle shield 7702 into the autoinjector cap 7704 but allows it to solidly grasp the needle shield thereafter.

Specifically, FIG. 77A shows a portion of the needle shield 7702 and associated end of a beveled needle 7708 of a syringe (not shown) as they are being inserted into the autoinjector cap 7704 (i.e. inserted in the direction of arrow X). As can be seen, one of the flexible metal grippers 7706 is visible and interposed between the needle shield 7702 and the autoinjector cap 7704. In addition, as can be seen in the cross section, the autoinjector cap 7704 also includes a cut-out area 7710 that includes a ramped portion 7712, whose function will become evident. As the needle shield 7702 is initially inserted, the sharp tip(s) 7714 of the flexible metal grippers 7706 are displaced by the needle shield 7702 and flex a bit in the direction of the arrow "Y" into the cut-out area 7710 as the needle shield 7702 continues to move into the autoinjector cap 7704. Notably, this configuration allows the needle shield 7702 to be inserted with minimal force.

FIG. 77B shows the needle shield 7702 and associated end of a beveled needle 7708 of the syringe of FIG. 77A when the needle shield 7702 is fully inserted into the autoinjector cap 7704. As can be seen, at this point, the sharp tip(s) 7714 of the flexible metal grippers 7706 abut, and may slightly dig into, the outer surface material of the needle shield 7702. Note further that, at this point, there is a nominal gap 7716 between the end of the flexible metal grippers 7706 and the ramped portion 7712. Depending upon the particular implementation, the gap 7716 need only be large enough to accommodate the flexure of the flexible metal grippers 7706 as the needle shield 7702 is inserted. Depending upon the particular configuration, that gap can be anything in the range from essentially nothing (if the tip can flex out of the way without it, to a few millimeters.

FIG. 77C illustrates the operation of the flexible metal grippers 7706 when the autoinjector cap 7704 is removed. As shown, when the autoinjector cap 7704 is initially pulled in the direction of arrow "X" to expose the needle, the gap 7716 lessens until the ramped portion 7712 contacts the corresponding part of the flexible metal grippers 7706. Further pulling will thereafter cause the ramp to apply a force to the flexible metal grippers 7706 such that the sharp tip 7714 of the flexible metal grippers 7706 will dig further into and "grab" the needle shield 7702 (in the direction of arrow "Z") with significant force, thereby causing the needle shield 7702 to move (and be removed) with the autoinjector cap 7704.

Note further that, although the ends of the flexible metal grippers 7706 are shown as being bent in obtuse angles, this is purely for illustration and curved or other shapes can be used to equal, greater or lesser effect, the important aspect not being the shape, but the configuration that allows for low force insertion of the rigid needle shield but high grip between the flexible metal grippers and rigid needle shield when the autoinjector cap is removed or replaced.

It should be understood that the description herein (including the figures) is only representative of some illustrative variant embodiments. For the convenience of the reader, the above description has focused on a representative sample of variants, not all possible embodiments, a sample that teaches the principles of the invention. The description has not attempted to exhaustively enumerate all possible variations. That alternate embodiments may not have been presented for a specific portion of the invention, or that further undescribed alternate embodiments may be available, is not to be considered a disclaimer of those alternate embodiments. Indeed, certain variants have been provide which may be mutually exclusive in that they cannot simultaneously be present in a single implementation. One of ordinary skill will appreciate that many of the undescribed embodiments, which may include permutations or combinations of the aspects or variants described herein, or other variants, incorporate the same principles of the invention as claimed, and that others are equivalent thereto.

What is claimed is:

1. An autoinjector comprising:
    a main body including
        a container having a drug therein,
        a hollow needle coupled to the container; and
        a power source having:
            a liquefied gas therein as a driver at a first pressure,
            a microporous flow regulator,
            at least one outlet through which some of the driver can exit the power source in a gaseous state,
            the power source and container being coupled together such that, when an injection is initiated, driver exits the power source via the at least one outlet under pressure and the flow regulator controls an exit flow rate of the driver such that the driver provides a second pressure that is less than the first pressure such that an adaptively variable force is provided to drive the drug from the container and out of the main body through the hollow needle.

2. The autoinjector of claim 1, wherein the power source is configured such that the adaptively variable force decreases, if a volumetric rate of drug delivery increases above a desired constant injection rate.

3. The autoinjector of claim 1, wherein the power source is further configured such that the adaptively variable force increases, if the volumetric rate of drug delivery decreases to below a desired constant injection rate.

4. The autoinjector of claim 1, further comprising:
    an intermediate member located between the outlet and the container such that the adaptively variable force applied to the container, via the intermediate member, drives the drug out of the main body.

5. The autoinjector of claim 4, wherein the intermediate member comprises at least one of: a close-ended tube, a sliding cup, a plunger rod, a telescoping column, a flexible ribbon, or a collapsible bellows.

6. The autoinjector of claim 1, further comprising:
    an end of dose indicator that is pressure actuated.

7. The autoinjector of claim 6, wherein the end of dose indicator is configured to provide a visual indication of an end of dose.

8. The autoinjector of claim 6, wherein the end of dose indicator is an audible end of dose indicator that provides an audible indication of an end of dose of the autoinjector.

9. The autoinjector of claim 6, wherein the end of dose indicator is activated when the adaptively variable force exceeds an end of dose pressure level.

10. The autoinjector of claim 6, wherein the end of dose indicator is activated after a complete dose of the drug has been delivered out of the hollow needle.

11. The autoinjector of claim 1, wherein the container is a syringe and wherein, prior to use, the autoinjector further comprises:
    an autoinjector cap;
    at least one flexible metal gripper, having a sharp tip, coupled to the autoinjector cap, the at least one flexible metal gripper being configured to interact with the autoinjector cap to allow for low force insertion of a needle shield of the syringe into the autoinjector cap and to cause the sharp tip to grasp the needle shield of the syringe with an increased force when the autoinjector cap is thereafter removed from the autoinjector for use.

12. The autoinjector of claim 1, wherein the first pressure is about 108 to 845 psi and the second pressure is about 10 to 20 psi.

13. The autoinjector of claim 1, wherein the first pressure is a vapor pressure of the driver and the second pressure is a pressure sufficient to drive the drug from the container and out the main body through the hollow needle in about 3-10 seconds.

14. An autoinjector comprising:
    a main body including
        a container, the container having a drug therein,
        a hollow needle coupled to the container through which the drug can be delivered; and
        a power source having
            a liquefied gas therein as a driver,
            a microporous flow regulator, and
            at least one outlet through which some of the driver can exit the power source in a gaseous state,
        the power source and container being coupled together for operation such that, when an injection is initiated, the flow regulator controls an exit rate of the driver such that the liquefied gas in the power source is maintained at substantially its vapor pressure and the driver applies a first force to deliver the drug via the hollow needle at a delivery rate that is a constant delivery rate, unless an obstruction force that causes the delivery of the drug to change to a reduced delivery rate occurs, and, when the obstruction force that causes the delivery of the drug to change to a reduced delivery rate occurs, the driver applies an increased force in opposition to the obstruction force until the obstruction force is overcome and an increase in rate of drug delivery towards the constant delivery rate is achieved.

15. The autoinjector of claim 14, wherein, prior to use, the autoinjector further comprises:

an autoinjector cap; and at least one flexible metal gripper, having a sharp tip, coupled to the autoinjector cap, the at least one flexible metal gripper being configured to interact with the autoinjector cap to allow for low force insertion of a needle shield of a syringe into the autoinjector cap and to cause the sharp tip to grasp the needle shield of the syringe with an increased force as the autoinjector cap is removed from the autoinjector for use.

16. The autoinjector of claim 14, wherein the power source and container are coupled together for further operation such that, when the obstruction force is overcome, as the increase in rate of drug delivery approaches the constant delivery rate the driver reduces the increased force towards the first force.

17. An autoinjector comprising:
a main body including
a container, the container having a drug therein,
a hollow needle coupled to the container through which the drug can be delivered; and
a power source having
a liquefied gas therein as a driver,
a microporous flow regulator,
at least one outlet through which some of the driver can exit the power source in a gaseous state, and
the power source and container being coupled together for operation such that, when an injection is initiated, the flow regulator controls an exit rate of the driver such that the liquefied gas in the power source is maintained at substantially its vapor pressure and the driver applies a first force to deliver the drug via the hollow needle at a delivery rate that is a constant delivery rate, unless a reduced force opposing the first force is encountered such that the reduced force opposing the first force causes the delivery of the drug to change to an increased delivery rate, and, when the reduced force opposing the first force causes the delivery of the drug to change to the increased delivery rate, the driver applies a force less than the first force until the increased delivery rate has reduced to the constant delivery rate.

18. The autoinjector of claim 17, wherein the power source and container are coupled together for further operation such that, as the increased delivery rate is reduced towards the constant delivery rate, the driver increases the applied force towards the first force.

19. The autoinjector of claim 17, wherein, prior to use, the autoinjector further comprises:

an autoinjector cap; and
at least one flexible metal gripper, having a sharp tip, coupled to the autoinjector cap, the at least one flexible metal gripper being configured to interact with the autoinjector cap to allow for low force insertion of a needle shield of a syringe into the autoinjector cap and to cause the sharp tip to grasp the needle shield of the syringe with an increased force as the autoinjector cap is removed from the autoinjector for use.

20. The autoinjector of claim 17, further comprising an end of dose indicator that is activated when a pressure resulting from the first force exceeds an end of dose pressure level.

21. The autoinjector of claim 17, further comprising an end of dose indicator that is activated after a complete dose of the drug has been delivered out of the hollow needle.

* * * * *